US008617829B2

(12) United States Patent
Kumar et al.

(10) Patent No.: US 8,617,829 B2
(45) Date of Patent: Dec. 31, 2013

(54) HUMANIZED ANTIBODIES SPECIFIC FOR AMINO ACID SEQUENCE RGD OF AN EXTRACELLULAR MATRIX PROTEIN AND THE USES THEREOF

(75) Inventors: Shankar Kumar, Pleasonton, CA (US); J. Yun Tso, Menlo Park, CA (US); Naoya Tsurushita, Palo Alto, CA (US)

(73) Assignee: Gene Techno Science Co., Ltd., Hokkaido (JP)

( * ) Notice: Subject to any disclaimer, the term of this patent is extended or adjusted under 35 U.S.C. 154(b) by 0 days.

(21) Appl. No.: 13/497,692

(22) PCT Filed: Sep. 22, 2010

(86) PCT No.: PCT/JP2010/067017
§ 371 (c)(1),
(2), (4) Date: Mar. 22, 2012

(87) PCT Pub. No.: WO2011/037271
PCT Pub. Date: Mar. 31, 2011

(65) Prior Publication Data
US 2012/0219503 A1 Aug. 30, 2012

Related U.S. Application Data

(60) Provisional application No. 61/272,438, filed on Sep. 24, 2009.

(51) Int. Cl.
*C12Q 1/68* (2006.01)
*C07K 16/00* (2006.01)
*C07K 16/46* (2006.01)
*C07K 16/24* (2006.01)

(52) U.S. Cl.
USPC .. 435/7.1; 530/387.1; 530/387.3; 530/388.22

(58) Field of Classification Search
None
See application file for complete search history.

(56) References Cited

U.S. PATENT DOCUMENTS

| 5,530,101 | A | 6/1996 | Queen et al. |
| 5,859,205 | A | 1/1999 | Adair et al. |
| 7,241,873 | B2 | 7/2007 | Uede et al. |
| 2004/0234524 | A1 | 11/2004 | Uede et al. |
| 2006/0002923 | A1 | 1/2006 | Uede et al. |
| 2011/0065899 | A1 | 3/2011 | Kon et al. |

FOREIGN PATENT DOCUMENTS

| EP | 1 375 518 A1 | 1/2004 |
| EP | 1 637 159 A1 | 3/2006 |
| WO | WO-97/11718 A1 | 4/1997 |
| WO | WO-00/63241 A2 | 10/2000 |
| WO | WO-01/71358 A1 | 9/2001 |
| WO | WO-02/081522 A1 | 10/2002 |
| WO | WO-03/027151 A1 | 4/2003 |
| WO | WO-2008/050907 A1 | 5/2008 |
| WO | WO-2009/131256 A1 | 10/2009 |

OTHER PUBLICATIONS

Yamamoto et al,. "Successful treatment of collagen-induced arthritis in non-human primates by chimeric anti-osteopontin antibody," International Immunopharmacology, 2007, 7:1460-1470.
Bieboer et al., "Guided Selection of a Pan Carcinoma Specific Antibody Reveals Similar Binding Characteristics yet Structural Divergence Between the Original Murine Antibody and its Human Equivalent," J. Mol. Biol., 2000, 296:833-849.
Brown et al., "Tolerance to Single, but Not Multiple, Amino Acid Replacements in Antibody $V_H$CDR2," J. Immunol., 1996, 156:3285-3291.
Klimka et al., "Human anti-CD30 recombinant antibodies by guided phage antibody selection using cell panning," British Journal of Cancer, 2000, 83(2):252-260.
Padlan, Eduardo A., "Anatomy of the Antibody Molecule," Molecular Immunology, 1994, 31(3):169-217.
Paul, William E., M.D., Ed., Fundamental Immunology, Third Edition, 1993, 292-295.
Tsurushita et al., "Design of humanized antibodies: From anti-Tac to Zenapax," Methods, 2005, 36:69-83.
U.S. Appl. No. 12/312,022, filed Oct. 25, 2007, Shigeyuki et al.
U.S. Appl. No. 12/989,208, filed Apr. 24, 209, Kumar et al.
Casset et al., "A peptide mimetic of an anti-CD4 monoclonal antibody by rational design," Biochemical and Biophysical Research Communications, 2003, 307:198-205.
Chen et al., "Selection and Analysis of an Optimized Anti-VEGF Antibody: Crystal Structure of an Affinity-matured Fab in Complex with Antigen," Journal of Molecular Biology, 1999, 293:865-881.
DePascalis et al., "Grafting of 'Abbreviated' Complementarity-Determining Regions Containing specificity-Determining Residues Essential for Ligand Contact to Engineer a Less Immunogenic Humanized Monoclonal Antibody," Journal of Immunology, 2002, 169:3076-3084.
Frisch et al., "Integrins and anoikis," Curr. Opin. Cell Biol., 1997, 9:701-706.
Giancotti et al., "Integrin Signaling," Science, Aug. 13, 1999, 285:1028-1032.
Green et al., "Antibody engineering via genetic engineering of the mouse: XenoMouse strains are a vehicle for the facile generation of therapeutic human monoclonal antibodies," Journal of Immunological Methods, 1999, 231:11-23.
Gu et al., "Laminin-10/11 and Fibronectin Differentially Prevent Apoptosis Induced by Serum via Phosphatidylinositol 3-Kinase/Akt- and MEK1/ERK-dependent Pathways," J. Biol. Chem., May 31, 2002, 277(22):19922-19928.

(Continued)

*Primary Examiner* — Maher Haddad
(74) *Attorney, Agent, or Firm* — Foley & Lardner LLP

(57) ABSTRACT

The present invention provides humanized antibodies that immunospecifically recognize the RGD sequence. Some of these antibodies inhibit the biological functions of the RGD proteins, thereby exhibiting therapeutic effects on various disorders or diseases that are associated with RGD proteins, including cancer, e.g., the growth and metastasis of a cancer cell, and inflammatory diseases, e.g., rheumatoid arthritis, osteoarthritis, hepatitis, endometriosis, bronchial asthma, fibrosis, diabetes, arteriosclerosis, multiple sclerosis, granuloma, an inflammatory bowel disease (ulcerative colitis and Crohn's disease), an autoimmune disease, and so forth.

7 Claims, 27 Drawing Sheets

(56) References Cited

OTHER PUBLICATIONS

Gu et al., "Laminin-10/11 and Fibronectin Differentially Regulate Integrin-dependent Rho and Rac Activation via p130Cas-CrkII-DOCK180 Pathway," J. Biol. Chem., Jul. 20, 2001, 276(29):27090-27097.

Holm et al., "Functional mapping and single chain construction of the anti-cytokeratin 8 monoclonal antibody TS1," Molecular Immunology, 2007, 44:1075-1084.

Kon et al., "Mapping of Functional Epitopes of Osteopontin by Monoclonal Antibodies Raised Against Defined Internal Sequences," Journal of Cellular Biochemistry, Oct. 15, 2001, 84(2):420-432.

MacCallum et al., "Antibody-antigen Interactions: Contact Analysis and Binding Site Topography," J. Mol. Biol., 1996, 262:732-745.

Rudikoff et al., "Single amino acid substitution altering antigen-binding specificity," Proc. Natl. Acad. Sci. USA, Mar. 1982, 79:1979-1983.

Vajdos et al., "Comprehensive Functional Maps of the Antigen-binding Site of an Anti-ErbB2 Antibody Obtained with Shotfun Scanning Mutagenesis," J. Mol. Biol., 2002, 320:415-428.

Vassilev et al., "Inhibition of Cell Adhesion by Antibodies to Arg-Gly-Asp (RGD) in Normal Immunoglobulin for Therapeutic Use (Intravenous Immunoglobulin, IVIg)," Blood, Jun. 1, 1999, 93(11):3624-3631.

Wu et al., "Humanization of a Murine Monoclonal Antibody by Simultaneous Optimization of Framework and CDR Residues," J. Mol. Biol., 1999, 294:151-162.

Johnson et al., "The Kabat Database and a Bioinformatics Example," Methods in Molecular Biology, 2004, 248:11-25.

Osbourn et al., "Current methods for the generation of human antibodies for the treatment of autoimmune diseases," Drug Discovery Today, Sep. 2003, 8(18):845-851.

Almagro et al., "Humanization of antibodies," Frontiers in Bioscience, Jan. 1, 2008, 13:1619-1633.

ATGAAGTTGTGGCTGAACTGGATTTTCCTTGTAACACTTTTAAATGGTTTCCAGTGTGAG
 M   K   L   W   L   N   W   I   F   L   V   T   L   L   N   G   F   Q   C   E̲

GTGAAGCTGGTGGAGTCTGGAGGAGGCTTGGTACAGCCTGGGGGTTCTCTGAGTCTCTCC
 V   K   L   V   E   S   G   G   G   L   V   Q   P   G   G   S   L   S   L   S

TGTGCAGCTTCTGGATTCACCTTCACTGATTACTACATGATCTGGGTCCGCCAGCCTCCA
 C   A   A   S   G   F   T   F   T   D̲   Y̲   Y̲   M̲   I̲   W   V   R   Q   P   P

GGGAAGGCACTTGAGTGGTTGGGTTTTATTAGAAACAAAGCTAATGGTTACACAACAGAG
 G   K   A   L   E   W   L   G   F̲   I̲   R̲   N̲   K̲   A̲   N̲   G̲   Y̲   T̲   T̲   E̲

TACAGTGCATCTGTGAAGGGTCGGTTCACCATCTCCAGAGATAATTCCCAAAGCATCCTC
 Y̲   S̲   A̲   S̲   V̲   K̲   G   R   F   T   I   S   R   D   N   S   Q   S   I   L

TATCTTCAAATGAATGCCCTGAGAGCTGAGGACAGTGCCACTTATTACTGTGCAAGGGGG
 Y   L   Q   M   N   A   L   R   A   E   D   S   A   T   Y   Y   C   A   R   G̲

GCTTACTGGGGCCAAGGGACTCTGGTCACTGTCTCTGCA
 A̲   Y̲   W   G   Q   G   T   L   V   T   V   S   A

FIG. 1

```
ATGAAGTTGCCTGTTAGGCTGTTGGTGCTGATGTTCTGGATTCCTGCTTCCAGCAGTGAT
 M   K   L   P   V   R   L   L   V   L   M   F   W   I   P   A   S   S   S   D

GTTTTGATGACCCAAACTCCACTCTCCCTGCCTGTCAGTCTTGGAGATCAAGCCTCCATC
 V   L   M   T   Q   P   L   S   L   P   V   S   L   G   D   Q   A   S   I

TCTTGCAGATCTAGTCAGAGCATTGTACATAGTAATGGAAACACCTATTTAGAATGGTAC
 S   C   R   S   S   Q   S   I   V   H   S   N   G   N   T   Y   L   E   W   Y

CTGCAGAAACCAGGCCAGTCTCCAAAGCTCCTGATCTACAGAGTTTCCAACCGATTTTCT
 L   Q   K   P   G   Q   S   P   K   L   L   I   Y   R   V   S   N   R   F   S

GGGGTCCCAGACAGGTTCAGTGGCAGTGGATCAGGGACAGATTTCACACTCAAGATCAGC
 G   V   P   D   R   F   S   G   S   G   S   G   T   D   F   T   L   K   I   S

AGAGTGGAGGCTGAGGATCTGGGAGTTTATTACTGCTTTCAAGGTTCATTTGTTCCGTGG
 R   V   E   A   E   D   L   G   V   Y   Y   C   F   Q   G   S   F   V   P   W

ACGTTCGGTGGAGGCACCAAGCTGGAAATCAAA
 T   F   G   G   G   T   K   L   E   I   K
```

FIG. 2

SpeI
ACTAGTACCACCATGAAGTTGTGGCTGAACTGGATTTTCCTTGTAACACTTTTAAATGGT
         M   K   L   W   L   N   W   I   F   L   V   T   L   L   N   G

TTCCAGTGTGAGGTGAAGCTGGTGGAGTCTGGAGGAGGCTTGGTACAGCCTGGGGGTTCT
 F   Q   C   E   V   K   L   V   E   S   G   G   G   L   V   Q   P   G   G   S

CTGAGTCTCTCCTGTGCAGCTTCTGGATTCACCTTCACTGATTACTACATGATCTGGGTC
 L   S   L   S   C   A   A   S   G   F   T   F   T   D   Y   Y   M   I   W   V

CGCCAGCCTCCAGGGAAGGCACTTGAGTGGTTGGGTTTTATTAGAAACAAAGCTAATGGT
 R   Q   P   P   G   K   A   L   E   W   L   G   F   I   R   N   K   A   N   G

TACACAACAGAGTACAGTGCATCTGTGAAGGGTCGGTTCACCATCTCCAGAGATAATTCC
 Y   T   T   E   Y   S   A   S   V   K   G   R   F   T   I   S   R   D   N   S

CAAAGCATCCTCTATCTTCAAATGAATGCCCTGAGAGCTGAGGACAGTGCCACTTATTAC
 Q   S   I   L   Y   L   Q   M   N   A   L   R   A   E   D   S   A   T   Y   Y

TGTGCAAGGGGGGCTTACTGGGGCCAAGGGACTCTGGTCACTGTCTCTGCAG*GTGAGTCC*
 C   A   R   G   A   Y   W   G   Q   G   T   L   V   T   V   S   A

HindIII
*TAACTTCAAGCTT*

FIG. 3

```
NheI
GCTAGCACCACCATGAAGTTGCCTGTTAGGCTGTTGGTGCTGATGTTCTGGATTCCTGCT
            M   K   L   P   V   R   L   L   V   L   M   F   W   I   P   A

TCCAGCAGTGATGTTTTGATGACCCAAACTCCACTCTCCCTGCCTGTCAGTCTTGGAGAT
 S   S   S   D   V   L   M   T   Q   T   P   L   S   L   P   V   S   L   G   D

CAAGCCTCCATCTCTTGCAGATCTAGTCAGAGCATTGTACATAGTAATGGAAACACCTAT
 Q   A   S   I   S   C   R   S   S   Q   S   I   V   H   S   N   G   N   T   Y

TTAGAATGGTACCTGCAGAAACCAGGCCAGTCTCCAAAGCTCCTGATCTACAGAGTTTCC
 L   E   W   Y   L   Q   K   P   G   Q   S   P   K   L   L   I   Y   R   V   S

AACCGATTTTCTGGGGTCCCAGACAGGTTCAGTGGCAGTGGATCAGGGACAGATTTCACA
 N   R   F   S   G   V   P   D   R   F   S   G   S   G   S   G   T   D   F   T

CTCAAGATCAGCAGAGTGGAGGCTGAGGATCTGGGAGTTTATTACTGCTTTCAAGGTTCA
 L   K   I   S   R   V   E   A   E   D   L   G   V   Y   Y   C   F   Q   G   S

TTTGTTCCGTGGACGTTCGGTGGAGGCACCAAGCTGGAAATCAAAC GTAAGTAGAATCCA
 F   V   P   W   T   F   G   G   G   T   K   L   E   I   K

EcoRI
AAGAATTC
```

FIG. 4

```
                        1           2           3
            123456789  0123456789  0123456789  0123456789
33E10 VH    EVKLVESGG  GLVQPGGSLS  LSCAASGFTF  TDYYMIWVRQ
Hu33E10 VH1 EVQLVESGG  GLVQPGGSLR  LSCAASGFTF  TDYYMIWVRQ
U03400      EVQLVESGG  GLVQPGGSLR  LSCAASGFTF  S-----WVRQ 4           5            6           7
            0123456789  0122223456789 0123456789  0123456789
                          abc
33E10 VH    PPGKALEWLG  FIRNKANGYTTEY SASVKGRFTI  SRDNSQSILY
Hu33E10 VH1 APGKGLEWLG  FIRNKANGYTTEY SASVKGRFTI  SRDNAKNSLY
U03400      APGKGLEWVG  ------------- ------RFTI  SRDNAKNSLY 1           1
            8             9            0           1
            0122223456789 0123456789   0123456789  0123
              abc
33E10 VH    LQMNALRAEDSAT YYCARG----   -AYWGQGTLV  TVSA
Hu33E10 VH1 LQMNSLRAEDTAV YYCARG----   -AYWGQGTMV  TVSS
U03400      LQMNSLRAEDTAV YYCAR-----   ---WGQGTMV  TVSS
```

FIG. 6

```
                        1              2                3
            123456789  0123456789  012345677777789  0123456789
                                          abcde
33E10 VL    DVLMTQTPL  SLPVSLGDQA  SISCRSSQSIVHSNG  NTYLEWYLQK
Hu33E10 VL1 DIVMTQSPL  SLPVTPGEPA  SISCRSSQSIVHSNG  NTYLEWYLQK
X72452      DIVMTQSPL  SLPVTPGEPA  SISC-----------  -----WYLQK 4           5           6           7
            0123456789  0123456789  0123456789  0123456789
33E10 VL    PGQSPKLLIY  RVSNRFSGVP  DRFSGSGSGT  DFTLKISRVE
Hu33E10 VL1 PGQSPQLLIY  RVSNRFSGVP  DRFSGSGSGT  DFTLKISRVE
X72452      PGQSPQLLIY  -------GVP  DRFSGSGSGT  DFTLKISRVE 1
            8           9           0
            0123456789  0123456789  01234567
33E10 VL    AEDLGVYYCF  QGSFVPWTFG  GGTKLEIK
Hu33E10 VL1 AEDVGVYYCF  QGSFVPWTFG  QGTKVEIK
X72452      AEDVGVYYC-  --------FG  QGTKVEIK
```

FIG. 7

| | |
|---|---|
| JNJ220 | GGGACTAGTACCACCATGAAG |
| JNJ206 | GGGACTAGTACCACCATGAAGTTGTGGCTGAACTGGATTTTCCTTGTAACACTT |
| JNJ207 | CAGCTGCACTTCACACTGGAAACCATTTAAAAGTGTTACAAGGAAAATCCA |
| JNJ208 | TTCCAGTGTGAAGTGCAGCTGGTGGAGTCTGGAGGAGGCTTGGTACAGCCT |
| JNJ209 | AGCTGCACAGGAGAGTCTCAGAGAACCCCCAGGCTGTACCAAGCCTCCTCC |
| JNJ210 | CTGAGACTCTCCTGTGCAGCTTCTGGATTCACCTTCACTGATTACTACATG |
| JNJ211 | TCCCTTCCCTGGAGCCTGGCGGACCCAGATCATGTAGTAATCAGTGAAGGT |
| JNJ212 | CGCCAGGCTCCAGGGAAGGGACTTGAGTGGTTGGGTTTTATTAGAAACAAA |
| JNJ213 | TGCACTGTACTCTGTTGTGTAACCATTAGCTTTGTTTCTAATAAAACCCAA |
| JNJ214 | TACACAACAGAGTACAGTGCATCTGTGAAGGGTCGGTTCACCATCTCCAGA |
| JNJ215 | TTGAAGATAGAGTGAGTTCTTGGCATTATCTCTGGAGATGGTGAACCGACC |
| JNJ216 | AAGAACTCACTCTATCTTCAAATGAACTCCCTGAGAGCTGAGGACACGGCC |
| JNJ217 | CCAGTAAGCGCCCCTTGCACAGTAATACACGGCCGTGTCCTCAGCTCTCAG |
| JNJ218 | TGTGCAAGGGGCGCTTACTGGGGCCAAGGGACTATGGTCACTGTCTCTTCA |
| JNJ219 | GGGAAGCTTGGAAAGCCCATCTTACCTGAAGAGACAGTGACCATAGT |
| JNJ221 | GGGAAGCTTGGAAAGCCCATC |

FIG. 8

| | |
|---|---|
| JNJ116 | GGGCTAGCACCACCATGAGG |
| JNJ193 | GGGCTAGCACCACCATGAGGACCCCTGCTCAGTTTCTTGGAATCTTGTTGCTC |
| JNJ194 | CACAATATCACATTTGATACCTGGAAACCAGAGCAACAAGATTCCAAGAAA |
| JNJ195 | GGTATCAAATGTGATATTGTGATGACCCAATCTCCACTCTCCCTGCCTGTC |
| JNJ196 | GCAAGAGATGGAGGCTGGCTCTCCAGGAGTGACAGGCAGGGAGAGTGGAGA |
| JNJ197 | GAGCCAGCCTCCATCTCTTGCAGATCTAGTCAGAGCATTGTACATAGTAAT |
| JNJ198 | CTGCAGGTACCATTCTAAATAGGTGTTTCCATTACTATGTACAATGCTCTG |
| JNJ199 | TATTTAGAATGGTACCTGCAGAAACCAGGCCAGTCTCCACAGCTCCTGATC |
| JNJ200 | GACCCCAGAAAATCGGTTGGAAACTCTGTAGATCAGGAGCTGTGGAGACTG |
| JNJ201 | TCCAACCGATTTTCTGGGGTCCCAGACAGGTTCAGTGGCAGTGGATCAGGG |
| JNJ202 | CACTCTGCTGATCTTGAGTGTGAAATCTGTCCCTGATCCACTGCCACTGAA |
| JNJ203 | ACACTCAAGATCAGCAGAGTGGAGGCTGAGGATGTCGGAGTTTATTACTGC |
| JNJ204 | GAACGTCCACGGAACAAATGAACCTTGAAAGCAGTAATAAACTCCGACATC |
| JNJ205 | TCATTTGTTCCGTGGACGTTCGGTCAAGGCACCAAAGTGGAAATCAAACGTGAGTAG |
| JNJ101 | GGGGAATTCTTTAAATTCTACTCACGTTTGATTTCCA |
| JNJ117 | GGGGAATTCTTTAAATTCTA |

FIG. 9

```
    SpeI
GGGACTAGTACCACC ATG AAG TTG TGG CTG AAC TGG ATT TTC CTT GTA ACA CTT TTA AAT GGT
              ▶ M   K   L   W   L   N   W   I   F   L   V   T   L   L   N   G
─────────────────────────────────────────────────────────────────────────────▶
JNJ220 ────▶       JNJ206 ◀────                      JNJ207
```

```
              PvuII
TTC CAG TGT GAA GTG CAG CTG GTG GAG TCT GGA GGA GGC TTG GTA CAG CCT GGG GGT TCT
▶F   Q   C   E   V   Q   L   V   E   S   G   G   G   L   V   Q   P   G   G   S
──────────────────── JNJ208 ◀────────────────────────▶
                                              JNJ209
```

```
CTG AGA CTC TCC TGT GCA GCT TCT GGA TTC ACC TTC ACT GAT TAC TAC ATG ATC TGG GTC
▶L   R   L   S   C   A   A   S   G   F   T   F   T   D   Y   Y   M   I   W   V
───────────────── JNJ210 ◀────────────────▶
                                        JNJ211
```

```
CGC CAG GCT CCA GGG AAG GGA CTT GAG TGG TTG GGT TTT ATT AGA AAC AAA GCT AAT GGT
▶R   Q   A   P   G   K   G   L   E   W   L   G   F   I   R   N   K   A   N   G
───────────────── JNJ212 ◀────────────────▶
                                        JNJ213
```

```
TAC ACA ACA GAG TAC AGT GCA TCT GTG AAG GGT CGG TTC ACC ATC TCC AGA GAT AAT GCC
▶Y   T   T   E   Y   S   A   S   V   K   G   R   F   T   I   S   R   D   N   A
───────────────── JNJ214 ◀────────────────▶
                                        JNJ215
```

```
AAG AAC TCA CTC TAT CTT CAA ATG AAC TCC CTG AGA GCT GAG GAC ACG GCC GTG TAT TAC
▶K   N   S   L   Y   L   Q   M   N   S   L   R   A   E   D   T   A   V   Y   Y
───────────────── JNJ216 ◀────────────────▶
                                        JNJ217
```

```
TGT GCA AGG GGC GCT TAC TGG GGC CAA GGG ACT ATG GTC ACT GTC TCT TCA GGTAAGATGGGC
▶C   A   R   G   A   Y   W   G   Q   G   T   M   V   T   V   S   S           ◀──JNJ221
───────────────── JNJ218 ◀────────────────▶
                                        JNJ219
```

```
    HindIII
TTTCCAAGCTTCCC
──────────────
──────────────
```

FIG. 10

```
Nhel
GGGCTAGCACCACC ATG AGG ACC CCT GCT CAG TTT CTT GGA ATC TTG TTG CTC TGG TTT CCA
               ▶ M   R   T   P   A   Q   F   L   G   I   L   L   L   W   F   P
───────────────────────────────▶      JNJ193 ◀───────────────────────────────
─────────────────────▶
       JNJ116                                               JNJ194

GGT ATC AAA TGT GAT ATT GTG ATG ACC CAA TCT CCA CTC TCC CTG CCT GTC ACT CCT GGA
▶ G   I   K   C   D   I   V   M   T   Q   S   P   L   S   L   P   V   T   P   G
─────────────────────────── JNJ195 ◀───────────────────────────
                                                    JNJ196

GAG CCA GCC TCC ATC TCT TGC AGA TCT AGT CAG AGC ATT GTA CAT AGT AAT GGA AAC ACC
▶ E   P   A   S   I   S   C   R   S   S   Q   S   I   V   H   S   N   G   N   T
─────────────────────────── JNJ197 ◀───────────────────────────
                                                    JNJ198

TAT TTA GAA TGG TAC CTG CAG AAA CCA GGC CAG TCT CCA CAG CTC CTG ATC TAC AGA GTT
▶ Y   L   E   W   Y   L   Q   K   P   G   Q   S   P   Q   L   L   I   Y   R   V
─────────────────────────── JNJ199 ◀───────────────────────────
                                                    JNJ200

TCC AAC CGA TTT TCT GGG GTC CCA GAC AGG TTC AGT GGC AGT GGA TCA GGG ACA GAT TTC
▶ S   N   R   F   S   G   V   P   D   R   F   S   G   S   G   S   G   T   D   F
─────────────────────────── JNJ201 ◀───────────────────────────
                                                    JNJ202

ACA CTC AAG ATC AGC AGA GTG GAG GCT GAG GAT GTC GGA GTT TAT TAC TGC TTT CAA GGT
▶ T   L   K   I   S   R   V   E   A   E   D   V   G   V   Y   Y   C   F   Q   G
─────────────────────────── JNJ203 ◀───────────────────────────
                                                    JNJ204

TCA TTT GTT CCG TGG ACG TTC GGT CAA GGC ACC AAA GTG GAA ATC AAA CGTGAGTAGAATTTAAA
▶ S   F   V   P   W   T   F   G   Q   G   T   K   V   E   I   K           ─────▶
─────────────────────────── JNJ205 ◀───────────────────────────
                                                    JNJ101 ◀──────
                                                              JNJ117

EcoRI
GAATTCCCC

```
SpeI
ACTAGTACCACCATGAAGTTGTGGCTGAACTGGATTTTCCTTGTAACACTTTTAAATGGT
         M   K   L   W   L   N   W   I   F   L   V   T   L   L   N   G

TTCCAGTGTGAAGTGCAGCTGGTGGAGTCTGGAGGAGGCTTGGTACAGCCTGGGGGTTCT
 F   Q   C   E   V   Q   L   V   E   S   G   G   G   L   V   Q   P   G   G   S

CTGAGACTCTCCTGTGCAGCTTCTGGATTCACCTTCACTGATTACTACATGATCTGGGTC
 L   R   L   S   C   A   A   S   G   F   T   F   T   D   Y   Y   M   I   W   V

CGCCAGGCTCCAGGGAAGGGACTTGAGTGGTTGGGTTTTATTAGAAACAAAGCTAATGGT
 R   Q   A   P   G   K   G   L   E   W   L   G   F   I   R   N   K   A   N   G

TACACAACAGAGTACAGTGCATCTGTGAAGGGTCGGTTCACCATCTCCAGAGATAATGCC
 Y   T   T   E   Y   S   A   S   V   K   G   R   F   T   I   S   R   D   N   A

AAGAACTCACTCTATCTTCAAATGAATTCCCTGAGAGCTGAGGACACGGCCGTGTATTAC
 K   N   S   L   Y   L   Q   M   N   S   L   R   A   E   D   T   A   V   Y   Y

TGTGCAAGGGGCGCTTACTGGGGCCAAGGGACTATGGTCACTGTCTCTTCAGgtaagatg
 C   A   R   G   A   Y   W   G   Q   G   T   M   V   T   V   S   S HindIII
GGCTTTCCAAGCTT
```

FIG. 12

NheI
GCTAGCACCACCATGAGGACCCCTGCTCAGTTTCTTGGAATCTTGTTGCTCTGGTTTCCA
           M   R   T   P   A   Q   F   L   G   I   L   L   W   F   P

GGTATCAAATGTGATATTGTGATGACCCAATCTCCACTCTCCCTGCCTGTCACTCCTGGA
 G   I   K   C   D   I   V   M   T   Q   S   P   L   S   P   V   T   P   G

GAGCCAGCCTCCATCTCTTGCAGATCTAGTCAGAGCATTGTACATAGTAATGGAAACACC
 E   P   A   S   I   S   C   R   S   S   Q   S   I   V   H   S   N   G   N   T

TATTTAGAATGGTACCTGCAGAAACCAGGCCAGTCTCCACAGCTCCTGATCTACAGAGTT
 Y   L   E   W   Y   L   Q   K   P   G   Q   S   P   Q   L   L   I   Y   R   V

TCCAACCGATTTTCTGGGGTCCCAGACAGGTTCAGTGGCAGTGGATCAGGGACAGATTTC
 S   N   R   F   S   G   V   P   D   R   F   S   G   S   G   S   G   T   D   F

ACACTCAAGATCAGCAGAGTGGAGGCTGAGGATGTCGGAGTTTATTACTGCTTTCAAGGT
 T   L   K   I   S   R   V   E   A   E   D   V   G   V   Y   Y   C   F   Q   G

TCATTTGTTCCGTGGACGTTCGGTCAAGGCACCAAAGTGGAAATCAAAC*GTGAGTAGAAT*
 S   F   V   P   W   T   F   G   Q   G   T   K   V   E   I   K

EcoRI
*TTAAAGAATTC*

FIG. 13

```
NheI
GCTAGCACCACCATGAGGACCCCTGCTCAGTTTCTTGGAATCTTGTTGCTCTGGTTTCCA
          M   R   T   P   A   Q   F   L   G   I   L   L   W   F   P

GGAATCAAATGTGATATTGTGATGACCCAATCTCCACTCTCCCTGCCTGTCACTCCTGGA
  G   I   K   C   D   I   V   M   T   Q   S   P   L   S   P   V   T   P   G

GAGCCAGCCTCCATCTCTTGCAGATCTAGTCAGAGCATTGTACATAGTAATGGAAACACC
  E   P   A   S   I   S   C   R   S   S   Q   S   I   V   H   S   N   G   N   T

TATTTAGAATGGTACCTGCAGAAACCAGGCCAGTCTCCACAGCTCCTGATCTACAGAGTT
  Y   L   E   W   Y   L   Q   K   P   G   Q   S   P   Q   L   L   I   Y   R   V

TCCAACCGATTTTCTGGGGTCCCAGACAGGTTCAGTGGCAGTGGATCAGGGACAGATTTC
  S   N   R   F   S   G   V   P   D   R   F   S   G   S   G   S   G   T   D   F

ACACTCAAGATCAGCAGAGTGGAGGCTGAGGATGTCGGAGTTTATTACTGCTTTCAAGGT
  T   L   K   I   S   R   V   E   A   E   D   V   G   V   Y   Y   C   F   Q   G

TCATTTGTTCCGTGGACGTTCGGTCAAGGCACCAAAGTGGAAATCAAACGTGAGTAGAAT
  S   F   V   P   W   T   F   G   Q   G   T   K   V   E   I   K

EcoRI
TTAAAGAATTC
```

FIG. 14

```
SpeI
ACTAGTACCACCATGAAGTTGTGGCTGAACTGGATTTTCCTTGTAACACTTTTAAATGGT
          M   K   L   W   L   N   W   I   F   L   V   T   L   L   N   G

TTCCAGTGTGAAGTGCAGCTGGTGGAGTCTGGAGGAGGCTTGGTACAGCCTGGGGGTTCT
 F   Q   C   E   V   Q   L   V   E   S   G   G   G   L   V   Q   P   G   G   S

CTGAGACTCTCCTGTGCAGCTTCTGGATTCACCTTCACTGATTACTACATGATCTGGGTC
 L   R   L   S   C   A   A   S   G   F   T   F   T   D   Y   Y   M   I   W   V

CGCCAGGCTCCAGGGAAGGGACTTGAGTGGTTGGGTTTTATTAGAAACAAAGCTAATGGT
 R   Q   A   P   G   K   G   L   E   W   L   G   F   I   R   N   K   A   N   G

TACACAACAGAGTACAGTGCATCTGTGAAGGGTCGGTTCACCATCTCCAGAGATAATGCC
 Y   T   T   E   Y   S   A   S   V   K   G   R   F   T   I   S   R   D   N   A

AAGAACATCCTCTATCTTCAAATGAATTCCCTGAGAGCTGAGGACACGGCCGTGTATTAC
 K   N   I   L   Y   L   Q   M   N   S   L   R   A   E   D   T   A   V   Y   Y

TGTGCAAGGGGCGCTTACTGGGGCCAAGGGACTATGGTCACTGTCTCTTCAGgtaagatg
 C   A   R   G   A   Y   W   G   Q   G   T   M   V   T   V   S   S HindIII
GGCTTTCCAAGCTT
```

FIG. 16

SpeI
ACTAGTACCACCATGAAGTTGTGGCTGAACTGGATTTTCCTTGTAACACTTTTAAATGGT
         M   K   L   W   L   N   W   I   F   L   V   T   L   L   N   G

TTCCAGTGTGAAGTGCAGCTGGTGGAGTCTGGAGGAGGCTTGGTACAGCCTGGGGGTTCT
 F   Q   C   E   V   Q   L   V   E   S   G   G   G   L   V   Q   P   G   G   S

CTGAGACTCTCCTGTGCAGCTTCTGGATTCACCTTCACTGATTACTACATGATCTGGGTC
 L   R   L   S   C   A   A   S   G   F   T   F   T   <u>D   Y   Y   M   I</u>   W   V

CGCCAGGCTCCAGGGAAGGGACTTGAGTGGTTGGGTTTTATTAGAAACAAAGCTAATGGT
 R   Q   A   P   G   K   G   L   E   W   L   G   <u>F   I   R   N   K   A   N   G

TACACAACAGAGTACAGTGCATCTGTGAAGGGTCGGTTCACCATCTCCAGAGATAATGCC
 Y   T   T   E   Y   S   A   S   V   K</u>   G   R   F   T   I   S   R   D   N   A

AAGAGCATCCTCTATCTTCAAATGAATTCCCTGAGAGCTGAGGACACGGCCGTGTATTAC
 K   <u>S   I</u>   L   Y   L   Q   M   N   S   L   R   A   E   D   T   A   V   Y   Y

TGTGCAAGGGGCGCTTACTGGGGCCAAGGGACTATGGTCACTGTCTCTTCAG*GTAAGATG*
 C   A   R   <u>G   A   Y</u>   W   G   Q   G   T   M   V   T   V   S   S

HindIII
*GGCTTTCC*<u>*AAGCTT*</u>

FIG. 17

```
SpeI
ACTAGTACCACCATGAAGTTGTGGCTGAACTGGATTTTCCTTGTAACACTTTTAAATGGT
         M   K   L   W   L   N   W   I   F   L   V   T   L   L   N   G

TTCCAGTGTGAAGTGCAGCTGGTGGAGTCTGGAGGAGGCTTGGTACAGCCTGGGGGTTCT
 F   Q   C   E   V   Q   L   V   E   S   G   G   G   L   V   Q   P   G   G   S

CTGAGACTCTCCTGTGCAGCTTCTGGATTCACCTTCACTGATTACTACATGATCTGGGTC
 L   R   L   S   C   A   A   S   G   F   T   F   T   D   Y   Y   M   I   W   V

CGCCAGGCTCCAGGGAAGGGACTTGAGTGGTTGGGTTTTATTAGAAACAAAGCTAATGGT
 R   Q   A   P   G   K   G   L   E   W   L   G   F   I   R   N   K   A   N   G

TACACAACAGAGTACAGTGCATCTGTGAAGGGTCGGTTCACCATCTCCAGAGATAATTCC
 Y   T   T   E   Y   S   A   S   V   K   G   R   F   T   I   S   R   D   N   S

AAGAGCATCCTCTATCTTCAAATGAATTCCCTGAGAGCTGAGGACACGGCCGTGTATTAC
 K   S   I   L   Y   L   Q   M   N   S   L   R   A   E   D   T   A   V   Y   Y

TGTGCAAGGGGCGCTTACTGGGGCCAAGGGACTATGGTCACTGTCTCTTCAGGTAAGATG
 C   A   R   G   A   Y   W   G   Q   G   T   M   V   T   V   S   S

HindIII
GGCTTTCCAAGCTT
```

FIG. 18

```
                        1          2               3
             123456789  0123456789 012345677777789 0123456789
                                         abcde
33E10 VL     DVLMTQTPL  SLPVSLGDQA SISCRSSQSIVHSNG NTYLEWYLQK
Hu33E10 VLv2 DIVMTQSPD  SLAVSLGERA TISCRSSQSIVHSNG NTYLEWYLQK
M29467       DIVMTQSPD  SLAVSLGERA TINC---------- ------WYQQK 4          5          6          7
             0123456789 0123456789 0123456789 0123456789
33E10 VL     PGQSPKLLIY RVSNRFSGVP DRFSGSGSGT DFTLKISRVE
Hu33E10 VLv2 PGQPPKLLIY RVSNRFSGVP DRFSGSGSGT DFTLTISSLQ
M29467       PGQPPKLLIY -------GVP DRFSGSGSGT DFTLTISSLQ 1
             8          9          0
             0123456789 0123456789 01234567
33E10 VL     AEDLGVYYCF QGSFVPWTFG GGTKLEIK
Hu33E10 VLv2 AEDVAVYYCF QGSFVPWTFG QGTKVEIK
M29467       AEDVAVYYC- -------FG QGTKVEIK
```

FIG. 19

```
NheI
GCTAGCACCACCATGAGGACCCCTGCTCAGTTTCTTGGAATCTTGTTGCTCTGGTTTCCA
         M  R  T  P  A  Q  F  L  G  I  L  L  L  W  F  P

GGAATCAAATGTGATATCGTGATGACCCAATCTCCAGACTCCCTGGCTGTCAGTCTTGGA
 G  I  K  C  D  I  V  M  T  Q  S  P  D  S  L  A  V  S  L  G

GAGAGGGCCACCATCTCTTGCAGATCTAGTCAGAGCATTGTACATAGTAATGGAAACACC
 E  R  A  T  I  S  C  R  S  S  Q  S  I  V  H  S  N  G  N  T

TATTTAGAATGGTACCTGCAGAAACCAGGCCAGCCTCCAAAGCTCCTGATCTACAGAGTT
 Y  L  E  W  Y  L  Q  K  P  G  Q  P  P  K  L  L  I  Y  R  V

TCCAACCGATTTTCTGGGGTCCCAGACAGGTTCAGTGGCAGTGGATCAGGGACAGATTTC
 S  N  R  F  S  G  V  P  D  R  F  S  G  S  G  S  G  T  D  F

ACACTCACCATCAGCAGCCTGCAGGCTGAGGATGTGGCAGTTTATTACTGCTTTCAAGGT
 T  L  T  I  S  S  L  Q  A  E  D  V  A  V  Y  Y  C  F  Q  G

TCATTTGTTCCGTGGACGTTCGGTCAAGGCACCAAGGTGGAAATCAAACGTGAGTAGAAT
 S  F  V  P  W  T  F  G  Q  G  T  K  V  E  I  K

EcoRI
TTAAAGAATTC
```

FIG. 20

| | |
|---|---|
| CMV2 | GAACCGTCAGATCGCCTGGAGACG |
| JNT026 | TGAAAGATGAGCTGGAGGAC |
| JNT080 | GAACTGTGGCTGCACCATC |
| JNT082 | CTTTCTTGTCCACCTTGGTG |
| JNT084 | GTTGAAGCTCTTTGTGACGG |
| JNT097 | GCTGTCCTACAGTCCTCAG |
| JNT098 | ACGTGCCAAGCATCCTCG |

FIG. 22

```
ATGAAGTTGTGGCTGAACTGGATTTTCCTTGTAACACTTTTAAATGGTTTCCAGTGTGAA
 M   K   L   W   L   N   W   I   F   L   V   T   L   L   N   G   F   Q   C   E
GTGCAGCTGGTGGAGTCTGGAGGAGGCTTGGTACAGCCTGGGGGTTCTCTGAGACTCTCC
 V   Q   L   V   E   S   G   G   G   L   V   Q   P   G   G   S   L   R   L   S
TGTGCAGCTTCTGGATTCACCTTCACTGATTACTACATGATCTGGGTCCGCCAGGCTCCA
 C   A   A   S   G   F   T   F   T   D   Y   Y   M   I   W   V   R   Q   A   P
GGGAAGGGACTTGAGTGGTTGGGTTTTATTAGAAACAAAGCTAATGGTTACACAACAGAG
 G   K   G   L   E   W   L   G   F   I   R   N   K   A   N   G   Y   T   T   E
TACAGTGCATCTGTGAAGGGTCGGTTCACCATCTCCAGAGATAATGCCAAGAGCATCCTC
 Y   S   A   S   V   K   G   R   F   T   I   S   R   D   N   A   K   S   I   L
TATCTTCAAATGAACTCCCTGAGAGCTGAGGACACGGCCGTGTATTACTGTGCAAGGGGC
 Y   L   Q   M   N   S   L   R   A   E   D   T   A   V   Y   Y   C   A   R   G
GCTTACTGGGGCCAAGGGACTATGGTCACTGTCTCTTCAGCCTCCACCAAGGGCCCATCG
 A   Y   W   G   Q   G   T   M   V   T   V   S   S   A   S   T   K   G   P   S
GTCTTCCCCCTGGCACCCTCCTCCAAGAGCACCTCTGGGGGCACAGCGGCCCTGGGCTGC
 V   F   P   L   A   P   S   S   K   S   T   S   G   G   T   A   A   L   G   C
CTGGTCAAGGACTACTTCCCCGAACCGGTGACGGTGTCGTGGAACTCAGGCGCCCTGACC
 L   V   K   D   Y   F   P   E   P   V   T   V   S   W   N   S   G   A   L   T
AGCGGCGTGCACACCTTCCCGGCTGTCCTACAGTCCTCAGGACTCTACTCCCTCAGCAGC
 S   G   V   H   T   F   P   A   V   L   Q   S   S   G   L   Y   S   L   S   S
GTGGTGACCGTGCCCTCCAGCAGCTTGGGCACCCAGACCTACATCTGCAACGTGAATCAC
 V   V   T   V   P   S   S   S   L   G   T   Q   T   Y   I   C   N   V   N   H
AAGCCCAGCAACACCAAGGTGGACAAGAAAGTTGAGCCCAAATCTTGTGACAAAACTCAC
 K   P   S   N   T   K   V   D   K   K   V   E   P   K   S   C   D   K   T   H
ACATGCCCACCGTGCCCAGCACCTGAACTCCTGGGGGGACCGTCAGTCTTCCTCTTCCCC
 T   C   P   P   C   P   A   P   E   L   L   G   G   P   S   V   F   L   F   P
CCAAAACCCAAGGACACCCTCATGATCTCCCGGACCCCTGAGGTCACATGCGTGGTGGTG
 P   K   P   K   D   T   L   M   I   S   R   T   P   E   V   T   C   V   V   V
GACGTGAGCCACGAAGACCCTGAGGTCAAGTTCAACTGGTACGTGGACGGCGTGGAGGTG
 D   V   S   H   E   D   P   E   V   K   F   N   W   Y   V   D   G   V   E   V
CATAATGCCAAGACAAAGCCGCGGGAGGAGCAGTACAACAGCACGTACCGTGTGGTCAGC
 H   N   A   K   T   K   P   R   E   E   Q   Y   N   S   T   Y   R   V   V   S
GTCCTCACCGTCCTGCACCAGGACTGGCTGAATGGCAAGGAGTACAAGTGCAAGGTCTCC
 V   L   T   V   L   H   Q   D   W   L   N   G   K   E   Y   K   C   K   V   S
AACAAAGCCCTCCCAGCCCCCATCGAGAAAACCATCTCCAAAGCCAAAGGGCAGCCCCGA
 N   K   A   L   P   A   P   I   E   K   T   I   S   K   A   K   G   Q   P   R
GAACCACAGGTGTACACCCTGCCCCCATCCCGGGATGAGCTGACCAAGAACCAGGTCAGC
 E   P   Q   V   Y   T   L   P   P   S   R   D   E   L   T   K   N   Q   V   S
CTGACCTGCCTGGTCAAAGGCTTCTATCCCAGCGACATCGCCGTGGAGTGGGAGAGCAAT
 L   T   C   L   V   K   G   F   Y   P   S   D   I   A   V   E   W   E   S   N
GGGCAGCCGGAGAACAACTACAAGACCACGCCTCCCGTGCTGGACTCCGACGGCTCCTTC
 G   Q   P   E   N   N   Y   K   T   T   P   P   V   L   D   S   D   G   S   F
TTCCTCTACAGCAAGCTCACCGTGGACAAGAGCAGGTGGCAGCAGGGGAACGTCTTCTCA
 F   L   Y   S   K   L   T   V   D   K   S   R   W   Q   Q   G   N   V   F   S
TGCTCCGTGATGCATGAGGCTCTGCACAACCACTACACGCAGAAGAGCCTCTCCCTGTCT
 C   S   V   M   H   E   A   L   H   N   H   Y   T   Q   K   S   L   S   L   S
CCGGGTAAATGA
 P   G   K   •
```

FIG. 23

```
ATGAAGTTGTGGCTGAACTGGATTTTCCTTGTAACACTTTTAAATGGTTTCCAGTGTGAA
 M   K   L   W   L   N   W   I   F   L   V   T   L   L   N   G   F   Q   C   E
GTGCAGCTGGTGGAGTCTGGAGGAGGCTTGGTACAGCCTGGGGGTTCTCTGAGACTCTCC
 V   Q   L   V   E   S   G   G   G   L   V   Q   P   G   G   S   L   R   L   S
TGTGCAGCTTCTGGATTCACCTTCACTGATTACTACATGATCTGGGTCCGCCAGGCTCCA
 C   A   A   S   G   F   T   F   T   D   Y   Y   M   I   W   V   R   Q   A   P
GGGAAGGGACTTGAGTGGTTGGGTTTTATTAGAAACAAAGCTAATGGTTACACAACAGAG
 G   K   G   L   E   W   L   G   F   I   R   N   K   A   N   G   Y   T   T   E
TACAGTGCATCTGTGAAGGGTCGGTTCACCATCTCCAGAGATAATTCCAAGAGCATCCTC
 Y   S   A   S   V   K   G   R   F   T   I   S   R   D   N   S   K   S   I   L
TATCTTCAAATGAACTCCCTGAGAGCTGAGGACACGGCCGTGTATTACTGTGCAAGGGGC
 Y   L   Q   M   N   S   L   R   A   E   D   T   A   V   Y   Y   C   A   R   G
GCTTACTGGGGCCAAGGGACTATGGTCACTGTCTCTTCAGCCTCCACCAAGGGCCCATCG
 A   Y   W   G   Q   G   T   M   V   T   V   S   S   A   S   T   K   G   P   S
GTCTTCCCCCTGGCACCCTCCTCCAAGAGCACCTCTGGGGGCACAGCGGCCCTGGGCTGC
 V   F   P   L   A   P   S   S   K   S   T   S   G   G   T   A   A   L   G   C
CTGGTCAAGGACTACTTCCCCGAACCGGTGACGGTGTCGTGGAACTCAGGCGCCCTGACC
 L   V   K   D   Y   F   P   E   P   V   T   V   S   W   N   S   G   A   L   T
AGCGGCGTGCACACCTTCCCGGCTGTCCTACAGTCCTCAGGACTCTACTCCCTCAGCAGC
 S   G   V   H   T   F   P   A   V   L   Q   S   S   G   L   Y   S   L   S   S
GTGGTGACCGTGCCCTCCAGCAGCTTGGGCACCCAGACCTACATCTGCAACGTGAATCAC
 V   V   T   V   P   S   S   S   L   G   T   Q   T   Y   I   C   N   V   N   H
AAGCCCAGCAACACCAAGGTGGACAAGAAAGTTGAGCCCAAATCTTGTGACAAAACTCAC
 K   P   S   N   T   K   V   D   K   K   V   E   P   K   S   C   D   K   T   H
ACATGCCCACCGTGCCCAGCACCTGAACTCCTGGGGGGACCGTCAGTCTTCCTCTTCCCC
 T   C   P   P   C   P   A   P   E   L   L   G   G   P   S   V   F   L   F   P
CCAAAACCCAAGGACACCCTCATGATCTCCCGGACCCCTGAGGTCACATGCGTGGTGGTG
 P   K   P   K   D   T   L   M   I   S   R   T   P   E   V   T   C   V   V   V
GACGTGAGCCACGAAGACCCTGAGGTCAAGTTCAACTGGTACGTGGACGGCGTGGAGGTG
 D   V   S   H   E   D   P   E   V   K   F   N   W   Y   V   D   G   V   E   V
CATAATGCCAAGACAAAGCCGCGGGAGGAGCAGTACAACAGCACGTACCGTGTGGTCAGC
 H   N   A   K   T   K   P   R   E   E   Q   Y   N   S   T   Y   R   V   V   S
GTCCTCACCGTCCTGCACCAGGACTGGCTGAATGGCAAGGAGTACAAGTGCAAGGTCTCC
 V   L   T   V   L   H   Q   D   W   L   N   G   K   E   Y   K   C   K   V   S
AACAAAGCCCTCCCAGCCCCCATCGAGAAAACCATCTCCAAAGCCAAAGGGCAGCCCCGA
 N   K   A   L   P   A   P   I   E   K   T   I   S   K   A   K   G   Q   P   R
GAACCACAGGTGTACACCCTGCCCCCATCCCGGGATGAGCTGACCAAGAACCAGGTCAGC
 E   P   Q   V   Y   T   L   P   P   S   R   D   E   L   T   K   N   Q   V   S
CTGACCTGCCTGGTCAAAGGCTTCTATCCCAGCGACATCGCCGTGGAGTGGGAGAGCAAT
 L   T   C   L   V   K   G   F   Y   P   S   D   I   A   V   E   W   E   S   N
GGGCAGCCGGAGAACAACTACAAGACCACGCCTCCCGTGCTGGACTCCGACGGCTCCTTC
 G   Q   P   E   N   N   Y   K   T   T   P   P   V   L   D   S   D   G   S   F
TTCCTCTACAGCAAGCTCACCGTGGACAAGAGCAGGTGGCAGCAGGGGAACGTCTTCTCA
 F   L   Y   S   K   L   T   V   D   K   S   R   W   Q   Q   G   N   V   F   S
TGCTCCGTGATGCATGAGGCTCTGCACAACCACTACACGCAGAAGAGCCTCTCCCTGTCT
 C   S   V   M   H   E   A   L   H   N   H   Y   T   Q   K   S   L   S   L   S
CCGGGTAAATGA
 P   G   K   *
```

FIG. 24

```
ATGAGGACCCCTGCTCAGTTTCTTGGAATCTTGTTGCTCTGGTTTCCAGGAATCAAATGT
 M   R   T   P   A   Q   F   L   G   I   L   L   L   W   F   P   G   I   K   C
GATATTGTGATGACCCAATCTCCACTCTCCCTGCCTGTCACTCCTGGAGAGCCAGCCTCC
 D   I   V   M   T   Q   S   P   L   S   L   P   V   T   P   G   E   P   A   S
ATCTCTTGCAGATCTAGTCAGAGCATTGTACATAGTAATGGAAACACCTATTTAGAATGG
 I   S   C   R   S   S   Q   S   I   V   H   S   N   G   N   T   Y   L   E   W
TACCTGCAGAAACCAGGCCAGTCTCCACAGCTCCTGATCTACAGAGTTTCCAACCGATTT
 Y   L   Q   K   P   G   Q   S   P   Q   L   L   I   Y   R   V   S   N   R   F
TCTGGGGTCCCAGACAGGTTCAGTGGCAGTGGATCAGGGACAGATTTCACACTCAAGATC
 S   G   V   P   D   R   F   S   G   S   G   S   G   T   D   F   T   L   K   I
AGCAGAGTGGAGGCTGAGGATGTCGGAGTTTATTACTGCTTTCAAGGTTCATTTGTTCCG
 S   R   V   E   A   E   D   V   G   V   Y   Y   C   F   Q   G   S   F   V   P
TGGACGTTCGGTCAAGGCACCAAAGTGGAAATCAAACGAACTGTGGCTGCACCATCTGTC
 W   T   F   G   Q   G   T   K   V   E   I   K   R   T   V   A   A   P   S   V
TTCATCTTCCCGCCATCTGATGAGCAGTTGAAATCTGGAACTGCCTCTGTTGTGTGCCTG
 F   I   F   P   P   S   D   E   Q   L   K   S   G   T   A   S   V   V   C   L
CTGAATAACTTCTATCCCAGAGAGGCCAAAGTACAGTGGAAGGTGGATAACGCCCTCCAA
 L   N   N   F   Y   P   R   E   A   K   V   Q   W   K   V   D   N   A   L   Q
TCGGGTAACTCCCAGGAGAGTGTCACAGAGCAGGACAGCAAGGACAGCACCTACAGCCTC
 S   G   N   S   Q   E   S   V   T   E   Q   D   S   K   D   S   T   Y   S   L
AGCAGCACCCTGACGCTGAGCAAAGCAGACTACGAGAAACACAAAGTCTACGCCTGCGAA
 S   S   T   L   T   L   S   K   A   D   Y   E   K   H   K   V   Y   A   C   E
GTCACCCATCAGGGCCTGAGCTCGCCCGTCACAAAGAGCTTCAACAGGGGAGAGTGTTAG
 V   T   H   Q   G   L   S   S   P   V   T   K   S   F   N   R   G   E   C   •
```

FIG. 25

```
ATGAGGACCCCTGCTCAGTTTCTTGGAATCTTGTTGCTCTGGTTTCCAGGAATCAAATGT
 M   R   T   P   A   Q   F   L   G   I   L   L   W   F   P   G   I   K   C
GATATCGTGATGACCCAATCTCCAGACTCCCTGGCTGTCAGTCTTGGAGAGAGGGCCACC
 D   I   V   M   T   Q   S   P   D   S   L   A   V   S   L   G   E   R   A   T
ATCTCTTGCAGATCTAGTCAGAGCATTGTACATAGTAATGGAAACACCTATTTAGAATGG
 I   S   C   R   S   S   Q   S   I   V   H   S   N   G   N   T   Y   L   E   W
TACCTGCAGAAACCAGGCCAGCCTCCAAAGCTCCTGATCTACAGAGTTTCCAACCGATTT
 Y   L   Q   K   P   G   Q   P   P   K   L   L   I   Y   R   V   S   N   R   F
TCTGGGGTCCCAGACAGGTTCAGTGGCAGTGGATCAGGGACAGATTTCACACTCACCATC
 S   G   V   P   D   R   F   S   G   S   G   S   G   T   D   F   T   L   T   I
AGCAGCCTGCAGGCTGAGGATGTGGCAGTTTATTACTGCTTTCAAGGTTCATTTGTTCCG
 S   S   L   Q   A   E   D   V   A   V   Y   Y   C   F   Q   G   S   F   V   P
TGGACGTTCGGTCAAGGCACCAAGGTGGAAATCAAACGAACTGTGGCTGCACCATCTGTC
 W   T   F   G   Q   G   T   K   V   E   I   K   R   T   V   A   A   P   S   V
TTCATCTTCCCGCCATCTGATGAGCAGTTGAAATCTGGAACTGCCTCTGTTGTGTGCCTG
 F   I   F   P   P   S   D   E   Q   L   K   S   G   T   A   S   V   V   C   L
CTGAATAACTTCTATCCCAGAGAGGCCAAAGTACAGTGGAAGGTGGATAACGCCCTCCAA
 L   N   N   F   Y   P   R   E   A   K   V   Q   W   K   V   D   N   A   L   Q
TCGGGTAACTCCCAGGAGAGTGTCACAGAGCAGGACAGCAAGGACAGCACCTACAGCCTC
 S   G   N   S   Q   E   S   V   T   E   Q   D   S   K   D   S   T   Y   S   L
AGCAGCACCCTGACGCTGAGCAAAGCAGACTACGAGAAACACAAAGTCTACGCCTGCGAA
 S   S   T   L   T   L   S   K   A   D   Y   E   K   H   K   V   Y   A   C   E
GTCACCCATCAGGGCCTGAGCTCGCCCGTCACAAAGAGCTTCAACAGGGGAGAGTGTTAG
 V   T   H   Q   G   L   S   S   P   V   T   K   S   F   N   R   G   E   C   *
```

HUMANIZED ANTIBODIES SPECIFIC FOR AMINO ACID SEQUENCE RGD OF AN EXTRACELLULAR MATRIX PROTEIN AND THE USES THEREOF

CROSS-REFERENCE TO RELATED APPLICATIONS

This application is a National Stage application of PCT/JP2010/067017, filed Sep. 22, 2010, which claims priority from U.S. Provisional Application No. 61/272,438, filed Sep. 24, 2009.

The instant application contains a Sequence Listing which has been submitted in ASCII format via EFS-WEB and is hereby incorporated by reference in its entirety. Said ASCII copy, created on Mar. 20, 2012, is named sequence.txt and is 62 KB.

1. FIELD OF THE INVENTION

Throughout this application, several references are referenced herein. Disclosure of these references in their entirety is hereby incorporated by reference into this application.

The present invention relates to humanized antibodies that immunospecifically recognize amino acid sequence RGD (Arg-Gly-Asp) of an extracellular matrix protein and to their therapeutic and diagnostic uses for various diseases or disorders including cancer, inflammatory diseases, autoimmune diseases, infectious disease, bone disease and the like.

2. BACKGROUND OF THE INVENTION

Cell adhesion plays an important role in sustaining life of multicellular organisms. Cell adhesions of multicellular organisms are classified into cell-extracellular matrix (hereinafter abbreviated as "ECM") adhesion and cell-cell adhesion. It has been elucidated that the cell-ECM adhesion is mediated by integrins and the cell-cell adhesion is mediated by cadherins, claudins and nectins.

Transmembrane adhesion proteins, such as integrins, constitute cell-ECM adhesions. It is reported that integrin forms heterodimer of α and β chains. At least 18 types of a chain, 8 types of β chain and 24 types of αβ heterodimer have been identified and confirmed so far. It is known that each type of α integrin recognizes a specific ligand. Transmembrane adhesion proteins including integrins relate to, in addition to cell adhesions, intracellular signal transductions from ECM into a cell and regulation of proliferation, mobility and differentiation (F. G Giancotti, et. al., *Science,* 285, 1028-1032, 1999).

Many proteins are known as ECM proteins which are classified into collagens (such as type I-XIX), non-collagenous glycoproteins (such as osteopontin (OPN), vitronectin, fibronectin, von Willebrand Factor, laminin, tenascin, fibrinogen, thrombospondin), elastins and proteoglycans. These ECM proteins bind to corresponding integrins and activate intracellular signal transduction pathways to regulate cytoskeletal organization, mobility, proliferation, differentiation, and the like. ECM protein-bound integrin regulates these signal activating pathways by transmitting specific signals depending on the type of ECM protein. It is appeared that the RGD (Arginine-Glycine-Asparagine acid) sequence is commonly observed in cell adhesion region of many ECM proteins and exhibits various functions by binding to integrins. It has been expected that the RGD sequence of ECM proteins can be a target of drugs, and a number of small molecule compounds and artificial peptides have been provided.

Some types of integrins such as α3β1 integrin, α5β1 integrin, α8β1 integrin, αvβ1 integrin, αvβ3 integrin, αvβ5 integrin, αvβ6 integrin, αvβ8 integrin have been known to bind to the RGD sequence. Interaction between α5β1 integrin and its specific ligand fibronectin has been revealed to investigate mechanisms of integrin-mediated signal transduction, and it is reported that α5β1 integrin regulates not only cell adhesion and cell mobility but also cell differentiation and cell mortality (S. M. Frisch et al., *Curr. Opin. Cell Biol.,* 9, 701-706, 1997). It also has been indicated that α5β1 integrin is highly expressed on tumor cells and relates to malignant alteration of cancer. Each integrin-mediated signal differs depending on binding ECM proteins. For example, stimulation by growth factor activates growth of fibronectin-bound endothelial cells, but inhibits growth of laminin-1-bound endothelial cells. Also, the signal transmitted from laminin-10/11 to α3β1 integrin is different from the signal transmitted from fibronectin to α5β1 integrin, and significantly enhances a mobility of cancerous cells (J. Gu et al., *J. Biol. Chem.,* 276, 27090-27097, 2001) and significantly avoids apoptosis by blood starvation (J. Gu et al., *J. Biol. Chem.,* 277, 19922-19928, 2002). High expression of RGD sequence binding av integrins has been observed in the osteoclastic cells and neovascular, and inhibition of the RGD sequence and the av integrins has been expected as a target for a therapeutic drug for osteoporosis and cancer. It has been indicated that α5β1 integrin is highly expressed on tumor cells and relates to malignant alteration of cancer. From these findings, anti-α5β1 integrin antibody (Volocimab), anti-α4 integrin antibody (Natalizumab), anti-αvβ3 integrin antibody (Vitaxin) have been developed as antagonistic anti-integrin antibody drugs which inhibit interaction between integrin and ECM protein.

Meanwhile, some ECM proteins such as collagen, osteopontin (OPN), vitronectin, fibronectin, von Willebrand Factor, laminin, tenascin, fibrinogen and thrombospondin have been known to include RGD sequence. Also, some virus and some bacterium have been known to possess RGD sequence to adhere to cells. OPN is an acidic glycoprotein with binding properties to calcium which is contained rich in bone. It is reported that OPN plays an important role in cell adhesion, cell migration, tumor formation, immune response and complement mediated cellular lysis. Outcomes of OPN knockout mice and anti-OPN neutralizing antibodies indicate that OPN relates to hepatitis, autoimmune disease such as rheumatoid arthritis and metastasis of cancer. Therefore, it is expected that an inhibitor of binding of ECM proteins to cells may be used for a treatment of osteoporosis or cancer. Thus, in addition to the above-mentioned antagonistic drugs targeted to integrins, antagonistic drugs targeted to the ECM proteins which are binding partner of the integrins have been developed.

3. SUMMARY OF THE INVENTION

Although drugs such as small molecules that inhibit the RGD sequence-mediated interaction with integrin, antibodies against OPN and antibodies against integrin have been developed, there is no reporting concerning an antibody which specifically recognizes the RGD sequence. Since the RGD sequence is one of the conserved sequences in ECM proteins, the antibody which specifically recognizes the RGD sequence is expected to have an effect in both of human and therapeutic model animals and thus is considered as a very useful active ingredient for the development of a therapeutic agent. Therefore, there has been a need for an antibody which specifically recognizes the RGD sequence. Previously, the inventors isolated mouse monoclonal antibodies that immunospecifically recognize the RGD sequence and are produced by hybridoma clones 33E10 and 35B6 (Depository Accession Nos. FERM BP-10440 and FERM BP-10441, respectively). Herein, the hybridoma clone designations are interchangeably used as the designations of the monoclonal antibodies produced by the clones. All of these mouse anti-RGD antibodies were of IgG1 isotype. These monoclonal antibodies was observed to interfere binding mediated by the RGD sequence between ECM and cell by binding to the RGD sequence of ECM proteins such as osteopontin. Thus, these anti-RGD antibodies are expected to exhibit therapeutic or diagnostic effects on the RGD sequence related disease such as cancer, e.g., the growth or metastasis of cancer cells, and on inflammatory diseases, e.g., rheumatoid arthritis, osteoarthritis, infectious disease, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, osteoporosis, and the like.

However, since these monoclonal antibodies are of mouse origin, possible adverse effects due to their immunogenicity in humans have hampered their direct applications to diagnostic or therapeutic uses in humans. To reduce the immunogenicity, the present inventors have prepared a humanized antibody that has biological activities corresponding to those exhibited by the original mouse anti-RGD antibody from which said humanized antibody was derived.

Accordingly, the present invention provides a humanized antibody or an antigen-binding fragment thereof, which immunospecifically recognizes the RGD sequence, said antibody comprising an antigen-binding region partially derived from a non-human origin and partially derived from a human origin. In an aspect of the present invention, the humanized antibody or the antigen-binding fragment thereof of the present invention comprises a complementarity determining region (hereinafter abbreviated as "CDR") derived from a non-human source (donor) such as 33E10 and 35B6 monoclonal antibodies, and a framework region (hereinafter abbreviated as "FR") derived from a human source (acceptor). Said humanized antibody or an antigen-binding fragment thereof may inhibit the binding between the RGD sequence and a ligand thereof.

In an aspect to the present invention, said humanized antibody or an antigen-binding fragment thereof that immunospecifically recognizes the RGD sequence comprises: (i) a heavy chain (hereinafter abbreviated as "H-chain") comprising at least one H-chain FR (hereinafter abbreviated as "FRH") derived from a variable region (hereinafter abbreviated as "V-region") of a human H-chain, and at least one H-chain CDR (hereinafter abbreviated as "CDRH") derived from at least one of the CDRHs of a non-human antibody that immunospecifically recognizes the RGD sequence; or (ii) a light chain (hereinafter abbreviated as "L-chain") comprising at least one L-chain FR (hereinafter abbreviated as "FRL") derived from a V-region of a human L-chain, and at least one L-chain CDR (hereinafter abbreviated as "CDRL") derived from at least one of the CDRLs of a non-human antibody that immunospecifically recognizes the RGD sequence; or both (i) and (ii) above.

In a preferred aspect of the present invention, the humanized antibody or an antigen-binding fragment thereof of the present invention comprises: (i) a H-chain comprising a VH, said VH comprising the amino acid sequence of SEQ ID NO: 92, 94 or 96; or (ii) a L-chain comprising a VL, said VL comprising the amino acid sequence of SEQ ID NO: 98 or 100; or (iii) both (i) and (ii) above. In another aspect of the present invention, said humanized antibody or an antigen-binding fragment thereof of the present invention comprises the amino acid sequence encoded by the nucleotide sequence of SEQ ID NO: 91, 92 or 93, and said VL comprises the amino acid sequence encoded by the nucleotide sequence of SEQ ID NO: 97 or 99.

In a preferred aspect of the present invention, said VH comprises the amino acid sequence encoded by the nucleotide sequence of SEQ ID NO: 91, 92 or 93, and said VL comprises the amino acid sequence encoded by the nucleotide sequence of SEQ ID NO: 97 or 99.

In another aspect of the present invention, said VH comprises the amino acid sequence of SEQ ID NO: 94 and said VL comprises the amino acid sequence of SEQ ID NO: 100.

In another aspect of the present invention, said H-chain comprises the amino acid sequence of SEQ ID NO: 25 or 27, and said L-chain comprises the amino acid sequence of SEQ ED NO: 29 or 31.

In a further aspect of the present invention, said H-chain comprises the amino acid sequence of SEQ ID NO: 25, and said L-chain comprises the amino acid sequence of SEQ ID NO: 31.

The present invention further provides a vector, e.g., an expression vector, comprising a nucleotide sequence encoding a H-chain or a L-chain, or both, of the humanized antibody or an antigen-binding fragment thereof of the present invention that immunospecifically recognizes the RGD sequence. In such a vector, the nucleotide sequence of the present invention may be operably linked to one or more regulatory elements. The nucleotide sequence of the present invention may include a nucleotide sequence encoding a signal peptide native to a non-human donor antibody from which a CDR is derived, or a signal peptide of heterologous origin.

Furthermore, the present invention provides a host cell comprising the nucleic acid molecule of the present invention, including a vector comprising the nucleic acid molecule of the present invention. In an aspect of the present invention, the present invention provides an isolated host cell comprising a first nucleic acid molecule encoding a humanized H-chain of the present invention and a second nucleic acid molecule encoding a humanized L-chain of the present invention, said first and second nucleic acid molecules are each operably linked to a regulatory element in such a way that the biologically functional humanized antibody or antigen-binding fragment thereof of the present invention is expressed.

The present invention further provides a method for preparing the humanized antibody or an antigen-binding fragment thereof of the present invention, comprising culturing the host cell of the invention under conditions so that the humanized antibody or an antigen-binding fragment thereof is expressed; and collecting the produced humanized antibody.

The present invention further provides a composition comprising at least one of the humanized antibodies or an antigen-binding fragment thereof of the present invention. In addition, the present invention provides a pharmaceutical composition for preventing or treating a disorder or disease that is associated with the RGD-proteins, comprising at least one of the humanized antibodies or an antigen-binding fragment thereof of the present invention, and a pharmaceutically acceptable carrier. Either of said compositions can further comprise another active compound that can additively or synergistically ameliorate the disorder or disease. Said active compounds include, but not limited to, anti-inflammatory compounds, chemotherapeutic compounds and the like. Said active compounds also include small molecule compounds and antibodies or an antigen-binding fragment thereof, such as human α4 integrin specific antibody or human α9 integrin specific antibody.

In another aspect, the present invention provides a method for preventing or treating a disorder or disease that is associated with or involves the RGD-proteins, said method comprising administering a prophylactically or therapeutically effective amount of at least one of the humanized antibodies or an antigen-binding fragment thereof of the present invention to a subject in need thereof. For such uses, the humanized antibody or an antigen-binding fragment thereof of the present invention may be conjugated to a therapeutic moiety that enhances the biological effect of the humanized antibody or an antigen-binding fragment thereof. Examples of such a therapeutic moiety include another antibody, cytotoxins that are cytostatic or cytocidal, radioactive elements, and/or other therapeutic agents, including anti-inflammatory agents, antibiotics and the like.

In yet another aspect, the present invention provides a method for diagnosing a disorder or disease, in a subject, that is associated with or involves RGD-proteins, said method comprising administering a diagnostically effective amount of the humanized antibody or an antigen-binding fragment thereof of the present invention to a subject to be examined. For such diagnostic uses, the humanized antibody of the present invention may be labeled with detectable markers, such as radioactive elements.

3.1. Definitions

As used herein, the term "antibody" refers to an antibody molecule capable of immunospecifically binding to a desired antigen or desired sequence such as the RGD sequence, which encompass an antibody molecule as a whole and may encompass a fragment of the antibody including an antigen-binding fragment of the antibody.

The term "an antigen-binding fragment" used herein refers to any fragment of an antibody that retains an ability to immunospecifically bind to a target polypeptide, protein or sequence, in particular the RGD sequence, which includes single chain antibodies, Fab fragments, F(ab')$_2$ fragments, disulfide-linked Fvs and fragments containing either a VL and/or a VH or a CDR that specifically binds to a target polypeptide, protein or sequence. Thus, such antigen-binding fragments of humanized antibody may or may not include partial or full-length human constant regions. Various methods for obtaining the antibody fragments described above are well known in the art.

The term "immunospecifically recognize" used herein refers to an ability of an antibody or an antigen-binding fragment thereof to bind specifically to a target polypeptide, protein or sequence, in particular, human RGD sequence. Such an antibody does not non-specifically bind to other polypeptides or proteins. However, an antibody or an antigen-binding fragment thereof that immunospecifically binds to the target polypeptide or protein (e.g., RGD-protein) may cross-react with other antigens. For example, the humanized antibody or an antigen-binding fragment thereof of the present invention that immunospecifically recognizes human RGD-proteins may cross-react with murine RGD-proteins. Preferably, an antibody or an antigen-binding fragment thereof that immunospecifically recognizes RGD-proteins does not cross-react with other antigens.

The term "derived from a human source" or "derived from a non-human source" used herein refers to an antibody portion whose amino acid sequence is derived from a corresponding portion of a human antibody or of a non-human antibody, respectively.

The term "an acceptor sequence" used herein refers to a nucleotide sequence or an amino acid sequence of FRs from a human antibody VH or VL that serves as an acceptor for CDRs from a donor antibody which is usually a non-human antibody.

4. BRIEF DESCRIPTION OF THE FIGURES

For the purpose of illustrating the present invention, FIGS. 1-27 reflect a form which is presently preferred; it being understood however, that the invention is not limited to the precise form shown in FIGS. 1-27 in which:

FIG. 1 shows the nucleotide sequence of mouse 33E10 VH cDNA is shown along with the deduced amino acid sequence. Amino acid residues are shown in single letter code. The signal peptide sequence is in italic. The N-terminal amino acid residue (E) of the mature VH is double-underlined. CDR sequences according to the definition of Kabat et al. (Sequences of Proteins of Immunological Interests, Fifth edition, NIH Publication No. 91-3242, U.S. Department of Health and Human Services, 1991) are underlined.

FIG. 2 shows the nucleotide sequence of mouse 33E10 VL cDNA is shown along with the deduced amino acid sequence. Amino acid residues are shown in single letter code. The signal peptide sequence is in italic. The N-terminal amino acid residue (D) of the mature VL is double-underlined. CDR sequences according to the definition of Kabat et al. (1991) are underlined.

FIG. 3 shows the nucleotide sequence of the designed 33E10 VH gene flanked by SpeI and HindIII sites (underlined) is shown along with the deduced amino acid sequence. Amino acid residues are shown in single letter code. The signal peptide sequence is in italic. The N-terminal amino acid residue (E) of the mature VH is double-underlined. CDR sequences according to the definition of Kabat et al. (1991) are underlined. The intron sequence is in italic.

FIG. 4 shows the nucleotide sequence of the designed 33E10 VL gene flanked by NheI and EcoRI sites (underlined) is shown along with the deduced amino acid sequence. Amino acid residues are shown in single letter code. The signal peptide sequence is in italic. The N-terminal amino acid residue (D) of the mature VL is double-underlined. CDR sequences according to the definition of Kabat et al. (1991) are underlined. The intron sequence is in italic.

FIG. 5 shows schematic structure of the expression vectors for chimeric and humanized 33E10 antibodies (collectively, "Expression Vector"). Proceeding clockwise from the SalI site at the top, the plasmid contains the heavy chain transcription unit starting with the human cytomegalovirus (CMV) major immediate early promoter and enhancer (CMV promoter) to initiate transcription of the antibody heavy chain gene. The CMV promoter is followed by the VH exon, a genomic sequence containing the human gamma-1 heavy chain constant region including the CH1, hinge, CH2 and CH3 exons with the intervening introns, and the polyadenylation site following the CH3 exon. After the heavy chain gene sequence, the light chain transcription unit begins with the CMV promoter, followed by the VL exon and a genomic sequence containing the human kappa chain constant region exon (CL) with part of the intron preceding it, and the polyadenylation site following the CL exon. The light chain gene is then followed by the SV40 early promoter (SV40 promoter), the *E. coli* xanthine guanine phosphoribosyl transferase gene (gpt), and a segment containing the SV40 polyadenylation site (SV40 poly(A) site). Finally, the plasmid contains a part of the plasmid pUC19, comprising the bacterial origin of replication (pUC ori) and beta-lactamase gene (beta lactamase). Locations of relevant restriction enzyme sites are shown in this Figure.

FIG. 6 shows the alignment of the amino acid sequences of 33E10 VH, humanized 33E10 (Hu33E10) VH and human acceptor U03400 (GenBank accession number) is shown. Amino acid residues are shown in single letter code. Numbers above the sequences indicate the positions according to Kabat et al. (1991). CDR sequences defined by Kabat et al. (Sequences of Proteins of Immunological Interests, Fifth edition, NIH Publication No. 91-3242, U.S. Department of Health and Human Services, 1991) are underlined. Double-underlined residues were predicted to contact with the CDRs and the mouse residues were retained at these locations in the humanized form. CDR residues in UO3400 are omitted in this Figure.

FIG. 7 shows the alignment of the amino acid sequences of 33E10 VL, humanized 33E10 (Hu33E10) VL and human acceptor X72452 (GenBank accession number) is shown. Amino acid residues are shown in single letter code. Numbers above the sequences indicate the positions according to Kabat et al. (1991). CDR sequences defined by Kabat et al. (1991) are underlined. CDR residues in X72452 are omitted in this Figure.

FIG. 8 shows oligonucleotides used for construction of the Hu33E10 VH1 gene.

FIG. 9 shows the oligonucleotides used for construction of the Hu33E10 VL1 gene.

FIG. 10 shows the oligonucleotides used for construction of the Hu33E10 VH1 gene. An arrow denotes the position and orientation (5' to 3') of each oligonucleotide. Amino acid residues are shown in single letter code.

FIG. 11 shows oligonucleotides used for construction of the Hu33E10 VL1 gene. An arrow denotes the position and orientation (5' to 3') of each oligonucleotide. Amino acid residues are shown in single letter code.

FIG. 12 shows the nucleotide sequence of the Hu33E10 VH1 gene flanked by SpeI and HindIII sites (underlined) is shown along with the deduced amino acid sequence. Amino acid residues are shown in single letter code. The signal peptide sequence is in italic. The N-terminal amino acid residue (E) of the mature VH is double-underlined. CDR sequences according to the definition of Kabat et al. (1991) are underlined. The intron sequence is in italic.

FIG. 13 shows the nucleotide sequence of the Hu33E10 VL1 gene flanked by NheI and EcoRI sites (underlined) is shown along with the deduced amino acid sequence. Amino acid residues are shown in single letter code. The signal peptide sequence is in italic. The N-terminal amino acid residue (D) of the mature VL is double-underlined. CDR sequences according to the definition of Kabat et al. (1991) are underlined. The intron sequence is in italic.

FIG. 14 shows the nucleotide sequence of the Hu33E10 VL6 gene flanked by NheI and EcoRI sites (underlined) is shown along with the deduced amino acid sequence. The silent mutation to eliminate the splicing donor site in the signal peptide-coding region is double-underlined. Amino acid residues are shown in single letter code. The signal peptide sequence is in italic. The N-terminal amino acid residue (D) of the mature VL is double-underlined. CDR sequences according to the definition of Kabat et al. (1991) are underlined. The intron sequence is in italic.

Figure 15A:
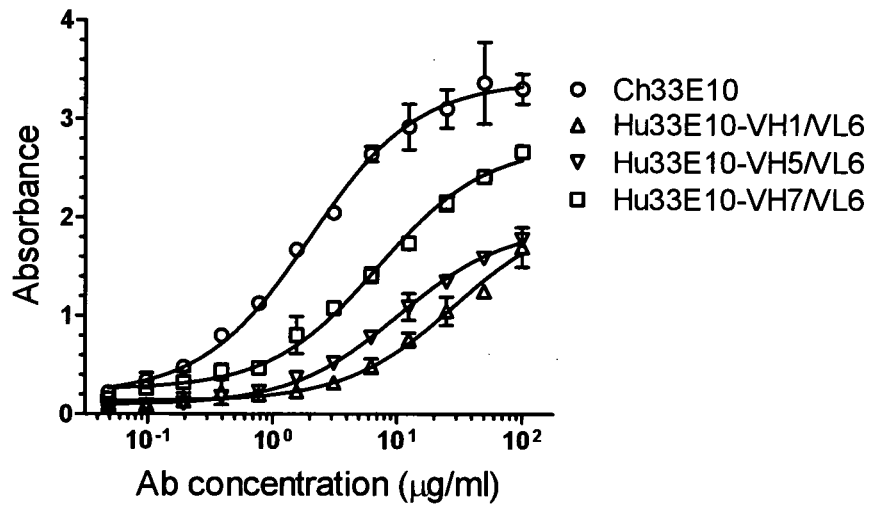
Figure 15B:
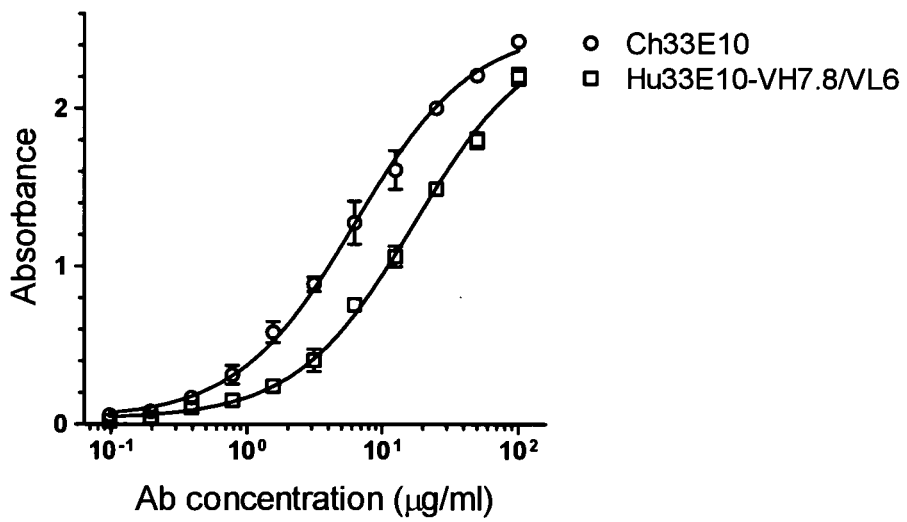

FIGS. 15A & 15B show ELISA analysis of the binding of chimeric and humanized 33E10 IgG1/κ antibodies to hOPN5-BSA. Purified Ch33E10, Hu33E10-VH1/VL6, Hu33E10-VH5/VL6 and Hu33E10-VH7/VL6 (FIG. 15A) and Ch33E10 and Hu33E10-VH7.8/VL6 (FIG. 15B) were tested at various concentrations, starting at 100 μg/ml and serial 2-fold dilutions, for binding to hOPN5-BSA. Experiments were carried out in duplicate.

FIG. 16 shows the nucleotide sequence of the Hu33E10 VH5 gene flanked by SpeI and HindIII sites (underlined) is shown along with the deduced amino acid sequence. Amino acid residues are shown in single letter code. The signal peptide sequence is in italic. CDR sequences according to the definition of Kabat et al. (1991) are underlined. The intron sequence is in italic. The double-underlined amino acid residue indicates difference from VH1.

FIG. 17 shows the nucleotide sequence of the Hu33E10 VH7 gene flanked by SpeI and HindIII sites (underlined) is shown along with the deduced amino acid sequence. Amino acid residues are shown in single letter code. The signal peptide sequence is in italic. CDR sequences according to the definition of Kabat et al. (1991) are underlined. The intron sequence is in italic. Double-underlined amino acid residues indicate difference from VH1.

FIG. 18 shows nucleotide sequence of the Hu33E10 VH7.8 gene flanked by SpeI and HindIII sites (underlined) is shown along with the deduced amino acid sequence. Amino acid residues are shown in single letter code. The signal peptide sequence is in italic. CDR sequences according to the definition of Kabat et al. (1991) are underlined. The intron sequence is in italic. Double-underlined amino acid residues indicate difference from VH1.

FIG. 19 shows the alignment of the amino acid sequences of 33E10 VL, Hu33E10 VLv2 and human acceptor M29467 (GenBank accession number) is shown. Amino acid residues are shown in single letter code. Numbers above the sequences indicate the positions according to Kabat et al. (1991). CDR sequences defined by Kabat et al. (1991) are underlined. Double-underlined residues were predicted to contact with the CDRs and the mouse residues were retained at these locations in the humanized form. CDR residues in M29467 are omitted in this Figure.

FIG. 20 shows the nucleotide sequence of the Hu33E10 VLv2 gene flanked by NheI and EcoRI sites (underlined) is shown along with the deduced amino acid sequence. Amino acid residues are shown in single letter code. The signal peptide sequence is in italic. The N-terminal amino acid residue (D) of the mature VL is double-underlined. CDR sequences according to the definition of Kabat et al. (1991) are underlined. The intron sequence is in italic.

Figure 21A:
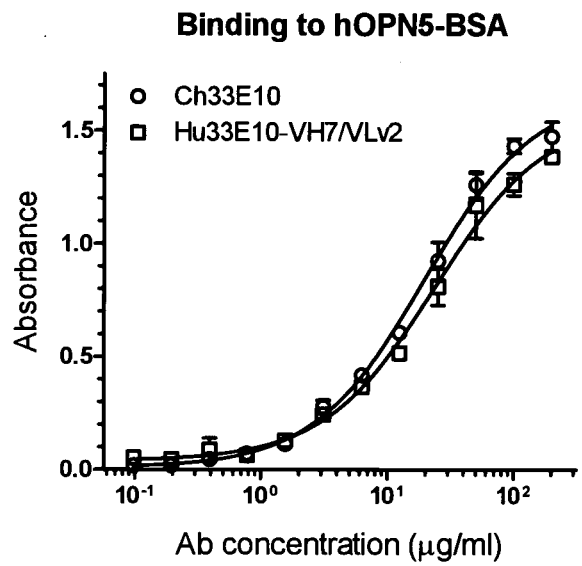
Figure 21B:
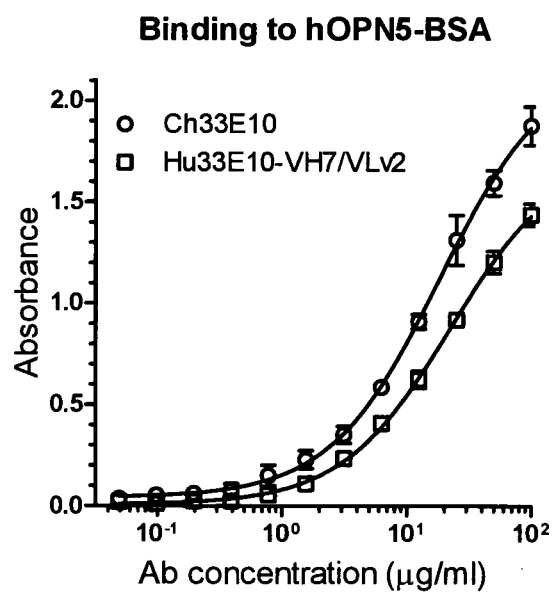

FIGS. 21A & 21B show ELISA analysis of the binding of Ch33E10 and Hu33E10-VH7/VLv2 IgG1/κ antibodies to hOPN5-BSA. Purified Ch33E10 and Hu33E10-VH7/VLv2 antibodies were tested at various concentrations, starting at 200 μg/ml (FIG. 21A) or 100 μg/ml (FIG. 21B) and serial 2-fold dilutions, for binding to hOPN5-BSA. The results of two independent experiments in duplicate (FIGS. 21A & 21B) are shown.

FIG. 22 shows the sequences of oligonucleotides used for PCR amplification and sequencing of Hu33E10 heavy and light chain cDNA.

FIG. 23 shows the nucleotide sequence of the coding region for VH7 and gamma-1 heavy chain constant regions expressed in NS0-Hu33E10-4 and NS0-Hu33E10-6 is shown along with the deduced amino acid sequence. Amino acid residues are shown in single letter code. A termination codon is denoted by "•".

FIG. 24 shows the nucleotide sequence of the coding region for VH7.8 and gamma-1 heavy chain constant regions expressed in NS0-Hu33E10-5 is shown along with the deduced amino acid sequence. Amino acid residues are shown in single letter code. A termination codon is denoted by "•".

FIG. 25 shows the nucleotide sequence of the coding region for VL6 and kappa light chain constant regions expressed in NS0-Hu33E10-4 and NS0-Hu33E10-5 is shown along with the deduced amino acid sequence. Amino acid residues are shown in single letter code. A termination codon is denoted by "•".

FIG. 26 shows the nucleotide sequence of the coding region for VLv2 and kappa light chain constant regions expressed in NS0-Hu33E10-6 is shown along with the deduced amino acid sequence. Amino acid residues are shown in single letter code. A termination codon is denoted by "•".

Figure 27:
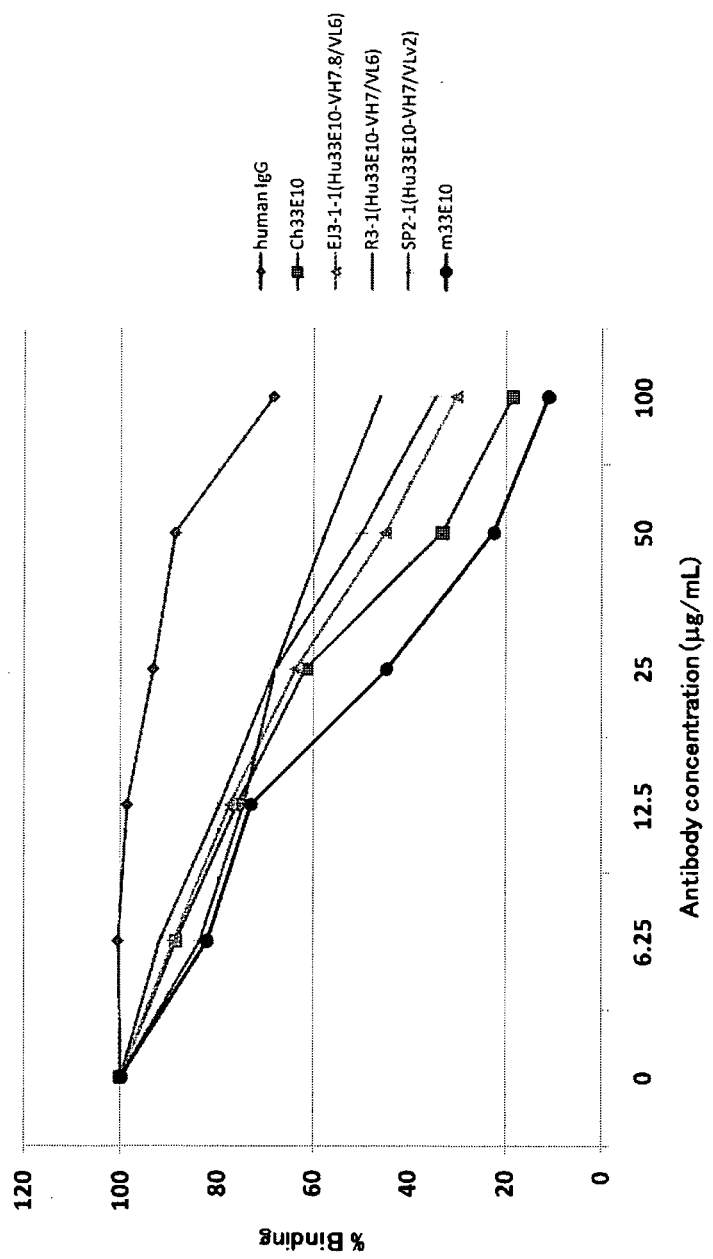

FIG. 27 shows the humanized anti-OPN antibodies inhibited the adhesion of MDA-MB-435S to hOPN5-BSA. MDA-MB-435S (4×104 cell/well) was allowed to adhere to 96-well plates pre-coated with hOPN5-BSA (2 mg/ml) in the presence of various concentration of antibodies, human IgG, Ch33E10, EJ3-1-1 (Hu33E10-VH7.8/VL6), R3-1 (Hu33E10-VH7/VL6), SP2-1 (Hu33E10-VH7/VLv2), and m33E10. Data is presented at as a mean of triplicate experiments.

5. DETAILED DESCRIPTION OF THE INVENTION

5.1 Preparation of Antibodies Against the RGD sequence

Antibodies that immunospecifically recognize the RGD sequence may be generated by any suitable method known in the art.

RGD-protein or peptides which includes cell adhesive "RGD" sequence (hereinafter abbreviated as "RGD-peptides") in the present invention or may be (1) derived from human ECMs that express RGD-protein or from all tissues where these ECMs are present, (2) recombinant proteins or peptides which are obtained by expression of the DNA (preferably cDNA) encoding the RGD-protein or RGD-peptide by transfecting into bacteria, yeast, cell lines such as animal cells, etc., or (3) synthetic proteins or peptides.

The RGD-peptides used as an antigen in the present invention may be able to produce antibodies against the RGD sequence by immunization. The RGD-peptides include the RGD-peptides an amino acid sequence CVDVPNG RGDSLAYGLR (SEQ ID NO:71) which is a cell adhesive sequence of murine ECM protein. The RGD-proteins or the RGD-peptides include such as OPN, vitronectin, fibronectin, von Willebrand Factor, collagens, laminin, tenascin, fibrinogen, thrombospondin and RGD including fragment thereof. Artificial or natural variations such as substitutions, deletions, modifications and additions of the amino acid can be applied to the said proteins or said peptides as far as the proteins or the peptides include the RGD-sequence. The variant proteins or peptides may comprise an amino acid sequence, wherein multiple amino acids, preferably 1 to 10 amino acids and more preferably 1 to several (e.g., 1 to 5) amino acids are substituted deleted, modified, added or inserted.

Herein, the RGD-peptide comprises at least about 5 amino acids, preferably about 5 to 50 amino acids, and more preferably about 10 to 20 amino acids. The RGD-proteins or the RGD-peptides as an antigen in the present invention can be produced by using methods well known in the art, such as chemical synthesis method, cell culture method, gene recombinant method and its proper modification. For example, the RGD-peptide can be obtained by cleaving ECM protein with protease appropriately. The RGD-protein or the RGD-peptide can be derived from mammal such as murine, rat, rabbit, swine, bovine, monkey and human. Any methods well known in the art can be used for preparing the RGD-protein or the RGD-peptide which can be used for preparing an anti-RGD antibody.

Examples of the methods for producing variant polypeptides include a synthetic oligonucleotide site-directed mutagenesis (gapped duplex method), a point mutagenesis method which involves introducing a point mutation at random by treatment with nitrite or sulfite, a method which involves preparing a deletion mutant with Bal31 enzyme, or other enzymes, a cassette mutagenesis, a linker scanning method, a miss incorporation method, a mismatch primer method, a DNA segment synthesis method, and the like.

The RGD-peptide can be bound with other biologic macromolecule such as thyrogloblin, Keyhole Limpet Haemocyanin (KLH), bovine serum albumin (BSA), ovalbumin (OVA) or bovine globulin, preferably thyrogloblin. The method for binding RGD-peptide to a biologic macromolecule may be achieved by using coupling reagent such as a binding reagent having active ester group and maleic imide group (the active ester group binds to amino group of a protein or a peptide and the maleic imide group binds to thiol group of a protein or a peptide; S. yoshirake et al., Eur. J. Biochem., 101, 395-399, 1979), by using mixed anhydride method (B. F. Erlanger et al., J. Biol. Chem., 234, 1090-1094, 1954), or by using active ester method (A. E. Karu et al., J. Agric. Food Chem., 42, 301-309, 1994). The method for binding RGD-peptide to a biologic macromolecule is preferably achieved by using coupling reagent.

As an antigen, a cell per se that overexpresses the RGD-protein or the RGD-peptide can be also used. Cells overexpressing the RGD-protein or the RGD-peptide may be prepared by recombinant DNA technologies well known in the art.

Using appropriate antigens prepared as described above, antibodies specific for the RGD sequence may be prepared by various methods well known in the art. Polyclonal antibodies to the RGD sequence can be produced by various procedures well known in the art. For example, an antigen of interest can be administered to various host animals including, but not limited to, rabbits, mice, rats, etc., to induce the production of antisera containing polyclonal antibodies specific for the antigen. Various adjuvants may be used to increase the immunological response, depending on the host species, which include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*. Such adjuvants are also well known in the art.

Monoclonal antibodies can be prepared by using a wide variety of techniques known in the art including the use of hybridoma, recombinant and phage display technologies, or a combination thereof. For example, monoclonal antibodies can be produced by using hybridoma techniques including those known in the art and taught in, for example, Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody derived from a single clone, and includes any eukaryotic, prokaryotic or phage clone, but not limited to the method it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells (e.g., P3U1, P3×63-Ag8, P3×63-Ag8-U1, P3NS1-Ag4, SP2/0-Ag14, P3×63-Ag8-653, etc.). Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments what recognize specific epitopes may be generated by known techniques. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the complete L-chain, and the V-region, the CH1 region and the hinge region of the H-chain.

The antibodies of the invention or an antigen-binding fragment thereof may be produced by any method known in the art for synthesis of antibodies, in particular, by chemical synthesis or preferably by recombinant expression techniques.

The nucleotide sequence encoding an antibody may be obtained from any information available to those skilled in the art (i.e., from Genbank, the literature, or by routine cloning and sequence analysis). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from any tissue or cells expressing the antibody, such as hybridoma cells selected to express an antibody) by PCR amplification using synthetic primers hybridizable to the and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

5.2 Preparation of Recombinant Antibodies

The nucleotide sequence of the antibody may be manipulated by using methods well known in the art for the manipulation of nucleotide sequences, e.g., recombinant DNA techniques, site directed mutagenesis, PCR and the like (see, for example, the techniques described in Sambrook et al., supra; and Ausubel et al., eds., 1998, Current Protocols in Molecular Biology, John Wiley & Sons, NY, which are both incorporated by reference herein in their entireties). Antibodies may be introduced mutations such as substitutions, deletions and/or insertions of amino acid at epitope-binding domain regions or at any portion to enhance or reduce biological activities.

An expression vector containing a nucleotide sequence that encodes the antibody can be used for recombinant expression of an antibody or an antigen-binding fragment thereof. The vector including a nucleotide sequence encoding an antibody molecule, a H-chain and/or a L-chain of an antibody or a portion thereof for production of the antibody or an antigen-binding fragment thereof may be produced by recombinant DNA technology using techniques well known in the art as discussed in the previous sections. Methods which are well known to those skilled in the art can be used to construct expression vectors containing antibody or an antigen-binding fragment thereof coding sequences and appropriate transcriptional and translational control signals. These methods include, for example, in vitro recombinant DNA techniques, synthetic techniques, and in vivo genetic recombination. The nucleotide sequence encoding the VH, the VL, both of the VH and the VL, an antigen-binding fragment of the VH and/or VL, or one or more CDRs of an antibody may be cloned into such a vector for expression. Such a sequence may be fused with a polynucleotide encoding a signal peptide which may be native or a heterologous to the original antibody. The expression vector thus-prepared can be then introduced into appropriate host cells for the expression of the antibody. Accordingly, the invention includes host cells containing a polynucleotide encoding a humanized antibody or an antigen-binding fragment thereof that immunospecifically recognizes the RGD sequence.

The host cell may be co-transfected with two expression vectors of the invention, wherein the first vector encodes a H-chain derived polypeptide and the second vector encodes a L-chain derived polypeptide. The two vectors may contain identical selectable markers which enable equal expression of H-chain and L-chain polypeptides or different selectable markers to ensure maintenance of both plasmids. Alternatively, a single vector may be used which encodes, and is capable of expressing, both of H-chain and L-chain polypeptides. The coding sequences for the H-chain and L-chain may comprise cDNA or genomic DNA.

In another aspect of the present invention, antibodies can also be generated using various phage display methods known in the art. In phage display methods, functional antibody domains are displayed on the surface of phage particles which carry the polynucleotide sequences encoding them. In a particular aspect of the present invention, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phages used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., J. Immunol. Methods, 182:41-50, 1995; Ames et al., J. Immunol. Methods, 184:177-186, 1995; Kettleborough et al., Eur. J. Immunol., 24:952-958, 1994; Persic et al., Gene, 187:9-18, 1997; Burton et al., Advances in Immunology, 57:191-280, 1994; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717;

5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab)2 fragments can also be employed using methods known in the art such as those disclosed in PCT publication WO 92/22324; Mullinax et al., BioTechniques, 12(6):864-869, 1992; and Sawai et al., AJRI, 34:26-34, 1995; and Better et al., Science, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., Methods in Enzymology, 203:46-88, 1991; Shu et al., PNAS, 90:7995-7999, 1993; and Skerra et al., Science, 240:1038-1040, 1988.

Once an antibody molecule of the invention has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

For some uses, including in vivo use of antibodies in humans and in vitro detection assays, it may be preferable to use chimeric, humanized, or human antibodies. Chimeric antibodies and humanized antibodies are discussed in details in Section 5.3, infra.

Antibodies fused or conjugated to other compounds or heterologous polypeptides may be used in in vitro immunoassays, in purification methods (e.g., affinity chromatography), as well as in vivo therapeutic or diagnostic uses. See e.g., PCT publication Number WO 93/21232; EP 439,095; Naramura et al., *Immunol. Lett.*, 39:91-99, 1994; U.S. Pat. No. 5,474,981; Gillies et al., *PNAS*, 89:1428-1432, 1992; and Fell et al., *J. Immunol.*, 146:2446-2452, 1991, which are incorporated herein by reference in their entireties. For example, antibodies can be labeled in various ways using a known method or commercially available kit (e.g., biotin labeling, FITC labeling, APC labeling). As another example, antibodies may be conjugated to a therapeutic moiety that enhances the biological effect of the antibodies in vivo. Examples of such a therapeutic moiety include another antibody, cytotoxins that are cytostatic or cytocidal, radioactive element, and/or other therapeutic agents, including anti-inflammatory agents, antibiotics, and the like. In the present invention, the humanized anti-RGD antibody may be conjugated to another antibody to form a bispecific antibody. As another example, the humanized antibody of the present invention may be labeled with detectable markers, such as radioactive elements, for in vivo diagnostic uses.

5.3 Chimeric and Humanized Antibodies

A chimeric antibody is a molecule in which different portions of the antibody are derived from different animal species, such as antibodies having a V-region derived from a murine monoclonal antibody and a constant region derived from a human immunoglobulin. Methods for producing chimeric antibodies are known in the art. See, e.g., Morrison, Science, 229:1202, 1985; Oi et al., BioTechniques, 4:214 1986; Gillies et al., J. Immunol. Methods, 125:191-202, 1989; U.S. Pat. Nos. 5,807,715; 4,816,567; and 4,816,397, which are incorporated herein by reference in their entireties.

A humanized antibody is a molecule that binds a desired antigen and comprises a V-region containing one or more CDRs derived from a non-human species and one or more FRs derived from a human immunoglobulin molecule. The typical methods for humanizing non-human antibodies have been described in various references, such as those: by Queen et al., 1989, *Proc. Natl. Acad. Sci. USA* 86:10029-10033 and U.S. Pat. Nos. 5,585,089 and 5,693,762; by Riechmann et al., *Nature*, 332:323, 1988; and by Tsurushita et al., *Methods* 36:69-83, 2005, all of which are incorporated herein by reference in their entireties). For example, the reference by Tsurushita et al. (2005, supra; hereafter "Tsurushita") provides a practical and instructive protocol for the humanization of mouse monoclonal antibodies based on the antibody-humanization method originally developed by Queen et al. (1989, supra). The general protocol disclosed in Tsurushita is briefly summarized below.

5.3.1 General Protocol for Preparing Humanized Antibodies

Cloning and Sequencing of Mouse V Genes

Various methods are available for cloning cDNAs encoding the VH and the VL of a target mouse monoclonal antibody. For example, 5' RACE (rapid amplification of cDNA ends) method using SMART RACE cDNA Amplification Kit (BD Biosciences, CA) or the GeneRacer Kit (Invitrogen, CA) has been commonly used. A gene-specific primer for 5' RACE can be prepared based on the isotypes of the H-chain and the L-chain of the target monoclonal antibody so that it can bind immediately downstream of the VH and VL. Thus, 5' RACE primer may be designed to be specific for each subtype in mouse, such as $\gamma 1$, $\gamma 2a$, $\gamma 2b$ or $\gamma 3$. Alternatively, a common primer for all subtypes may be designed based on the consensus or highly homologous region among the subtypes. In Tsurushita, the following 5' RACE primers are disclosed as examples:

```
(i)
                                          (SEQ ID NO: 82)
5'-GCCAGTGGATAGACTGATGG-
(for cloning of mouse γ1, γ2a, γ2b and γ3
H-chains)

(ii)
                                          (SEQ ID NO: 83)
5'-GATGGATACAGTTGGTGCAGC-
(for cloning of mouse κ L-chains).
```

PCR-amplified V-region gene fragments can be directly cloned into a plasmid vector, for example, using the Zero Blunt TOPO PCR Cloning Kit (Invitrogen), and their DNA sequences determined. The obtained sequences should be confirmed by, for example, comparing their encoding amino acid sequences with those of the target monoclonal antibody determined by the N-terminal amino acid sequencing, using, for example a Model 241 Protein Sequencer (Hewlett-Packard, CA). Typically, the determination of at least 15-20 amino acid residues at the N-terminus of the target antibody, for example, by Edman degradation, is sufficient to confirm the authenticity of the cloned DNA sequences. Tsurushita cautions that when glutamine, which is one of the two most common N-terminal amino acid in mouse, is the N-terminal amino acid, it might have been converted to pyroglutamine and blocks the sequencing at the N-terminus. In that case, it is necessary to deblock the N-terminus to obtain the sequence.

Three-Dimensional Modeling of V-Regions

Based on the sequences of the VH and the VL, the framework residues of the target antibody that are potentially important for maintaining the conformational structure of the CDRs, are first identified by the method, for example, described by R. Levy et al., 1989, *Biochemistry* 28:7168-7175; and by B. Zilber et al., 1990, *Biochemistry* 29:10032-10041. Typically, each of the VH and VL is divided into 14 structurally meaningful segments, which are β strands and loop-like structures comprising the domain structure of the immunoglobulin superfamily. The amino acid sequence of each of the segments from the target antibody is aligned with the corresponding segments of antibodies of known structures, in the PDB database (see H. M. Berman et al., 2000, *Nucleic Acids Res.* 28:235-342). By multiple sequence alignment, a corresponding segment having the highest sequence homology to each of the target segment is selected and the three-dimensional model of the V-region is constructed. In order to optimize the structure, the model is subjected to multiple cycles of conjugate gradient energy minimization (e.g., using ENCAD, or as described by Press et al., 1990, in "*Numerical Recipes*, Cambridge University Press, Cambridge; AMBER by Weiner et al., 1981, *J. Comp. Chem.* 2:287-303; 3D-JIG-SAW available at BioMolecularModelling or "BMM" web site run by Cancer Research UK; or SWISS-MODEL available at ExPASy Proteomics Server web site run by Swiss Institute of Bioinformatics, Geneva).

Selection of Human Frameworks

In parallel with modeling the structure of the V-regions, the amino acid sequences deduced from the cDNA cloning of the mouse VH and VL, respectively, are compared to human V-region sequences in the databases, for example, the Kabat database (see Johnson et al., 2000, *Nucleic Acids Res.* 28:214-218.), GenBank, and so forth. Human FRs that have overall sequence identity of at least about 65%, at least about 70%, at least about 75%, at least about 80%, at least about 85%, at least about 90%, or at least 95% identity, with the mouse sequence, can be searched using, for example, the Smith-Waterman algorithm (by Gusfield, 1997, in "*Algorithms on Strings, Trees, and Sequences*", Cambridge University Press, Cambridge), or BLAST (by Karlin et al., 1990, *Proc. Natl. Acad. Sci. USA* 87:2264-2268), and the like. These human sequences may be based on cDNA-based and protein-derived sequences; however, the use of germline is often preferable as it may be useful in eliminating potential immunogenicity associated with somatic hypermutations in cDNA-based, protein-derived sequences. In the alternative, as described in Queen et al. (1989, supra), the use of a consensus framework sequence can also identify and remove such hypermutated residues in the framework obtained from cDNA-based or protein-derived sequences. In the case where a germline VH segment is used as an acceptor framework, VH segments encoded on chromosome 14, rather than 15 and 16, should be used as only those on chromosome 14 produce functional VH.

Design of Humanized V-Regions

According to Queen et al. (1989, supra), it is necessary to identify framework amino acids within about 4-6 Å of the CDRs as these residues are considered to be potential key framework residues that support the correct CDR structures. Such a process can be achieved using a computer program, such as RASMOL available at Molecular Visualization Freeware web site supported by National Science Foundation (NSF), that calculates interatomic distances from the atomic coordinates or, through manual inspection of a computer model. If amino acids at key framework positions are different between mouse donor and human acceptor sequences, those of mouse donor usually replace the human residues. However, if such residues have minimal contribution to support the CDR structures, the corresponding human residues are typically used. Also, if the selected human acceptor contains "atypical" amino acids, which occur in less than about 10-20% of the V region sequences, they may be the result of somatic hypermutation during affinity maturation and should be replaced with the donor residues in order to avoid potential immunogenicity in humans.

In addition, other factors, such as residues of potential N-linked glycosylation signals, need to be carefully considered in order to design humanized V regions (see Tsurushita for details).

Humanized antibodies may contain a human constant region or a portion thereof from the human κ or λ L-chain, and/or the γ1, γ2, γ3, γ4, μ, α1, α2, δ, or ε H-chain of human antibodies, or variants thereof, depending on the effector functions required or to be eliminated for therapeutic uses. For example, a Fc portion of the constant region containing a mutation may be fused to the V-region of the chimeric or humanized antibody of the present invention so as to reduce the binding of the antibody to Fc receptors and/or to reduce its ability to fix complement (see, for example, Winter et al., GB 2,209,757 B; Morrison et al., WO 89/07142, Morgan et al., WO 94/29351). Such manipulations of antibody molecules can be carried out by recombinant DNA technology as described in Section 5.2.

Preferably the resulting chimeric or humanized antibody has the same specificity as the non-human donor antibody and an affinity similar to or at least about ⅓, at least about ½, or at least about ⅔, of that of the non-human donor antibody. In another aspect, the resulting chimeric or humanized antibody has an affinity constant of at least about $1 \times 10^7 M^{-1}$, preferably at least about $1 \times 10^8 M^{-1}$, and most preferably at least about $1 \times 10^9 M^{-1}$.

In addition to the general protocol described above, antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592, 106; EP 519,596; Padlan, *Molecular Immunology*, 28(4/5): 489-498, 1991; Studnicka et al., *Protein Engineering*, 7(6): 805-814, 1994; Roguska et al., *Proc Natl. Acad. Sci. USA*, 91:969-973, 1994), and chain shuffling (U.S. Pat. No. 5,565, 332), all of which are hereby incorporated by reference in their entireties.

5.3.2. Additional Considerations for Preparing Humanized Antibodies as Pharmaceuticals To offer humanized antibodies as pharmaceuticals, an efficient and consistent production system therefore needs to be prepared. For example, an appropriate expression vector for humanized antibodies is prepared by inserting H-chain and L-chain sequences, and a high-productivity cell line transfected with the expression vector can be obtained as a seed cell for a master cell bank (MCB), which serves as a stable and semi-permanent source for a working cell bank (WCB). Humanized antibodies can be then prepared by culturing working cells from the WCB and collecting the culture medium.

Various expression vectors with appropriate regulatory genes can be used for the preparation of such a production cell line. As a host cell, those commonly used for expressing mammalian proteins can be used for the expression of humanized antibodies. Examples of such host cells include, but are not limited to, Chinese Hamster Ovary (CHO) cells, SP2/0-Ag14.19 cells, NSO cells, and the like. The productivity of humanized antibodies can be maximized by selecting the best combination of an expression vector and a host cell. Furthermore, the composition of culture media should be explored in order to select suitable media, from various serum-free culture media and supplements, so that the expression of humanized antibodies by the host cell can be optimized.

Based on the efficiency and the final yield, the humanized antibodies produced by the host cell can be purified from the culture supernatant using various methods well known in the art, including affinity chromatography, ion-exchange chromatography, hydrophobic interaction chromatography, and the like.

5.4 Pharmaceutical Composition and Therapeutic Uses

The present invention provides a pharmaceutical composition comprising the humanized antibody or an antigen-binding fragment thereof, described above, that immunospecifically recognizes the RGD sequence. The pharmaceutical composition comprising the humanized antibody of the present invention as an active ingredient can be used as an agent for preventing and/or treating a disorder or disease that is associated with RGD proteins, including, but not limited to, cancer, e.g., the growth or metastasis of cancer cells, and an inflammatory disease, e.g., rheumatoid arthritis, osteoarthritis, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, and the like.

The pharmaceutical composition comprising the humanized antibody of the present invention can also be used to treat chronic rejection after organ transplantation, and an autoimmune disease such as systemic autoimmune disease, erythematosus, uveitis, Behcet's disease, polymyositis, glomerular proliferative nephritis, sarcoidosis, and the like.

The preventive and/or therapeutic agent for preventing or treating the disorders or diseases described above, comprising the humanized antibody of the present invention, has low toxicity and can be administered to humans orally or parenterally, directly as a liquid preparation by mixing in a suitable solvent, or as a pharmaceutical composition in an appropriate dosage form.

The pharmaceutical composition used for the administration described above contains the aforesaid antibody or salts thereof and pharmaceutically acceptable carriers, diluents or excipients. Such a composition is provided in a dosage form suitable for oral or parenteral administration.

The dose may vary depending upon the age and the size of a subject to be administered, target disease, conditions, route of administration, and the like. When the antibody is used for preventing and/or treating, for example, rheumatoid arthritis in an adult patient, it is advantageous to intravenously administer the antibody of the present invention normally at a single dose of about 0.01 to about 20 mg/kg body weight, preferably about 0.1 to about 10 mg/kg body weight, and more preferably about 0.1 to about 5 mg/kg body weight, approximately 1 to 5 times per day, preferably approximately 1 to 3 times per day. In other parenteral administration and oral administration, the antibody can be administered in a dose corresponding to the dose given above. When the condition is especially severe, the dose may be increased according to the condition.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu and Wu, 1987, *J. Biol. Chem.* 262:4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In an aspect of the present invention, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, by means of nasal spray, or by means of an implant, said implant being of a porous, non porous, or gelatinous material, including membranes, such as sialastic membranes, or fibers. In one aspect of the present invention, administration can be by direct injection at the site (or former site) infected tissues.

In another aspect of the present invention, the pharmaceutical composition can be delivered in a vesicle, in particular a liposome (see Langer, 1990, *Science* 249:1527-1533; Treat et al., in Liposomes in the Therapy of Infectious Disease and Cancer, Lopez Berestein and Fidler (eds.), Liss, New York, pp. 353-365 (1989); Lopez-Berestein, ibid., pp. 317-327; see generally ibid.).

In yet another aspect of the present invention, the pharmaceutical composition can be delivered in a controlled release system. In an aspect of the present invention, a pump may be used (see Langer, supra; Sefton, 1987, *CRC Crit. Ref. Biomed. Eng.* 14:201; Buchwald et al., 1980, Surgery 88:507; and Saudek et al., 1989, *N. Engl. J. Med.* 321:574). In another aspect of the present invention, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, *J. Macromol. Sci. Rev. Macromol. Chem.* 23:61 (1983); see also Levy et al., 1985, *Science* 228:190; During et al., 1989, *Ann. Neurol.* 25:351; Howard et al., 1989, *J. Neurosurg.* 71:105). In yet another aspect of the present invention, a controlled release system can be placed in proximity of the composition's target, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

Examples of the composition for oral administration include solid or liquid dosage forms, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, and the like.

The injectable preparations may include dosage forms for intravenous, subcutaneous, intracutaneous and intramuscular injections, drip infusions, etc. These injectable preparations may be prepared by methods publicly known. The injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 500 mg per dosage form in a unit dose; especially in the form of injection, it is preferred that the aforesaid antibody is contained in about 5 to 100 mg and in about 10 to 250 mg for the other dosage forms.

Each composition described above may further contain other active components unless formulation causes any adverse interaction with the antibodies described above.

The present invention also relates to an inhibitor and/or promoter for cell and/or tissue remodeling, which comprises an RGD sequence-binding functional molecule (e.g., integrins, etc.) as an active ingredient; and a method for inhibiting and/or promoting cell and/or tissue remodeling, which comprises contacting the RGD protein expressing cell and/or tissue (e.g., a tumor cell, neutrophil, smooth muscle, etc.) with the RGD protein binding functional molecule. The dose, method for administration, pharmaceutical preparation, etc. of the active ingredient in such a therapeutic agent can be appropriately determined by referring to the foregoing description of medicaments comprising the humanized antibodies of the present invention.

As described above, the present invention further provides a method for preventing or treating a disorder or disease that is associated with or involves RGD proteins, said method comprising administering an effective amount of at least one of the humanized antibodies of the present invention to a subject in need thereof.

5.5 Diagnostic Uses

The pharmaceutical composition comprising the humanized antibody of the present invention can be used as a diagnostic agent for cancer, e.g., the growth or metastasis of cancer cells, and an inflammatory disease, e.g., rheumatoid arthritis, osteoarthritis, hepatitis, bronchial asthma, fibrosis, diabetes mellitus, cancer metastasis, arteriosclerosis, multiple sclerosis, granuloma, etc., or as a diagnostic agent for chronic rejection after organ transplantation, an autoimmune disease such as systemic autoimmune disease, erythematosus, uveitis, Behcet's disease, polymyositis, glomerular proliferative nephritis, sarcoidosis, and so forth. The humanized antibodies of the present invention are capable of specifically recognizing the RGD sequence and hence can be used to quantify the RGD proteins in a test fluid, especially for quantification by the sandwich immunoassay, competitive assay, immunometry, nephrometry, etc., immunostaining, or the like. In applying these immunological methods to the assay methods of the present invention, it is not required to set forth any particular conditions, procedures, etc. It is sufficient to construct assay systems by adding ordinary technical consideration in the art to conventional conditions and procedures. For details of these general technical means, reference can be made to reviews, texts or the like.

As described above, the RGD proteins may be quantified with high sensitivity by using the antibodies of the present invention. The humanized antibodies of the present inventions are particularly useful for diagnosing various diseases associated with the RGD proteins by applying the method for quantifying the RGD proteins in vivo. For instance, where an increase or decrease in the expression level of the RGD proteins is detected, it can be diagnosed that it is highly likely that one now suffers from diseases associated with the RGD protein, e.g., cancer or an inflammatory disease, or it is highly likely that one will suffer from these diseases in the future. Thus, the present invention also provides a method for diagnosing a disorder or disease associated with or involve the RGD proteins in a subject, said method comprising administering an effective amount of at least one of the humanized antibodies of the present invention or both to a subject in need thereof. Required dosages for such an in vivo diagnosis may be less than those required for therapeutic uses and can be determined by one skilled in the art according to routine procedures.

The humanized antibodies of the present invention can also be used for specifically detecting the RGD proteins present in a test sample (e.g., a test fluid such as a body fluid, a tissue, etc). The humanized antibodies can also be used for preparation of antibody columns for purification of the RGD proteins, for detection of the RGD proteins contained in each fraction upon purification or for analysis of behaviors of the RGD proteins in cells to be tested.

The sequence identification numbers in the sequence listing of the specification indicate the following sequences.

[SEQ ID NO: 1]
This shows the amino acid sequence of CDRH1 common to mouse 33E10 and human 33E10.

[SEQ ID NO: 2]
This shows the amino acid sequence of CDRH2 common to mouse 33E10 and human 33E10.

[SEQ ID NO: 3]
This shows the amino acid sequence of CDRH3 common to mouse 33E10 and human 33E10.

[SEQ ID NO: 4]
This shows the amino acid sequence of CDRL1 common to mouse 33E10 and human 33E10.

[SEQ ID NO: 5]
This shows the amino acid sequence of CDRL2 common to mouse 33E10 and human 33E10.

[SEQ ID NO: 6]
This shows the amino acid sequence of CDRL3 common to mouse 33E10 and human 33E10.

[SEQ ID NO: 7]
This shows the nucleotide sequence of the Hu33E10 VH5 gene including a sequence encoding a signal peptide and the intron sequence, flanked by SpeI and HindIII sites.

[SEQ ID NO: 8]
This shows the amino acid sequence of encoded by the nucleotide sequence of the Hu33E10 VH5 gene including a signal peptide.

[SEQ ID NO: 9]
This shows the nucleotide sequence of the Hu33E10 VH7 gene including a sequence encoding a signal peptide and the intron sequence, flanked by SpeI and HindIII sites.

[SEQ ID NO: 10]
This shows the amino acid sequence of encoded by the nucleotide sequence of the Hu33E10 VH7 gene including a signal peptide.

[SEQ ID NO: 11]
This shows the nucleotide sequence of the Hu33E10 VH7.8 gene including a sequence encoding a signal peptide and the intron sequence, flanked by SpeI and HindIII sites.

[SEQ ID NO: 12]
This shows the amino acid sequence of encoded by the nucleotide sequence of the Hu33E10 VH7.8 gene including a signal peptide.

[SEQ ID NO: 13]
This shows the nucleotide sequence of the Hu33E10 VL6 gene including a sequence encoding a signal peptide and the intron sequence, flanked by NheI and EcoRI sites.

[SEQ ID NO: 14]
This shows the amino acid sequence of encoded by the nucleotide sequence of the Hu33E10 VL6 gene including a signal peptide.

[SEQ ID NO: 15]
This shows the nucleotide sequence of the Hu33E10 VLv2 gene including a sequence encoding a signal peptide and the intron sequence, flanked by NheI and EcoRI sites.

[SEQ ID NO: 16]
This shows the amino acid sequence of encoded by the nucleotide sequence of the Hu33E10 VLv2 gene including a signal peptide.

[SEQ ID NO: 17]
This shows the oligonucleotide [CMV2] used for PCR amplification and sequencing of Hu33E10 heavy and light chain cDNA.

[SEQ ID NO: 18]
This shows the oligonucleotide [JNT026] used for PCR amplification and sequencing of Hu33E10 heavy and light chain cDNA.

[SEQ ID NO: 19]
This shows the oligonucleotide [JNT080] used for PCR amplification and sequencing of Hu33E10 heavy and light chain cDNA.

[SEQ ID NO: 20]
This shows the oligonucleotide [JNT082] used for PCR amplification and sequencing of Hu33E10 heavy and light chain cDNA.

[SEQ ID NO: 21]
This shows the oligonucleotide [JNT084] used for PCR amplification and sequencing of Hu33E10 heavy and light chain cDNA.

[SEQ ID NO: 22]
This shows the oligonucleotide [JNT097] used for PCR amplification and sequencing of Hu33E10 heavy and light chain cDNA.

[SEQ ID NO: 23]
This shows the oligonucleotide [JNT098] used for PCR amplification and sequencing of Hu33E10 heavy and light chain cDNA.

[SEQ ID NO: 24]
This shows the nucleotide sequence of the coding region for VH7 and gamma-1 heavy chain constant regions expressed in NS0-Hu33E10-4 and NS0-Hu33E10-6.

[SEQ ID NO: 25]
This shows the amino acid sequence encoded by the nucleotide sequence of the coding region for VH7 and gamma-1 heavy chain constant regions expressed in NS0-Hu33E10-4 and NS0-Hu33E10-6.

[SEQ ID NO: 26]
This shows the nucleotide sequence of the coding region for VH7.8 and gamma-1 heavy chain constant regions expressed in NS0-Hu33E10-5.

[SEQ ID NO: 27]
This shows the amino acid sequence encoded by the nucleotide sequence of the coding region for VH7.8 and gamma-1 heavy chain constant regions expressed in NS0-Hu33E10-5.

[SEQ ID NO: 28]
This shows the nucleotide sequence of the coding region for VL6 and kappa light chain constant regions expressed in NS0-Hu33E10-4 and NS0-Hu33E10-5.

[SEQ ID NO: 29]
This shows the amino acid sequence encoded by the nucleotide sequence of the coding region for VL6 and kappa light chain constant regions expressed in NS0-Hu33E10-4 and NS0-Hu33E10-5.

[SEQ ID NO: 30]
This shows the nucleotide sequence of the coding region for VLv2 and kappa light chain constant regions expressed in NS0-Hu33E10-6.

[SEQ ID NO: 31]
This shows the amino acid sequence encoded by the nucleotide sequence of the coding region for VLv2 and kappa light chain constant regions expressed in NS0-Hu33E10-6.

[SEQ ID NO: 32]
This shows the amino acid sequences of 33E10 VL.

[SEQ ID NO: 33]
This shows the amino acid sequences of Hu33E10 VLv2.

[SEQ ID NO: 34]
This shows the nucleotide sequence of mouse 33E10 VH cDNA.

[SEQ ID NO: 35]
This shows the amino acid sequence encoded by the nucleotide sequence of mouse 33E10 VH cDNA.

[SEQ ID NO: 36]
This shows the nucleotide sequence of mouse 33E10 VL cDNA.

[SEQ ID NO: 37]
This shows the amino acid sequence encoded by the nucleotide sequence of mouse 33E10 VL cDNA.

[SEQ ID NO: 38]
This shows the nucleotide sequence of the designed 33E10 VH gene including a sequence encoding a signal peptide and the intron sequence, flanked by SpeI and HindIII sites.

[SEQ ID NO: 39]
This shows the amino acid sequence encoded by the nucleotide sequence of the designed 33E10 VH gene including a signal peptide.

[SEQ ID NO: 40]
This shows the nucleotide sequence of the designed 33E10 VL gene including a sequence encoding a signal peptide and the intron sequence, flanked by NheI and EcoRI sites.

[SEQ ID NO: 41]
This shows the amino acid sequence encoded by the nucleotide sequence of the designed 33E10 VL gene including a signal peptide.

[SEQ ID NO: 42]
This shows the amino acid sequences of 33E10 VH.

[SEQ ID NO: 43]
This shows the amino acid sequences of humanized 33E10 (Hu33E10) VH1.

[SEQ ID NO: 44]
This shows the amino acid sequences of 33E10 VL.
[SEQ ID NO: 45]
This shows the amino acid sequences of humanized 33E10 (Hu33E10) VL1.
[SEQ ID NO: 46]
This shows the oligonucleotide [JNJ220] used for construction of the Hu33E10 VH1 gene.
[SEQ ID NO: 47]
This shows the oligonucleotide [JNJ206] used for construction of the Hu33E10 VH1 gene.
[SEQ ID NO: 48]
This shows the oligonucleotide [JNJ207] used for construction of the Hu33E10 VH1 gene.
[SEQ ID NO: 49]
This shows the oligonucleotide [JNJ208] used for construction of the Hu33E10 VH1 gene.
[SEQ ID NO: 50]
This shows the oligonucleotide [JNJ209] used for construction of the Hu33E10 VH1 gene.
[SEQ ID NO: 51]
This shows the oligonucleotide [JNJ210] used for construction of the Hu33E10 VH1 gene.
[SEQ ID NO: 52]
This shows the oligonucleotide [JNJ211] used for construction of the Hu33E10 VH1 gene.
[SEQ ID NO: 53]
This shows the oligonucleotide [JNJ212] used for construction of the Hu33E10 VH1 gene.
[SEQ ID NO: 54]
This shows the oligonucleotide [JNJ213] used for construction of the Hu33E10 VH1 gene.
[SEQ ID NO: 55]
This shows the oligonucleotide [JNJ214] used for construction of the Hu33E10 VH1 gene.
[SEQ ID NO: 56]
This shows the oligonucleotide [JNJ215] used for construction of the Hu33E10 VH1 gene.
[SEQ ID NO: 57]
This shows the oligonucleotide [JNJ216] used for construction of the Hu33E10 VH1 gene.
[SEQ ID NO: 58]
This shows the oligonucleotide [JNJ217] used for construction of the Hu33E10 VH1 gene.
[SEQ ID NO: 59]
This shows the oligonucleotide [JNJ218] used for construction of the Hu33E10 VH1 gene.
[SEQ ID NO: 60]
This shows the oligonucleotide [JNJ219] used for construction of the Hu33E10 VH1 gene.
[SEQ ID NO: 61]
This shows the oligonucleotide [JNJ221] used for construction of the Hu33E10 VH1 gene.
[SEQ ID NO: 62]
This shows the oligonucleotide [JNJ116] used for construction of the Hu33E10 VL1 gene.
[SEQ ID NO: 63]
This shows the oligonucleotide [JNJ193] used for construction of the Hu33E10 VL1 gene.
[SEQ ID NO: 64]
This shows the oligonucleotide [JNJ194] used for construction of the Hu33E10 VL1 gene.
[SEQ ID NO: 65]
This shows the oligonucleotide [JNJ195] used for construction of the Hu33E10 VL1 gene.
[SEQ ID NO: 66]
This shows the oligonucleotide [JNJ196] used for construction of the Hu33E10 VL1 gene.
[SEQ ID NO: 67]
This shows the oligonucleotide [JNJ197] used for construction of the Hu33E10 VL1 gene.
[SEQ ID NO: 68]
This shows the oligonucleotide [JNJ198] used for construction of the Hu33E10 VL1 gene.
[SEQ ID NO: 69]
This shows the oligonucleotide [JNJ199] used for construction of the Hu33E10 VL1 gene.
[SEQ ID NO: 70]
This shows the oligonucleotide [JNJ200] used for construction of the Hu33E10 VL1 gene.
[SEQ ID NO: 71]
This shows the oligonucleotide [JNJ201] used for construction of the Hu33E10 VL1 gene.
[SEQ ID NO: 72]
This shows the oligonucleotide [JNJ202] used for construction of the Hu33E10 VL1 gene.
[SEQ ID NO: 73]
This shows the oligonucleotide [JNJ203] used for construction of the Hu33E10 VL1 gene.
[SEQ ID NO: 74]
This shows the oligonucleotide [JNJ204] used for construction of the Hu33E10 VL1 gene.
[SEQ ID NO: 75]
This shows the oligonucleotide [JNJ205] used for construction of the Hu33E10 VL1 gene.
[SEQ ID NO: 76]
This shows the oligonucleotide [JNJ101] used for construction of the Hu33E10 VL1 gene.
[SEQ ID NO: 77]
This shows the oligonucleotide [JNJ117] used for construction of the Hu33E10 VL1 gene.
[SEQ ID NO: 78]
This shows the nucleotide sequence of the Hu33E10 VH1 gene including a sequence encoding a signal peptide and the intron sequence, flanked by SpeI and HindIII sites.
[SEQ ID NO: 79]
This shows the amino acid sequence encoded by the nucleotide sequence of the Hu33E10 VH1 gene including a signal peptide.
[SEQ ID NO: 80]
This shows the nucleotide sequence of the Hu33E10 VL1 gene including a sequence encoding a signal peptide and the intron sequence, flanked by NheI and EcoRI sites.
[SEQ ID NO: 81]
This shows the amino acid sequence encoded by the nucleotide sequence of the Hu33E10 VL1 gene including a signal peptide.
[SEQ ID NO: 82]
This shows the nucleotide sequence of 5' RACE primer.
[SEQ ID NO: 83]
This shows the nucleotide sequence of 5' RACE primer.
[SEQ ID NO: 84]
This shows the nucleotide sequence of GeneRacer 5' primer.
[SEQ ID NO: 85]
This shows the nucleotide sequence of 33E10 VH 3' primer.
[SEQ ID NO: 86]
This shows the nucleotide sequence of 33E10 VL 3' primer.
[SEQ ID NO: 87]
This shows the nucleotide sequence of 33E10 VH 5' primer.

[SEQ ID NO: 88]
This shows the nucleotide sequence of 33E10 VH 3' primer.

[SEQ ID NO: 89]
This shows the nucleotide sequence of 33E10 VL 5' primer.

[SEQ ID NO: 90]
This shows the nucleotide sequence of 33E10 VL 3' primer.

[SEQ ID NO: 91]
This shows the nucleotide sequence of the Hu33E10 VH5 gene.

[SEQ ID NO: 92]
This shows the amino acid sequence of encoded by the nucleotide sequence of the Hu33E10 VH5 gene.

[SEQ ID NO: 93]
This shows the nucleotide sequence of the Hu33E10 VH7 gene.

[SEQ ID NO: 94]
This shows the amino acid sequence of encoded by the nucleotide sequence of the Hu33E10 VH7 gene.

[SEQ ID NO: 95]
This shows the nucleotide sequence of the Hu33E10 VH7.8 gene.

[SEQ ID NO: 96]
This shows the amino acid sequence of encoded by the nucleotide sequence of the Hu33E10 VH7.8.

[SEQ ID NO: 97]
This shows the nucleotide sequence of the Hu33E10 VL6 gene.

[SEQ ID NO: 98]
This shows the amino acid sequence of encoded by the nucleotide sequence of the Hu33E10 VL6 gene.

[SEQ ID NO: 99]
This shows the nucleotide sequence of the Hu33E10 VLv2 gene.

[SEQ ID NO: 100]
This shows the amino acid sequence of encoded by the nucleotide sequence of the Hu33E10 VLv2 gene.

6. EXAMPLES

The following examples illustrate preparation of monoclonal antibodies that immunospecifically recognize the RGD sequence, sequencing of the V-regions of the monoclonal antibodies, epitope mapping and other characterization of the antibodies and chimerization and the humanization of such antibodies, as well as the characterization of the resulting chimeric and humanized antibodies. These examples should not be construed as limiting the scope of the invention.

6.1. Cloning and Sequencing of Mouse 33E10 Variable Region Genes

Mouse 33E10 hybridoma cells were grown in TIL Media I (Immuno-Biological Laboratories, Gunma, Japan) containing 10% fetal bovine serum (FBS; HyClone, Logan, Utah) at 37° C. in a 7.5% $CO_2$ incubator. Total RNA was extracted from approximately $3×10^6$ hybridoma cells using TRIzol reagent (Invitrogen, Carlsbad, Calif.) according to the supplier's protocol. Oligo dT-primed cDNA was synthesized using the GeneRacer Kit (Invitrogen) following the supplier's protocol. The variable region cDNAs for 33E10 heavy and light chains were amplified by polymerase chain reaction (PCR) with Phusion DNA polymerase (New England Biolabs, Beverly, Mass.) using 3' primers that anneal respectively to the mouse gamma-1 and kappa chain constant regions, and a GeneRacer 5' primer (5'-CGACTGGAGCACGAGGA-CACTGA-3' (SEQ ID NO: 84)) provided in the GeneRacer Kit. For PCR amplification of heavy chain variable region (VH), the 3' primer has the sequence 5'-GCCAGTGGATA-GACAGATGG-3' (SEQ ID NO: 85). For PCR amplification of light chain variable region (VL), the 3' primer has the sequence 5'-GATGGATACAGTTGGTGCAGC-3' (SEQ ID NO: 86). The amplified VH and VL cDNAs were cloned into the pCR4Blunt-TOPO vector (Invitrogen) for sequence determination. DNA sequencing of the variable regions was carried out at Tocore (Menlo Park, Calif.). Several heavy and light chain clones were sequenced and unique sequences homologous to typical mouse heavy and light chain variable regions were identified. The consensus cDNA sequences along with deduced amino acid sequences of 33E10 VH and VL are shown in FIGS. 1 and 2, respectively.

6.2. Construction of Chimeric 33E10 IgG1/κ Antibody

Figure 5:
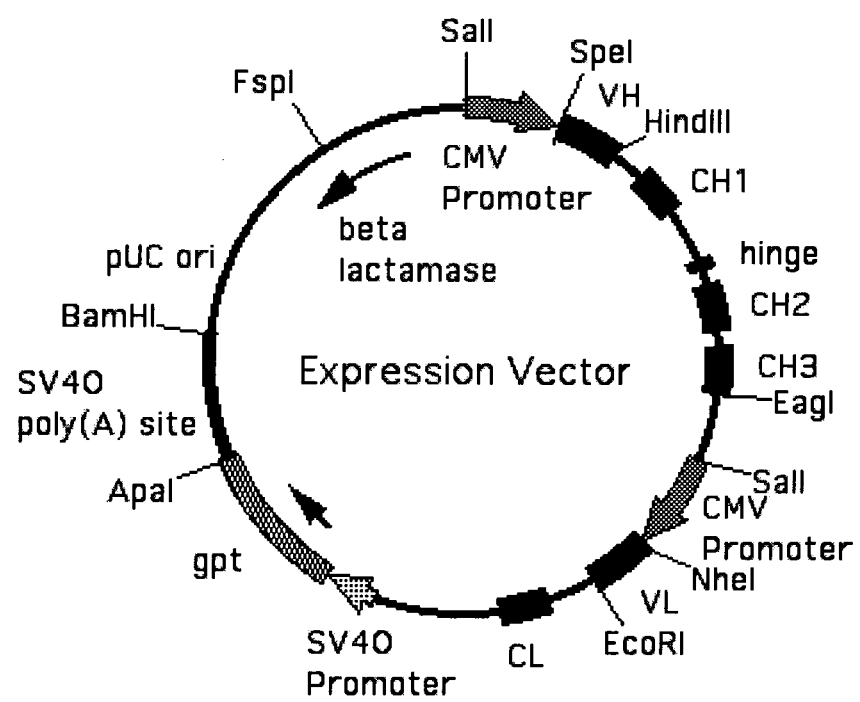

A gene encoding 33E10 VH was generated as an exon including a splice donor signal and appropriate flanking restriction enzyme sites by PCR using 33E10 VH cDNA as a template, 5'-GGGACTAGTACCACCATGAAGTTGT GGCTGAACTGGATT-3' (SEQ ID NO: 87) (SpeI site is underlined) as a 5' primer, and 5'-GGG AAGCTTGAAGTTAGGACTCACCTGCAGAGACAGTG ACCAGAGTCCC-3' (SEQ ID NO: 88) (HindIII site is underlined) as a 3' primer (FIG. 3). Likewise, a gene encoding 33E10 VL was generated as an exon including a splice donor signal and appropriate flanking restriction enzyme sites by PCR using 33E10 VL cDNA as a template, 5'-GGG GCTAGCACCACCATGAAGTTGCCTGTTAGGCTGTT G-3' (SEQ ID NO: 89) (NheI site is underlined) as a 5' primer, and 5'-GGGGAATTCTTTGGATTCTACTTACGTTT GATTT CCAGCTTGGTGCCTCC-3' (SEQ ID NO: 90) (EcoRI site is underlined) as a 3' primer (FIG. 4). The splice donor signals of the 33E10 VH and VL exons were derived from the mouse germline JH3 and Jκ1 sequences, respectively (Kabat et al., Sequences of Proteins of Immunological Interests, Fifth edition, NIH Publication No. 91-3242, U.S. Department of Health and Human Services, 1991). PCR-amplified fragments were gel-purified using QIAquick Gel Extraction Kit (Qiagen, Valencia, Calif.), digested with SpeI and HindIII (for VH) or NheI and EcoRI (for VL), and cloned into a mammalian expression vector carrying human gamma-1 and kappa constant regions for production of chimeric 33E10 IgG1/κ antibody. The schematic structure of the resulting expression vector, pCh33E10, is shown in FIG. 5.

6.3. Generation of Humanized 33E10 VII and VL Genes

Humanization of the 33E10 variable regions was carried out as outlined by Queen et al. (Proc. Natl. Acad. Sci. USA 86: 10029-10033, 1989). First, a three-dimensional molecular model of the 33E10 variable regions was constructed with the aid of computer programs. Next, based on a homology search against human variable region sequences, the human VH amino acid sequence of U03400 (GenBank accession number), which has a high homology to 33E10 VH, was chosen as an acceptor to provide the frameworks for humanized 33E10 VH. Likewise, the human VL amino acid sequence of X72452 (GenBank accession number) was chosen as an acceptor for humanization of 33E10 VL.

At framework positions where the three-dimensional model suggested significant contact with the complementarity determining regions (CDRs), amino acid residues from the mouse 33E10 variable regions were substituted for the human framework residues. This was performed at positions 30 and 48 to generate humanized 33E10 (Hu33E10) VH1 (FIG. 6). For the light chain, no replacements were needed to generate Hu33E10 VL1 (FIG. 7). The alignments of 33E10, designed Hu33E10 and the human acceptor amino acid sequence are shown for VH in FIG. 6 and for VL in FIG. 7.

A gene encoding each of Hu33E10 VH1 and VL1 was designed as an exon including a signal peptide, a splice donor signal, and appropriate restriction enzyme sites for subsequent cloning into a mammalian expression vector. The splice donor signals of the Hu33E10 VH1 and VL1 exons were derived from the human germline JH3 and Jκ1 sequences (Kabat et al., 1991), respectively. The signal peptide sequence of the mouse 33E10 VL1 gene was indicated to be suboptimal for precise cleavage by the SIG-Pred signal peptide prediction software (http://bmbpcu36.leeds.ac.uk/prot_analysis/Signal.html). Therefore, the signal peptide of the VL gene of the mouse monoclonal antibody 35B6 (Gene Techno Science), which was predicted to be cleaved efficiently and precisely by the SIG-Pred software, was used in the Hu33E10 VL1 exon. The signal peptide sequence in the Hu33E10 VH1 exon was derived from the corresponding mouse 33E10 VH sequence. The SIG-Pred software indicated that the signal peptide of the Hu33E10 VH1 gene is cleaved efficiently and precisely.

The Hu33E10 VH1 and VL1 genes were constructed by extension and PCR amplification of several overlapping synthetic oligonucleotide primers using Phusion DNA polymerase as outlined by He et al. (*J. Immunol.* 160: 1029-1035, 1998). The oligonucleotides used for construction of Hu33E10 VH1 and VL1 genes are listed in FIGS. 8 and 9, respectively. The location of the oligonucleotides in the Hu33E10 VH1 and VL1 genes is shown in FIGS. 10 and 11, respectively. PCR-amplified fragments were gel-purified using QIAquick Gel Extraction Kit (Qiagen) and cloned into pCR4Blunt-TOPO vector for sequence determination. After digestion with SpeI and HindIII (for VH) or NheI and EcoRI (for VL), Hu33E10 VH1 and VL1 genes were subcloned into corresponding sites in a mammalian expression vector for production of the human IgG1/κ form. The schematic structure of the resulting expression vector, pHu33E10-1, is shown in FIG. 5. The nucleotide sequences of the obtained Hu33E10 VH1 and VL1 genes along with deduced amino acid sequences are shown in FIGS. 12 and 13, respectively.

6.4. Expression of Chimeric and Humanized 33E10 Antibodies

To obtain cell lines stably producing each of chimeric and humanized 33E10 IgG1/κ antibodies, the expression vectors pCh33E10 and pHu33E10-1, respectively, were introduced into the chromosome of a mouse myeloma cell line NS0 (European Collection of Animal Cell Cultures, Salisbury, Wiltshire, UK). NS0 cells were grown in DME medium containing 10% FBS at 37° C. in a 7.5% $CO_2$ incubator. Stable transfection into NS0 cells was carried out by electroporation as described in Bebbington et al. (Bio/Technology 10: 169-175, 1992). Before transfection, each expression vector was linearized using FspI. Approximately $10^7$ cells were transfected with 10 μg of linearized plasmid, suspended in DME medium containing 10% FBS, and plated into several 96-well plates. After 24 to 48 hr, selection media (DME medium containing 10% FBS, HT media supplement (Sigma, St. Louis, Mo.), 0.25 mg/ml xanthine and 1 μg/ml mycophenolic acid) was applied. Approximately 10 days after the initiation of selection, culture supernatants were assayed for antibody production.

The expression level of recombinant antibodies expressed from pCh33E10 and pHu33E10-1 (Ch33E10 and Hu33E10-VH1/VL1, respectively) in culture supernatant was measured by sandwich ELISA. In a typical experiment, an ELISA plate was coated overnight at 4° C. with 100 μl/well of 1/2,000-diluted goat anti-human IgG Fcγ-chain-specific polyclonal antibody (SouthernBiotech, Birmingham, Ala.) in PBS, washed with Wash Buffer (PBS containing 0.05% Tween 20), and blocked for 1 hr at room temperature with 300 μl/well of Blocking Buffer (PBS containing 2% Skim Milk and 0.05% Tween 20). After washing with Wash Buffer, 100 μl/well of samples appropriately diluted in ELISA Buffer (PBS containing 1% Skim Milk and 0.025% Tween 20) were applied to the ELISA plate. Human IgG1/κ antibody purified from human myeloma serum (SouthernBiotech) or purified Ch33E10 was used as a standard. After incubating the ELISA plate for 2 hr at room temperature and washing with Wash Buffer, bound antibodies were detected using 100 of 1/2,000-diluted HRP-conjugated goat anti-human kappa chain polyclonal antibody (SouthernBiotech). After incubating for 1 hr at room temperature and washing with Wash Buffer, color development was performed by adding 100 μl/well of ABTS substrate and stopped with 100 μl/well of 2% oxalic acid. Absorbance was read at 405 nm.

One of the NS0 stable transfectants producing a high level of Ch33E10 (NS0-Ch33E10 2C11; also called L4-2C11) was adapted to growth in serum-free media using Hybridoma SFM (Invitrogen), expanded in roller bottles to the density of about $10^6$/ml, fed with 6 mg/ml of Ultrafiltrated Soy Hydrolyzate (Irvine Scientific Cat #96857), and grown further until the cell viability became less than 50%. After centrifugation and filtration, culture supernatant was loaded onto a protein-A Sepharose column (GE Healthcare, Piscataway, N.J.). The column was washed with PBS before the antibody was eluted with 0.1 M glycine-HCl (pH 3.0). After neutralization with 1 M Tris-HCl (pH 8), the buffer of eluted antibody was changed to PBS by dialysis. Antibody concentration was determined by measuring absorbance at 280 nm (1 mg/ml=1.4 OD).

While NS0 stable transfectants expressing Ch33E10 were easily obtained, all of NS0 transfectants stably transfected with pHu33E10-1 turned out to be poor producers of Hu33E10-VH1/VL1. The analysis of heavy and light chain mRNA revealed the presence of aberrant light chain mRNA lacking the VL coding region due to an accidentally generated splice donor site in the signal peptide-coding region of the VL1 gene. To solve this problem, the splicing donor site in the signal peptide-coding region was eliminated by site-directed mutagenesis using the overlap-extension PCR method (Higuchi, R., in PCR Technology: Principles and Applications for DNA Amplification. Erlich, H. A., ed. pp. 61-70, Stockton Press, New York, 1989). The sequence of the resulting variant Hu33E10 VL gene, VL6, is shown in FIG. 14. The VL region amino acid sequence is identical to each other between the VL1 and VL6 genes. The VL6 gene was replaced for VL1 in the expression vector pHu33E10-1 to generate pHu33E10-2. NS0 cells stably transfected with pHu33E10-2 and producing a high level of recombinant antibody (Hu33E10-VH1/VL6) were obtained by the methods described above. No aberrant light chain mRNA was observed in the NS0 cells stably transfected with pHu33E10$^{-2}$. One of the NS0 stable transfectants producing a high level of Hu33E10-VH1/VL6 (NS0-Hu33E10-2 #22) was adapted to and expanded in Hybridoma SFM, and the culture supernatant was used for purification of Hu33E10-VH1/VL6 as described above.

6.5. Characterization of Hu33E10-VH1/VL6

Binding of Ch33E10 and Hu33E10-VH1/VL6 IgG1/κ antibodies to hOPN5-BSA was examined by ELISA. As an antigen, synthetic oligopeptide (Cys-Val-Asp-Thr-Tyr-Asp-Gly-Arg-Gly-Asp-Ser-Val-Val-Tyr-Gly-Leu-Arg-Ser; provided by Gene Techno Science) conjugated to bovine serum albumin (hOPN5-BSA) was used. In a typical experiment, an ELISA plate was coated with 100 μl/well of 1 μg/ml hOPN5-BSA in 0.2 M $Na_2CO_3$ buffer (pH 9.4) overnight at 4° C., washed with Wash Buffer, and blocked with 300 μl/well of Blocking Buffer for 1 hr at room temperature. After washing with Wash Buffer, samples appropriately diluted in ELISA Buffer were applied at 100 μl/well in the ELISA plate. After incubating the ELISA plate overnight at 4° C. and washing with Wash Buffer, bound antibodies were detected using 100 μl/well of 1/2,000-diluted HRP-conjugated goat anti-human γ chain polyclonal antibody (SouthernBiotech). After incubating for 1 hr at room temperature and washing with Wash Buffer, color development was performed by adding 100 μl/well of ABTS substrate and stopped with 100 μl/well of 2% oxalic acid. Absorbance was read at 405 nm.

As shown in FIG. 15A, Hu33E10-VH1/VL6 was roughly 100-fold weaker for binding to hOPN5-BSA than Ch33E10.

6.6. Generation and Characterization of Hu33E10 VH5, VH7 and VH7.8

In order to identify which of the humanized VH1 and VL6 genes is responsible for the loss of antigen-binding affinity of Hu33E10-VH1/VL6, two recombinant IgG1/κ antibodies, one consisting of mouse VH and humanized VL6 (MoHu33E10) and another consisting of humanized VH1 and mouse VL (HuMo33E10), were generated. Through the analyses of MoHu33E10 and HuMo33E10 antibodies, it was found that the loss of the affinity of Hu33E10-VH1/VL6 was mostly due to the VH1 gene and partially to the VL1 gene (data now shown).

Based on preliminary mutation analyses of the VH1 gene, amino acids at positions 73 to 77 were suspected to be important for maintaining the antigen-binding affinity (data not shown). Three variants of the VH1 gene (VH5, VH7 and VH7.8) constructed by site-directed mutagenesis using the overlap-extension PCR method (Higuchi, 1989) were chosen for further analysis. In comparison with VH1, Ile at position 77 was substituted for Ser in VH5 (FIGS. 6 and 16), Ser at 76 and Ile at 77 for Asn and Ser, respectively, in VH7 (FIGS. 6 and 17), and Ser at 74, Ser at 76 and Ile at 77 for Ala, Asn and Ser, respectively, in VH7.8 (FIGS. 6 and 18).

Each of the VH5, VH7 and VH7.8 genes digested with SpeI and HindIII was substituted for VH1 in pHu33E10-2 to construct expression vectors pHu33E10-3, pHu33E10-4 and pHu33E10-5, respectively. NS0 cells stably transfected with each of pHu33E10-3, pHu33E10-4 and pHu33E10-5 were generated as described in Section 4. NS0-Hu33E10-3 #65 producing Hu33E10-VH5/VL6, NS0-Hu33E10-45D3 (also called R3-1 5D3) producing Hu33E10-VH7/VL6, and NS0-Hu33E10-5 1E5 (also called EJ3-3 1E5) producing Hu33E10-VH7.8/VL6 were adapted to growth in Hybridoma SFM and expanded in roller bottles. Hu33E10-VH5/VL6, Hu33E10-VH7/VL6 and Hu33E10-VH7.8/VL6 antibodies were purified from corresponding culture supernatant using a protein A column as described in Section 4.

Binding of Hu33E10-VH5/VL6, Hu33E10-VH7/VL6 and Hu33E10-VH7.8/VL6 antibodies to hOPN5-BSA was compared to that of Ch33E10 by ELISA as described in Section 5. The affinity of Hu33E10-VH5/VL6 to hOPN5-BSA was slightly improved when compared to Hu33E10-VH1/VL6, but it was still much weaker than that of Ch33E10 (FIG. 15A). The binding affinity of Hu33E10-VH7/VL6 to hOPN5-BSA was 3 to 4 fold weaker than that of Ch33E10 (FIG. 15A). The affinity of Hu33E10-VH7.8/VL6 was approximately 3-fold lower than that of Ch33E10 in this experiment (FIG. 15B). In repeated experiments, Hu33E10-VH7/VL6 and Hu33E10-VH7.8/VL6 behaved similarly to each other for binding to hOPN5-BSA.

6.7. Generation and Characterization of Hu33E10 VLv2

Preliminary mutation analyses of the VL1 gene failed to identify any particular framework amino acid residues contributing to the loss of the binding affinity of Hu33E10-VH1/VL6 (data not shown), even though the VL1 gene was suspected to be partially responsible for the loss of the affinity. Instead of further characterizing the VL1 gene, a new humanized 33E10 VL (VLv2) based on a different human framework was designed (FIG. 19). For VLv2, the human amino acid sequence of M29467 (GenBank accession number) was chosen as an acceptor. At positions 22 and 37, where significant interaction with the CDRs was predicted, amino acids residues of mouse 33E10 VL were retained in the humanized form. The Hu33E10 VLv2 gene flanked by Nhe I and EcoRI sites (FIG. 20) was synthesized at GenScript USA Inc. (Piscataway, N.J.). The VL6 and VLv2 genes share the same signal peptide sequence and the splice donor signal (FIGS. 14 and 20).

The Hu33E10 VLv2 gene digested with NheI and EcoRI was substituted for VL1 in pHu33E10-4 to construct a new expression vector pHu33E10-6. NS0 cells stably transfected with pHu33E10-6 to produce Hu33E10-VH7/VLv2 IgG1/κ were generated as described in Section 4. One of the transfectants, NS0-Hu33E10-6 I-15 (also called SP2-1 I-15) was adapted to and expanded in Hybridoma SFM, and Hu33E10-VH7/VLv2 antibody was purified from culture supernatant using the procedures described in Section 4.

Binding of Hu33E10-VH7/VLv2 to hOPN5-BSA was analyzwed by ELISA as described in Section 5. The results of two independent experiments are shown in FIG. 21. The binding affinity of Hu33E10-VH7/VLv2 was within 2-fold of that of Ch33E10 in both experiments.

6.8. Characterization of NS0 Stable Transfectants

Testing with the PCR *Mycoplasma* Detection Set (Takara Bio USA, Madison, Wis.) indicated that NS0-Ch33E10 2C11, NS0-Hu33E10-45D3, NS0-Hu33E10-51E5 and NS0-Hu33E10-6 I-15 were all negative for the presence of mycoplasma.

The authenticity of heavy and light chains of Hu33E10-VH7/VL6, Hu33E10-VH7.8/VL6 and Hu33E10-VH7/VLv2 IgG1/κ antibodies produced in NS0-Hu33E10-45D3, NS0-Hu33E10-51E5 and NS0-Hu33E10-6 I-15, respectively, was confirmed by cDNA sequencing. Total RNA was extracted from these cells using TRIzol reagent (Invitrogen) and oligo dT-primed cDNA was synthesized using the SuperScript III First-Strand Synthesis System for RT-PCR (Invitrogen) following supplier's protocols. The coding region of gamma-1 heavy chain was amplified by PCR using CMV2 and JNT098 as primers (FIG. 22) and Phusion DNA polymerase. PCR fragments were gel-purified and subjected to sequencing with CMV2, JNT082, JNT097 and JNT098 as primers (FIG. 22). Similarly, the coding region of kappa light chain was amplified using CMV2 and JNT026 (FIG. 22) and gel-purified DNA fragments were subjected to sequencing with CMV2, JNT026, JNT080 and JNT084 as primers (FIG. 22). The obtained sequences for heavy and light chain coding regions matched perfectly with the corresponding sequences in the expression vector for each of NS0-Hu33E10-4 5D3, NS0-Hu33E10-5 1E5 and NS0-Hu33E10-6 I-15 stable transfectants. The sequences for the entire coding region of gamma-1 heavy chain consisting of Hu33E10 VH7 and VH7.8 are shown FIGS. 23 and 24, respectively. The sequences for the entire coding region of kappa light chain consisting of Hu33E10 VL6 and VLv2 are shown FIGS. 25 and 26.

In addition, the authenticity of the VH and VL regions of Ch33E10 IgG1/κ antibody produced in NS0-Ch33E10 2C11 was confirmed by cDNA sequencing. Extraction of total RNA and cDNA synthesis was carried out as described above. The VH coding region was amplified by PCR using CMV2 and JNT082 as primers and Phusion polymerase. PCR fragments were gel-purified and subjected to sequencing with CMV2 and JNT082 as primers. Similarly, the VL coding region was amplified using CMV2 and JNT026 and gel-purified DNA fragments were subjected to sequencing with CMV2 and JNT026 as primers. The obtained nucleotide sequences of the VH and VL regions matched perfectly with the corresponding sequences in the pCh33E10 expression vector (FIGS. 3 and 4, respectively).

6.9. Conclusion

The affinity of Hu33E10-VH7/VLv2 IgG1/κ to hOPN5-BSA was determined to be within 3-fold of that of Ch33E10 IgG1/κ.

6.10. Cell Adhesion Inhibition Assay

FIG. 27 shows humanized anti-OPN antibodies inhibited the adhesion of MDA-MB-435S to hOPN5-BSA. MDA-MB-435S human breast cancer cell line was obtained from the American Type Culture Collection (ATCC), and cultured in DMEM supplement with 10% fetal bovine serum. The 96-well plates were coated with hOPN5-BSA (2 μg/ml) for 1 h at 37° C., followed by treatment with 0.5% BSA for 1 h at room temperature. Human immunoglobulin G1 kappa, Ch33E10, Hu33E10-VH7.8/VL6 (EJ3-1-1), Hu33E10-VH7/VL6 (E3-1), Hu33E10-VH7/VLv2 (SP-2), and mouse 33E10 antibodies were dissolved in 0.25% BSA, DMEM, and treated at various concentrations, started at 100 μg/ml and serial 2-fold dilutions, for 20 min at 37° C. $2 \times 10^4$ MDA-MB-435S cells were added to each well. After 1 h incubation at 37° C., the medium was removed and washed twice with warm PBS (warmed up to 37° C.) gently. The adherent cells were fixed and stained with 0.5% crystal violet dissolved in 20% methanol, and lysed with 20% acetic acid. The absorbance was measured at 590 nm. The inhibition ratio was normalized with the absorbance without adding antibody.

7. DEPOSITION

The hybridomas designated herein as 33E10 and 35B6 producing mouse anti-RGD monoclonal antibodies were deposited on Oct. 27, 2005 with International Patent Organism Depositary, National Institute of Advanced Industrial Science and Technology, located at Central 6, 1-1-1 Higashi, Tsukuba, Ibaraki (postal code: 305-8566) in accordance with the Budapest Treaty on the Deposit of Microorganisms, and accorded Accession Nos. FERM BP-10440 and FERM BP-10441, respectively, all of which are incorporated herein by reference in their entireties.

8. INDUSTRIAL APPLICABILITY

The humanized monoclonal antibodies of the present invention inhibit the function of RGD proteins to exhibit therapeutic effects on cancer, e.g., the growth or metastasis of cancer cells, and an inflammatory disease, e.g., rheumatoid arthritis, osteoarthritis, hepatitis, bronchial asthma, fibrosis, diabetes mellitus, cancer metastasis, arteriosclerosis, multiple sclerosis, granuloma, an inflammatory bowel disease (ulcerative colitis and Crohn's disease), an autoimmune disease, and the like. The pharmaceutical composition comprising both the anti-RGD antibody and anti-integrin antibody of the present invention exerts more improved therapeutic effects on cancer and an inflammatory disease.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that the present invention be limited only by the claims and the equivalents thereof.

SEQUENCE LISTING

```
<160> NUMBER OF SEQ ID NOS: 100

<210> SEQ ID NO 1
<211> LENGTH: 5
<212> TYPE: PRT
<213> ORGANISM: Homo sapiens

<400> SEQUENCE: 1

Asp Tyr Tyr Met Ile
1               5

<210> SEQ ID NO 2
<211> LENGTH: 19
<212> TYPE: PRT
```

<210> SEQ ID NO 2
<211> LENGTH: 18 (not shown, but part of header omitted)
<213> ORGANISM: Homo sapiens

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 3
<212> TYPE: PRT
<213> ORGANISM: Homo sapiens

<400> SEQUENCE: 3

Gly Ala Tyr
1

<210> SEQ ID NO 4
<211> LENGTH: 16
<212> TYPE: PRT
<213> ORGANISM: Homo sapiens

<400> SEQUENCE: 4

Arg Ser Ser Gln Ser Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Homo sapiens

<400> SEQUENCE: 5

Arg Val Ser Asn Arg Phe Ser
1               5

<210> SEQ ID NO 6
<211> LENGTH: 9
<212> TYPE: PRT
<213> ORGANISM: Homo sapiens

<400> SEQUENCE: 6

Phe Gln Gly Ser Phe Val Pro Trp Thr
1               5

<210> SEQ ID NO 7
<211> LENGTH: 434
<212> TYPE: DNA
<213> ORGANISM: Homo sapiens

<400> SEQUENCE: 7

```
actagtacca ccatgaagtt gtggctgaac tggattttcc ttgtaacact tttaaatggt      60
ttccagtgtg aagtgcagct ggtggagtct ggaggaggct tggtacagcc tgggggttct     120
ctgagactct cctgtgcagc ttctggattc accttcactg attactacat gatctgggtc     180
cgccaggctc cagggaaggg acttgagtgg ttgggtttta ttagaaacaa agctaatggt     240
tacacaacag agtacagtgc atctgtgaag ggtcggttca ccatctccag agataatgcc     300
aagaacatcc tctatcttca aatgaattcc ctgagagctg aggacacggc cgtgtattac     360
tgtgcaaggg gcgcttactg gggccaaggg actatggtca ctgtctcttc aggtaagatg     420
ggctttccaa gctt                                                       434
```

<210> SEQ ID NO 8
<211> LENGTH: 133

<212> TYPE: PRT
<213> ORGANISM: Homo sapiens

<400> SEQUENCE: 8

```
Met Lys Leu Trp Leu Asn Trp Ile Phe Leu Val Thr Leu Leu Asn Gly
1               5                   10                  15

Phe Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Ile Trp Val Arg Gln Ala Pro Gly Lys Gly Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ala
                85                  90                  95

Lys Asn Ile Leu Tyr Leu Gln Met Asn Ser Leu Arg Ala Glu Asp Thr
            100                 105                 110

Ala Val Tyr Tyr Cys Ala Arg Gly Ala Tyr Trp Gly Gln Gly Thr Met
        115                 120                 125

Val Thr Val Ser Ser
        130
```

<210> SEQ ID NO 9
<211> LENGTH: 434
<212> TYPE: DNA
<213> ORGANISM: Homo sapiens

<400> SEQUENCE: 9

```
actagtacca ccatgaagtt gtggctgaac tggatttttcc ttgtaacact tttaaatggt    60
ttccagtgtg aagtgcagct ggtggagtct ggaggaggct tggtacagcc tggggggttct   120
ctgagactct cctgtgcagc ttctggattc accttcactg attactacat gatctgggtc   180
cgccaggctc cagggaaggg acttgagtgg ttgggtttta ttagaaacaa agctaatggt   240
tacacaacag agtacagtgc atctgtgaag gtcggttca ccatctccag agataatgcc   300
aagagcatcc tctatcttca aatgaattcc ctgagagctg aggacacggc cgtgtattac   360
tgtgcaaggg gcgcttactg gggccaaggg actatggtca ctgtctcttc aggtaagatg   420
ggctttccaa gctt                                                     434
```

<210> SEQ ID NO 10
<211> LENGTH: 133
<212> TYPE: PRT
<213> ORGANISM: Homo sapiens

<400> SEQUENCE: 10

```
Met Lys Leu Trp Leu Asn Trp Ile Phe Leu Val Thr Leu Leu Asn Gly
1               5                   10                  15

Phe Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Ile Trp Val Arg Gln Ala Pro Gly Lys Gly Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ala
```

```
                85                  90                  95
Lys Ser Ile Leu Tyr Leu Gln Met Asn Ser Leu Arg Ala Glu Asp Thr
            100                 105                 110

Ala Val Tyr Tyr Cys Ala Arg Gly Ala Tyr Trp Gly Gln Gly Thr Met
        115                 120                 125

Val Thr Val Ser Ser
    130

<210> SEQ ID NO 11
<211> LENGTH: 434
<212> TYPE: DNA
<213> ORGANISM: Homo sapiens

<400> SEQUENCE: 11
actagtacca ccatgaagtt gtggctgaac tggattttcc ttgtaacact tttaaatggt      60
ttccagtgtg aagtgcagct ggtggagtct ggaggaggct tggtacagcc tggggggttct    120 ctgagactct cctgtgcagc ttctggattc accttcactg attactacat gatctgggtc    180
cgccaggctc cagggaaggg acttgagtgg ttgggtttta ttagaaacaa agctaatggt    240
tacacaacag agtacagtgc atctgtgaag ggtcggttca ccatctccag agataattcc    300
aagagcatcc tctatcttca aatgaattcc ctgagagctg aggacacggc cgtgtattac    360
tgtgcaaggg gcgcttactg gggccaaggg actatggtca ctgtctcttc aggtaagatg    420
ggctttccaa gctt                                                       434

<210> SEQ ID NO 12
<211> LENGTH: 133
<212> TYPE: PRT
<213> ORGANISM: Homo sapiens

<400> SEQUENCE: 12

Met Lys Leu Trp Leu Asn Trp Ile Phe Leu Val Thr Leu Leu Asn Gly
1               5                   10                  15

Phe Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Ile Trp Val Arg Gln Ala Pro Gly Lys Gly Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Lys Ser Ile Leu Tyr Leu Gln Met Asn Ser Leu Arg Ala Glu Asp Thr
            100                 105                 110

Ala Val Tyr Tyr Cys Ala Arg Gly Ala Tyr Trp Gly Gln Gly Thr Met
        115                 120                 125

Val Thr Val Ser Ser
    130

<210> SEQ ID NO 13
<211> LENGTH: 431
<212> TYPE: DNA
<213> ORGANISM: Homo sapiens

<400> SEQUENCE: 13
gctagcacca ccatgaggac ccctgctcag tttcttggaa tcttgttgct ctggtttcca     60
```

```
ggaatcaaat gtgatattgt gatgacccaa tctccactct ccctgcctgt cactcctgga    120
gagccagcct ccatctcttg cagatctagt cagagcattg tacatagtaa tggaaacacc    180
tatttagaat ggtacctgca gaaaccaggc cagtctccac agctcctgat ctacagagtt    240
tccaaccgat tttctggggt cccagacagg ttcagtggca gtggatcagg gacagatttc    300
acactcaaga tcagcagagt ggaggctgag gatgtcggag tttattactg ctttcaaggt    360
tcatttgttc cgtggacgtt cggtcaaggc accaaagtgg aaatcaaacg tgagtagaat    420
ttaaagaatt c                                                        431

<210> SEQ ID NO 14
<211> LENGTH: 143
<212> TYPE: PRT
<213> ORGANISM: Homo sapiens

<400> SEQUENCE: 14

Met Arg Thr Pro Ala Gln Phe Leu Gly Ile Leu Leu Leu Trp Phe Pro
1               5                   10                  15

Gly Ile Lys Cys Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Ile Val His Ser Asn Gly Asn Thr Tyr Leu Glu Trp Tyr Leu Gln Lys
    50                  55                  60

Pro Gly Gln Ser Pro Gln Leu Leu Ile Tyr Arg Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Gly Ser Phe Val Pro Trp Thr Phe Gly Gln Gly Thr Lys
        115                 120                 125

Val Glu Ile Lys Thr Thr Ala Ala Gly Ala Ala Thr Thr Cys
    130                 135                 140

<210> SEQ ID NO 15
<211> LENGTH: 431
<212> TYPE: DNA
<213> ORGANISM: Homo sapiens

<400> SEQUENCE: 15
gctagcacca ccatgaggac ccctgctcag tttcttggaa tcttgttgct ctggtttcca     60
ggaatcaaat gtgatatcgt gatgacccaa tctccagact ccctggctgt cagtcttgga    120
gagagggcca ccatctcttg cagatctagt cagagcattg tacatagtaa tggaaacacc    180
tatttagaat ggtacctgca gaaaccaggc cagcctccaa agctcctgat ctacagagtt    240
tccaaccgat tttctggggt cccagacagg ttcagtggca gtggatcagg gacagatttc    300
acactcacca tcagcagcct gcaggctgag gatgtggcag tttattactg ctttcaaggt    360
tcatttgttc cgtggacgtt cggtcaaggc accaaggtgg aaatcaaacg tgagtagaat    420
ttaaagaatt c                                                        431

<210> SEQ ID NO 16
<211> LENGTH: 132
<212> TYPE: PRT
<213> ORGANISM: Homo sapiens

<400> SEQUENCE: 16
```

-continued

```
Met Arg Thr Pro Ala Gln Phe Leu Gly Ile Leu Leu Leu Trp Phe Pro
1               5                   10                  15

Gly Ile Lys Cys Asp Ile Val Met Thr Gln Ser Pro Asp Ser Leu Ala
            20                  25                  30

Val Ser Leu Gly Glu Arg Ala Thr Ile Ser Cys Arg Ser Gln Ser
        35                  40                  45

Ile Val His Ser Asn Gly Asn Thr Tyr Leu Glu Trp Tyr Leu Gln Lys
    50                  55                  60

Pro Gly Gln Pro Pro Lys Leu Leu Ile Tyr Arg Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
            100                 105                 110

Cys Phe Gln Gly Ser Phe Val Pro Trp Thr Phe Gly Gln Gly Thr Lys
            115                 120                 125

Val Glu Ile Lys
    130
```

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
gaaccgtcag atcgcctgga gacg                                          24

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tgaaagatga gctggaggac                                               20

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
gaactgtggc tgcaccatc                                                19

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
ctttcttgtc caccttggtg                                               20

<210> SEQ ID NO 21
<211> LENGTH: 20
<212> TYPE: DNA

-continued

<213> ORGANISM: Artificial Sequence
<220> FEATURE:
<223> OTHER INFORMATION: primer

<400> SEQUENCE: 21
gttgaagctc tttgtgacgg                                          20

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
gctgtcctac agtcctcag                                           19

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23
acgtgccaag catcctcg                                            18

<210> SEQ ID NO 24
<211> LENGTH: 1392
<212> TYPE: DNA
<213> ORGANISM: Homo sapiens

<400> SEQUENCE: 24
atgaagttgt ggctgaactg gattttcctt gtaacacttt taaatggttt ccagtgtgaa      60
gtgcagctgg tggagtctgg aggaggcttg gtacagcctg ggggttctct gagactctcc    120
tgtgcagctt ctggattcac cttcactgat tactacatga tctgggtccg ccaggctcca    180
gggaagggac ttgagtggtt gggttttatt agaaacaaag ctaatggtta cacaacagag    240
tacagtgcat ctgtgaaggg tcggttcacc atctccagag ataatgccaa gagcatcctc    300
tatcttcaaa tgaactccct gagagctgag gacacggccg tgtattactg tgcaaggggc    360
gcttactggg gccaagggac tatggtcact gtctcttcag cctccaccaa gggcccatcg    420
gtcttccccc tggcaccctc ctccaagagc acctctgggg gcacagcggc cctgggctgc    480
ctggtcaagg actacttccc cgaaccggtg acggtgtcgt ggaactcagg cgccctgacc    540
agcggcgtgc acaccttccc ggctgtccta cagtcctcag gactctactc cctcagcagc    600
gtggtgaccg tgccctccag cagcttgggc acccagacct acatctgcaa cgtgaatcac    660
aagcccagca acaccaaggt ggacaagaaa gttgagccca atcttgtga caaaactcac    720 acatgcccac cgtgcccagc acctgaactc ctggggggac cgtcagtctt cctcttcccc    780
ccaaaaccca aggacaccct catgatctcc cggacccctg aggtcacatg cgtggtggtg    840
gacgtgagcc acgaagaccc tgaggtcaag ttcaactggt acgtggacgg cgtggaggtg    900
cataatgcca agacaaagcc gcgggaggag cagtacaaca gcacgtaccg tgtggtcagc    960
gtcctcaccg tcctgcacca ggactggctg aatggcaagg agtacaagtg caaggtctcc   1020
aacaaagccc tcccagcccc catcgagaaa accatctcca aagccaaagg gcagccccga   1080
gaaccacagg tgtacaccct gcccccatcc cgggatgagc tgaccaagaa ccaggtcagc   1140
ctgacctgcc tggtcaaagg cttctatccc agcgacatcg ccgtggagtg ggagagcaat   1200

-continued

```
gggcagccgg agaacaacta caagaccacg cctcccgtgc tggactccga cggctccttc    1260
ttcctctaca gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaat ga                                                        1392
```

<210> SEQ ID NO 25
<211> LENGTH: 463
<212> TYPE: PRT
<213> ORGANISM: Homo sapiens

<400> SEQUENCE: 25

```
Met Lys Leu Trp Leu Asn Trp Ile Phe Leu Val Thr Leu Leu Asn Gly
1               5                   10                  15

Phe Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Ile Trp Val Arg Gln Ala Pro Gly Lys Gly Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ala
                85                  90                  95

Lys Ser Ile Leu Tyr Leu Gln Met Asn Ser Leu Arg Ala Glu Asp Thr
            100                 105                 110

Ala Val Tyr Tyr Cys Ala Arg Gly Ala Tyr Trp Gly Gln Gly Thr Met
        115                 120                 125

Val Thr Val Ser Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
```

```
              340                 345                 350
Ser Lys Ala Lys Gly Gln Pro Arg Glu Pro Gln Val Tyr Thr Leu Pro
            355                 360                 365
Pro Ser Arg Asp Glu Leu Thr Lys Asn Gln Val Ser Leu Thr Cys Leu
        370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Lys Leu Thr Val Asp Lys Ser Arg
            420                 425                 430
Trp Gln Gln Gly Asn Val Phe Ser Cys Ser Val Met His Glu Ala Leu
        435                 440                 445
His Asn His Tyr Thr Gln Lys Ser Leu Ser Leu Ser Pro Gly Lys
    450                 455                 460

<210> SEQ ID NO 26
<211> LENGTH: 1392
<212> TYPE: DNA
<213> ORGANISM: Homo sapiens

<400> SEQUENCE: 26
atgaagttgt ggctgaactg gattttcctt gtaacacttt taaatggttt ccagtgtgaa      60
gtgcagctgg tggagtctgg aggaggcttg gtacagcctg ggggttctct gagactctcc     120
tgtgcagctt ctggattcac cttcactgat tactacatga tctgggtccg ccaggctcca     180
gggaagggac ttgagtggtt gggttttatt agaaacaaag ctaatggtta cacaacagag     240
tacagtgcat ctgtgaaggg tcggttcacc atctccagag ataattccaa gagcatcctc     300
tatcttcaaa tgaactccct gagagctgag gacacggccg tgtattactg tgcaaggggc     360
gcttactggg gccaagggac tatggtcact gtctcttcag cctccaccaa gggcccatcg     420
gtcttccccc tggcaccctc ctccaagagc acctctgggg cacagcggc cctgggctgc     480 ctggtcaagg actacttccc cgaaccggtg acggtgtcgt ggaactcagg cgccctgacc     540
agcggcgtgc acaccttccc ggctgtccta cagtcctcag gactctactc cctcagcagc     600
gtggtgaccg tgccctccag cagcttgggc acccagacct acatctgcaa cgtgaatcac     660
aagcccagca acaccaaggt ggacaagaaa gttgagccca atcttgtga caaaactcac     720 acatgcccac cgtgcccagc acctgaactc ctggggggac cgtcagtctt cctcttcccc     780
ccaaaaccca aggacaccct catgatctcc cggacccctg aggtcacatg cgtggtggtg     840
gacgtgagcc acgaagaccc tgaggtcaag ttcaactggt acgtggacgg cgtggaggtg     900
cataatgcca agacaaagcc gcgggaggag cagtacaaca gcacgtaccg tgtggtcagc     960
gtcctcaccg tcctgcacca ggactggctg aatggcaagg agtacaagtg caaggtctcc    1020
aacaaagccc tcccagcccc catcgagaaa accatctcca aagccaaagg gcagccccga    1080
gaaccacagg tgtacaccct gcccccatcc cgggatgagc tgaccaagaa ccaggtcagc    1140
ctgacctgcc tggtcaaagg cttctatccc agcgacatcg ccgtggagtg ggagagcaat    1200
gggcagccgg agaacaacta caagaccacg cctcccgtgc tggactccga cggctccttc    1260
ttcctctaca gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaat ga                                                         1392
```

```
<210> SEQ ID NO 27
<211> LENGTH: 463
<212> TYPE: PRT
<213> ORGANISM: Homo sapiens

<400> SEQUENCE: 27

Met Lys Leu Trp Leu Asn Trp Ile Phe Leu Val Thr Leu Leu Asn Gly
1               5                   10                  15

Phe Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Ile Trp Val Arg Gln Ala Pro Gly Lys Gly Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Lys Ser Ile Leu Tyr Leu Gln Met Asn Ser Leu Arg Ala Glu Asp Thr
            100                 105                 110

Ala Val Tyr Tyr Cys Ala Arg Gly Ala Tyr Trp Gly Gln Gly Thr Met
        115                 120                 125

Val Thr Val Ser Ser Ala Ser Thr Lys Gly Pro Ser Val Phe Pro Leu
130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
```

```
385                 390                 395                 400
Gly Gln Pro Glu Asn Asn Tyr Lys Thr Thr Pro Val Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
        450                 455                 460

<210> SEQ ID NO 28
<211> LENGTH: 720
<212> TYPE: DNA
<213> ORGANISM: Homo sapiens

<400> SEQUENCE: 28
atgaggaccc ctgctcagtt tcttggaatc ttgttgctct ggtttccagg aatcaaatgt      60
gatattgtga tgacccaatc tccactctcc ctgcctgtca ctcctggaga gccagcctcc     120
atctcttgca gatctagtca gagcattgta catagtaatg aaacacccta tttagaatgg     180
tacctgcaga aaccaggcca gtctccacag ctcctgatct acagagtttc caaccgattt     240
tctggggtcc cagacaggtt cagtggcagt ggatcaggga cagatttcac actcaagatc     300
agcagagtgg aggctgagga tgtcggagtt tattactgct tcaaggttc atttgttccg      360 tggacgttcg gtcaaggcac caaagtggaa atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgttag     720

<210> SEQ ID NO 29
<211> LENGTH: 239
<212> TYPE: PRT
<213> ORGANISM: Homo sapiens

<400> SEQUENCE: 29

Met Arg Thr Pro Ala Gln Phe Leu Gly Ile Leu Leu Leu Trp Phe Pro
1               5                   10                  15

Gly Ile Lys Cys Asp Ile Val Met Thr Gln Ser Pro Leu Ser Leu Pro
                20                  25                  30

Val Thr Pro Gly Glu Pro Ala Ser Ile Ser Cys Arg Ser Ser Gln Ser
            35                  40                  45

Ile Val His Ser Asn Gly Asn Thr Tyr Leu Glu Trp Tyr Leu Gln Lys
        50                  55                  60

Pro Gly Gln Ser Pro Gln Leu Leu Ile Tyr Arg Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Gly Ser Phe Val Pro Trp Thr Phe Gly Gln Gly Thr Lys
        115                 120                 125

Val Glu Ile Lys Arg Thr Val Ala Ala Pro Ser Val Phe Ile Phe Pro
    130                 135                 140
```

```
Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 30
<211> LENGTH: 720
<212> TYPE: DNA
<213> ORGANISM: Homo sapiens

<400> SEQUENCE: 30
atgaggaccc ctgctcagtt tcttggaatc ttgttgctct ggtttccagg aatcaaatgt      60
gatatcgtga tgacccaatc tccagactcc ctggctgtca gtcttggaga gagggccacc     120
atctcttgca gatctagtca gagcattgta catagtaatg aaacacccta tttagaatgg     180
tacctgcaga aaccaggcca gcctccaaag ctcctgatct acagagtttc aaccgattt      240 tctggggtcc cagacaggtt cagtggcagt ggatcaggga cagatttcac actcaccatc     300
agcagcctgc aggctgagga tgtggcagtt tattactgct tcaaggttc atttgttccg      360 tggacgttcg gtcaaggcac caaggtggaa atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660 gtcaccccatc agggcctgag ctcgcccgtc acaaagagct tcaacagggg agagtgttag     720

<210> SEQ ID NO 31
<211> LENGTH: 239
<212> TYPE: PRT
<213> ORGANISM: Homo sapiens

<400> SEQUENCE: 31

Met Arg Thr Pro Ala Gln Phe Leu Gly Ile Leu Leu Leu Trp Phe Pro
1               5                   10                  15

Gly Ile Lys Cys Asp Ile Val Met Thr Gln Ser Pro Asp Ser Leu Ala
            20                  25                  30

Val Ser Leu Gly Glu Arg Ala Thr Ile Ser Cys Arg Ser Ser Gln Ser
        35                  40                  45

Ile Val His Ser Asn Gly Asn Thr Tyr Leu Glu Trp Tyr Leu Gln Lys
    50                  55                  60

Pro Gly Gln Pro Pro Lys Leu Leu Ile Tyr Arg Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
            100                 105                 110
```

```
Cys Phe Gln Gly Ser Phe Val Pro Trp Thr Phe Gly Gln Gly Thr Lys
            115                 120                 125
Val Glu Ile Lys Arg Thr Val Ala Ala Pro Ser Val Phe Ile Phe Pro
130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
                165                 170                 175
Asn Ala Leu Gln Ser Gly Asn Ser Gln Glu Ser Val Thr Glu Gln Asp
            180                 185                 190
Ser Lys Asp Ser Thr Tyr Ser Leu Ser Ser Thr Leu Thr Leu Ser Lys
        195                 200                 205
Ala Asp Tyr Glu Lys His Lys Val Tyr Ala Cys Glu Val Thr His Gln
210                 215                 220
Gly Leu Ser Ser Pro Val Thr Lys Ser Phe Asn Arg Gly Glu Cys
225                 230                 235
```

<210> SEQ ID NO 32
<211> LENGTH: 112
<212> TYPE: PRT
<213> ORGANISM: Mus musculus

<400> SEQUENCE: 32

```
Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Arg Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser Phe Val Pro Trp Thr Phe Gly Gly Gly Thr Lys Leu Glu Ile Lys
            100                 105                 110
```

<210> SEQ ID NO 33
<211> LENGTH: 112
<212> TYPE: PRT
<213> ORGANISM: Homo sapiens

<400> SEQUENCE: 33

```
Asp Ile Val Met Thr Gln Ser Pro Asp Ser Leu Ala Val Ser Leu Gly
1               5                   10                  15
Glu Arg Ala Thr Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Pro
        35                  40                  45
Pro Lys Leu Leu Ile Tyr Arg Val Ser Asn Arg Phe Ser Gly Val Pro
    50                  55                  60
Asp Arg Phe Ser Gly Ser Gly Ser Gly Thr Asp Phe Thr Leu Thr Ile
65                  70                  75                  80
Ser Ser Leu Gln Ala Glu Asp Val Ala Val Tyr Tyr Cys Phe Gln Gly
                85                  90                  95
Ser Phe Val Pro Trp Thr Phe Gly Gln Gly Thr Lys Val Glu Ile Lys
```

<210> SEQ ID NO 34
<211> LENGTH: 399
<212> TYPE: DNA
<213> ORGANISM: Mus musculus

<400> SEQUENCE: 34

```
atgaagttgt ggctgaactg gattttcctt gtaacacttt taaatggttt ccagtgtgag    60
gtgaagctgg tggagtctgg aggaggcttg gtacagcctg ggggttctct gagtctctcc   120
tgtgcagctt ctggattcac cttcactgat tactacatga tctgggtccg ccagcctcca   180
gggaaggcac ttgagtggtt gggttttatt agaaacaaag ctaatggtta cacaacagag   240
tacagtgcat ctgtgaaggg tcggttcacc atctccagag ataattccca aagcatcctc   300
tatcttcaaa tgaatgccct gagagctgag gacagtgcca cttattactg tgcaggggg   360
gcttactggg gccaagggac tctggtcact gtctctgca                          399
```

<210> SEQ ID NO 35
<211> LENGTH: 133
<212> TYPE: PRT
<213> ORGANISM: Mus musculus

<400> SEQUENCE: 35

```
Met Lys Leu Trp Leu Asn Trp Ile Phe Leu Val Thr Leu Leu Asn Gly
 1               5                  10                  15
Phe Gln Cys Glu Val Lys Leu Val Glu Ser Gly Gly Gly Leu Val Gln
             20                  25                  30
Pro Gly Gly Ser Leu Ser Leu Ser Cys Ala Ala Ser Gly Phe Thr Phe
         35                  40                  45
Thr Asp Tyr Tyr Met Ile Trp Val Arg Gln Pro Pro Gly Lys Ala Leu
     50                  55                  60
Glu Trp Leu Gly Phe Ile Arg Asn Lys Ala Asn Gly Tyr Thr Thr Glu
 65                  70                  75                  80
Tyr Ser Ala Ser Val Lys Gly Arg Phe Thr Ile Ser Arg Asp Asn Ser
                 85                  90                  95
Gln Ser Ile Leu Tyr Leu Gln Met Asn Ala Leu Arg Ala Glu Asp Ser
            100                 105                 110
Ala Thr Tyr Tyr Cys Ala Arg Gly Ala Tyr Trp Gly Gln Gly Thr Leu
        115                 120                 125
Val Thr Val Ser Ala
    130
```

<210> SEQ ID NO 36
<211> LENGTH: 393
<212> TYPE: DNA
<213> ORGANISM: Mus musculus

<400> SEQUENCE: 36

```
atgaagttgc ctgttaggct gttggtgctg atgttctgga ttcctgcttc cagcagtgat    60
gttttgatga cccaaactcc actctccctg cctgtcagtc ttggagatca agcctccatc   120
tcttgcagat ctagtcagag cattgtacat agtaatggaa acacctattt agaatggtac   180
ctgcagaaac caggccagtc tccaaagctc ctgatctaca gagtttccaa ccgatttttct  240
ggggtcccag acaggttcag tggcagtgga tcaggacag atttcacact caagatcagc   300
agagtggagg ctgaggatct gggagtttat tactgctttc aaggttcatt tgttccgtgg   360
acgttcggtg gaggcaccaa gctggaaatc aaa                               393
```

<210> SEQ ID NO 37
<211> LENGTH: 131
<212> TYPE: PRT
<213> ORGANISM: Mus musculus

<400> SEQUENCE: 37

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Arg Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Phe Val Pro Trp Thr Phe Gly Gly Gly Thr Lys Leu
        115                 120                 125

Glu Ile Lys
        130

<210> SEQ ID NO 38
<211> LENGTH: 433
<212> TYPE: DNA
<213> ORGANISM: Mus musculus

<400> SEQUENCE: 38
actagtacca ccatgaagtt gtggctgaac tggattttcc ttgtaacact tttaaatggt      60
ttccagtgtg aggtgaagct ggtggagtct ggaggaggct tggtacagcc tgggggttct     120
ctgagtctct cctgtgcagc ttctggattc accttcactg attactacat gatctgggtc     180
cgccagcctc cagggaaggc acttgagtgg ttgggtttta ttagaaacaa agctaatggt     240
tacacaacag agtacagtgc atctgtgaag ggtcggttca ccatctccag agataattcc     300
caaagcatcc tctatcttca aatgaatgcc ctgagagctg aggacagtgc cacttattac     360
tgtgcaaggg gggcttactg gggccaaggg actctggtca ctgtctctgc aggtgagtcc     420
taacttcaag ctt                                                       433

<210> SEQ ID NO 39
<211> LENGTH: 133
<212> TYPE: PRT
<213> ORGANISM: Mus musculus

<400> SEQUENCE: 39

Met Lys Leu Trp Leu Asn Trp Ile Phe Leu Val Thr Leu Leu Asn Gly
1               5                   10                  15

Phe Gln Cys Glu Val Lys Leu Val Glu Ser Gly Gly Gly Leu Val Gln
            20                  25                  30

Pro Gly Gly Ser Leu Ser Leu Ser Cys Ala Ala Ser Gly Phe Thr Phe
        35                  40                  45

Thr Asp Tyr Tyr Met Ile Trp Val Arg Gln Pro Pro Gly Lys Ala Leu
    50                  55                  60

-continued

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Ala Leu Arg Ala Glu Asp Ser
            100                 105                 110

Ala Thr Tyr Tyr Cys Ala Arg Gly Ala Tyr Trp Gly Gln Gly Thr Leu
        115                 120                 125

Val Thr Val Ser Ala
    130

<210> SEQ ID NO 40
<211> LENGTH: 428
<212> TYPE: DNA
<213> ORGANISM: Mus musculus

<400> SEQUENCE: 40
gctagcacca ccatgaagtt gcctgttagg ctgttggtgc tgatgttctg gattcctgct      60
tccagcagtg atgttttgat gacccaaact ccactctccc tgcctgtcag tcttggagat    120
caagcctcca tctcttgcag atctagtcag agcattgtac atagtaatgg aaacacctat    180
ttagaatggt acctgcagaa accaggccag tctccaaagc tcctgatcta cagagtttcc    240
aaccgatttt ctggggtccc agacaggttc agtggcagtg gatcagggac agatttcaca    300
ctcaagatca gcagagtgga ggctgaggat ctgggagttt attactgctt tcaaggttca    360
tttgttccgt ggacgttcgg tggaggcacc aagctggaaa tcaaacgtaa gtagaatcca    420
aagaattc                                                             428

<210> SEQ ID NO 41
<211> LENGTH: 131
<212> TYPE: PRT
<213> ORGANISM: Mus musculus

<400> SEQUENCE: 41

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Arg Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Phe Val Pro Trp Thr Phe Gly Gly Gly Thr Lys Leu
        115                 120                 125

Glu Ile Lys
    130

<210> SEQ ID NO 42
<211> LENGTH: 114
<212> TYPE: PRT
<213> ORGANISM: Mus musculus

<400> SEQUENCE: 42

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ile Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Gly Ala Tyr Trp Gly Gln Gly Thr Leu Val Thr Val
            100                 105                 110

Ser Ala

<210> SEQ ID NO 43
<211> LENGTH: 114
<212> TYPE: PRT
<213> ORGANISM: Homo sapiens

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ile Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Gly Ala Tyr Trp Gly Gln Gly Thr Met Val Thr Val
            100                 105                 110

Ser Ser

<210> SEQ ID NO 44
<211> LENGTH: 112
<212> TYPE: PRT
<213> ORGANISM: Mus musculus

<400> SEQUENCE: 44

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly

```
                85                  90                  95
Ser Phe Val Pro Trp Thr Phe Gly Gly Gly Thr Lys Leu Glu Ile Lys
            100                 105                 110
```

<210> SEQ ID NO 45
<211> LENGTH: 112
<212> TYPE: PRT
<213> ORGANISM: Homo sapiens

<400> SEQUENCE: 45

```
Asp Ile Val Met Thr Gln Ser Pro Leu Ser Leu Pro Val Thr Pro Gly
1               5                   10                  15
Glu Pro Ala Ser Ile Ser Cys Arg Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Gln Leu Leu Ile Tyr Arg Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser Phe Val Pro Trp Thr Phe Gly Gln Gly Thr Lys Val Glu Ile Lys
            100                 105                 110
```

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
gggactagta ccaccatgaa g                                           21

<210> SEQ ID NO 47
<211> LENGTH: 54
<212> TYPE: DNA
<213> ORGANISM: Artificial Sequence
<220> FEATURE:
<223> OTHER INFORMATION: primer

<400> SEQUENCE: 47
gggactagta ccaccatgaa gttgtggctg aactggattt ccttgtaac actt        54

<210> SEQ ID NO 48
<211> LENGTH: 51
<212> TYPE: DNA
<213> ORGANISM: Artificial Sequence
<220> FEATURE:
<223> OTHER INFORMATION: primer

<400> SEQUENCE: 48
cagctgcact tcacactgga aaccatttaa aagtgttaca aggaaaatcc a          51

<210> SEQ ID NO 49
<211> LENGTH: 51
<212> TYPE: DNA
<213> ORGANISM: Artificial Sequence
<220> FEATURE:
<223> OTHER INFORMATION: primer

<400> SEQUENCE: 49
ttccagtgtg aagtgcagct ggtggagtct ggaggaggct tggtacagcc t        51

<210> SEQ ID NO 50
<211> LENGTH: 51
<212> TYPE: DNA
<213> ORGANISM: Artificial Sequence
<220> FEATURE:
<223> OTHER INFORMATION: primer

<400> SEQUENCE: 50
agctgcacag gagagtctca gagaaccccc aggctgtacc aagcctcctc c         51

<210> SEQ ID NO 51
<211> LENGTH: 51
<212> TYPE: DNA
<213> ORGANISM: Artificial Sequence
<220> FEATURE:
<223> OTHER INFORMATION: primer

<400> SEQUENCE: 51
ctgagactct cctgtgcagc ttctggattc accttcactg attactacat g         51

<210> SEQ ID NO 52
<211> LENGTH: 51
<212> TYPE: DNA
<213> ORGANISM: Artificial Sequence
<220> FEATURE:
<223> OTHER INFORMATION: primer

<400> SEQUENCE: 52
tcccttccct ggagcctggc ggacccagat catgtagtaa tcagtgaagg t         51

<210> SEQ ID NO 53
<211> LENGTH: 51
<212> TYPE: DNA
<213> ORGANISM: Artificial Sequence
<220> FEATURE:
<223> OTHER INFORMATION: primer

<400> SEQUENCE: 53
cgccaggctc cagggaaggg acttgagtgg ttgggtttta ttagaaacaa a         51

<210> SEQ ID NO 54
<211> LENGTH: 51
<212> TYPE: DNA
<213> ORGANISM: Artificial Sequence
<220> FEATURE:
<223> OTHER INFORMATION: primer

<400> SEQUENCE: 54
tgcactgtac tctgttgtgt aaccattagc tttgtttcta ataaaaccca a         51

<210> SEQ ID NO 55
<211> LENGTH: 51
<212> TYPE: DNA
<213> ORGANISM: Artificial Sequence
<220> FEATURE:
<223> OTHER INFORMATION: primer

<400> SEQUENCE: 55
tacacaacag agtacagtgc atctgtgaag ggtcggttca ccatctccag a         51

<210> SEQ ID NO 56
<211> LENGTH: 51
<212> TYPE: DNA
<213> ORGANISM: Artificial Sequence
<220> FEATURE:

<223> OTHER INFORMATION: primer

<400> SEQUENCE: 56
ttgaagatag agtgagttct tggcattatc tctggagatg gtgaaccgac c    51

<210> SEQ ID NO 57
<211> LENGTH: 51
<212> TYPE: DNA
<213> ORGANISM: Artificial Sequence
<220> FEATURE:
<223> OTHER INFORMATION: primer

<400> SEQUENCE: 57
aagaactcac tctatcttca aatgaactcc ctgagagctg aggacacggc c    51

<210> SEQ ID NO 58
<211> LENGTH: 51
<212> TYPE: DNA
<213> ORGANISM: Artificial Sequence
<220> FEATURE:
<223> OTHER INFORMATION: primer

<400> SEQUENCE: 58
ccagtaagcg ccccttgcac agtaatacac ggccgtgtcc tcagctctca g    51

<210> SEQ ID NO 59
<211> LENGTH: 51
<212> TYPE: DNA
<213> ORGANISM: Artificial Sequence
<220> FEATURE:
<223> OTHER INFORMATION: primer

<400> SEQUENCE: 59
tgtgcaaggg gcgcttactg gggccaaggg actatggtca ctgtctcttc a    51

<210> SEQ ID NO 60
<211> LENGTH: 47
<212> TYPE: DNA
<213> ORGANISM: Artificial Sequence
<220> FEATURE:
<223> OTHER INFORMATION: primer

<400> SEQUENCE: 60
gggaagcttg gaaagcccat cttacctgaa gagacagtga ccatagt    47

<210> SEQ ID NO 61
<211> LENGTH: 21
<212> TYPE: DNA
<213> ORGANISM: Artificial Sequence
<220> FEATURE:
<223> OTHER INFORMATION: primer

<400> SEQUENCE: 61
gggaagcttg gaaagcccat c    21

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
gggctagcac caccatgagg    20

<210> SEQ ID NO 63

```
<211> LENGTH: 53
<212> TYPE: DNA
<213> ORGANISM: Artificial Sequence
<220> FEATURE:
<223> OTHER INFORMATION: primer

<400> SEQUENCE: 63
gggctagcac caccatgagg acccctgctc agtttcttgg aatcttgttg ctc          53

<210> SEQ ID NO 64
<211> LENGTH: 51
<212> TYPE: DNA
<213> ORGANISM: Artificial Sequence
<220> FEATURE:
<223> OTHER INFORMATION: primer

<400> SEQUENCE: 64
cacaatatca catttgatac ctggaaacca gagcaacaag attccaagaa a            51

<210> SEQ ID NO 65
<211> LENGTH: 51
<212> TYPE: DNA
<213> ORGANISM: Artificial Sequence
<220> FEATURE:
<223> OTHER INFORMATION: primer

<400> SEQUENCE: 65
ggtatcaaat gtgatattgt gatgacccaa tctccactct ccctgcctgt c            51

<210> SEQ ID NO 66
<211> LENGTH: 51
<212> TYPE: DNA
<213> ORGANISM: Artificial Sequence
<220> FEATURE:
<223> OTHER INFORMATION: primer

<400> SEQUENCE: 66
gcaagagatg gaggctggct ctccaggagt gacaggcagg gagagtggag a            51

<210> SEQ ID NO 67
<211> LENGTH: 51
<212> TYPE: DNA
<213> ORGANISM: Artificial Sequence
<220> FEATURE:
<223> OTHER INFORMATION: primer

<400> SEQUENCE: 67
gagccagcct ccatctcttg cagatctagt cagagcattg tacatagtaa t            51

<210> SEQ ID NO 68
<211> LENGTH: 51
<212> TYPE: DNA
<213> ORGANISM: Artificial Sequence
<220> FEATURE:
<223> OTHER INFORMATION: primer

<400> SEQUENCE: 68
ctgcaggtac cattctaaat aggtgtttcc attactatgt acaatgctct g            51

<210> SEQ ID NO 69
<211> LENGTH: 51
<212> TYPE: DNA
<213> ORGANISM: Artificial Sequence
<220> FEATURE:
<223> OTHER INFORMATION: primer

<400> SEQUENCE: 69
```

```
tatttagaat ggtacctgca gaaaccaggc cagtctccac agctcctgat c          51
```

<210> SEQ ID NO 70
<211> LENGTH: 51
<212> TYPE: DNA
<213> ORGANISM: Artificial Sequence
<220> FEATURE:
<223> OTHER INFORMATION: primer

<400> SEQUENCE: 70

```
gaccccagaa aatcggttgg aaactctgta gatcaggagc tgtggagact g          51
```

<210> SEQ ID NO 71
<211> LENGTH: 51
<212> TYPE: DNA
<213> ORGANISM: Artificial Sequence
<220> FEATURE:
<223> OTHER INFORMATION: primer

<400> SEQUENCE: 71

```
tccaaccgat tttctggggt cccagacagg ttcagtggca gtggatcagg g          51
```

<210> SEQ ID NO 72
<211> LENGTH: 51
<212> TYPE: DNA
<213> ORGANISM: Artificial Sequence
<220> FEATURE:
<223> OTHER INFORMATION: primer

<400> SEQUENCE: 72

```
cactctgctg atcttgagtg tgaaatctgt ccctgatcca ctgccactga a          51
```

<210> SEQ ID NO 73
<211> LENGTH: 51
<212> TYPE: DNA
<213> ORGANISM: Artificial Sequence
<220> FEATURE:
<223> OTHER INFORMATION: primer

<400> SEQUENCE: 73

```
acactcaaga tcagcagagt ggaggctgag gatgtcggag tttattactg c          51
```

<210> SEQ ID NO 74
<211> LENGTH: 51
<212> TYPE: DNA
<213> ORGANISM: Artificial Sequence
<220> FEATURE:
<223> OTHER INFORMATION: primer

<400> SEQUENCE: 74

```
gaacgtccac ggaacaaatg aaccttgaaa gcagtaataa actccgacat c          51
```

<210> SEQ ID NO 75
<211> LENGTH: 57
<212> TYPE: DNA
<213> ORGANISM: Artificial Sequence
<220> FEATURE:
<223> OTHER INFORMATION: primer

<400> SEQUENCE: 75

```
tcatttgttc cgtggacgtt cggtcaaggc accaaagtgg aaatcaaacg tgagtag    57
```

<210> SEQ ID NO 76
<211> LENGTH: 37
<212> TYPE: DNA
<213> ORGANISM: Artificial Sequence
<220> FEATURE:

<223> OTHER INFORMATION: primer

<400> SEQUENCE: 76
ggggaattct ttaaattcta ctcacgtttg atttcca                                    37

<210> SEQ ID NO 77
<211> LENGTH: 20
<212> TYPE: DNA
<213> ORGANISM: Artificial Sequence
<220> FEATURE:
<223> OTHER INFORMATION: primer

<400> SEQUENCE: 77
ggggaattct ttaaattcta                                                       20

<210> SEQ ID NO 78
<211> LENGTH: 434
<212> TYPE: DNA
<213> ORGANISM: Homo sapiens

<400> SEQUENCE: 78
actagtacca ccatgaagtt gtggctgaac tggatttttcc ttgtaacact tttaaatggt          60
ttccagtgtg aagtgcagct ggtggagtct ggaggaggct tggtacagcc tgggggttct          120
ctgagactct cctgtgcagc ttctggattc accttcactg attactacat gatctgggtc          180
cgccaggctc cagggaaggg acttgagtgg ttgggtttta ttagaaacaa agctaatggt          240
tacacaacag agtacagtgc atctgtgaag ggtcggttca ccatctccag agataatgcc          300
aagaactcac tctatcttca aatgaattcc ctgagagctg aggacacggc cgtgtattac          360
tgtgcaaggg gcgcttactg gggccaaggg actatggtca ctgtctcttc aggtaagatg          420
ggctttccaa gctt                                                             434

<210> SEQ ID NO 79
<211> LENGTH: 133
<212> TYPE: PRT
<213> ORGANISM: Homo sapiens

<400> SEQUENCE: 79

Met Lys Leu Trp Leu Asn Trp Ile Phe Leu Val Thr Leu Leu Asn Gly
1               5                   10                  15

Phe Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Thr Asp Tyr Tyr Met Ile Trp Val Arg Gln Ala Pro Gly Lys Gly Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Gly Ala Tyr Trp Gly Gln Gly Thr Met
        115                 120                 125

Val Thr Val Ser Ser
        130

<210> SEQ ID NO 80
<211> LENGTH: 431

```
<212> TYPE: DNA
<213> ORGANISM: Homo sapiens

<400> SEQUENCE: 80
gctagcacca ccatgaggac ccctgctcag tttcttggaa tcttgttgct ctggtttcca    60
ggtatcaaat gtgatattgt gatgacccaa tctccactct ccctgcctgt cactcctgga   120
gagccagcct ccatctcttg cagatctagt cagagcattg tacatagtaa tggaaacacc   180
tatttagaat ggtacctgca gaaaccaggc cagtctccac agctcctgat ctacagagtt   240
tccaaccgat tttctggggt cccagacagg ttcagtggca gtggatcagg gacagatttc   300
acactcaaga tcagcagagt ggaggctgag gatgtcggag tttattactg ctttcaaggt   360
tcatttgttc cgtggacgtt cggtcaaggc accaaagtgg aaatcaaacg tgagtagaat   420
ttaaagaatt c                                                         431

<210> SEQ ID NO 81
<211> LENGTH: 132
<212> TYPE: PRT
<213> ORGANISM: Homo sapiens

<400> SEQUENCE: 81

Met Arg Thr Pro Ala Gln Phe Leu Gly Ile Leu Leu Trp Phe Pro
1               5                  10                  15

Gly Ile Lys Cys Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Ile Val His Ser Asn Gly Asn Thr Tyr Leu Glu Trp Tyr Leu Gln Lys
    50                  55                  60

Pro Gly Gln Ser Pro Gln Leu Leu Ile Tyr Arg Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Gly Ser Phe Val Pro Trp Thr Phe Gly Gln Gly Thr Lys
        115                 120                 125

Val Glu Ile Lys
    130

<210> SEQ ID NO 82
<211> LENGTH: 20
<212> TYPE: DNA
<213> ORGANISM: Artificial Sequence
<220> FEATURE:
<223> OTHER INFORMATION: 5' RACE primer

<400> SEQUENCE: 82
gccagtggat agactgatgg                                                 20

<210> SEQ ID NO 83
<211> LENGTH: 21
<212> TYPE: DNA
<213> ORGANISM: Artificial Sequence
<220> FEATURE:
<223> OTHER INFORMATION: 5' RACE primer

<400> SEQUENCE: 83
gatggataca gttggtgcag c                                               21
```

-continued

<210> SEQ ID NO 84
<211> LENGTH: 23
<212> TYPE: DNA
<213> ORGANISM: Artificial Sequence
<220> FEATURE:
<223> OTHER INFORMATION: GeneRacer 5' primer

<400> SEQUENCE: 84
cgactggagc acgaggacac tga                                         23

<210> SEQ ID NO 85
<211> LENGTH: 20
<212> TYPE: DNA
<213> ORGANISM: Artificial Sequence
<220> FEATURE:
<223> OTHER INFORMATION: 33E10 VH3' primer

<400> SEQUENCE: 85
gccagtggat agacagatgg                                             20

<210> SEQ ID NO 86
<211> LENGTH: 21
<212> TYPE: DNA
<213> ORGANISM: Artificial Sequence
<220> FEATURE:
<223> OTHER INFORMATION: 33E10 VL 3' primer

<400> SEQUENCE: 86
gatggataca gttggtgcag c                                           21

<210> SEQ ID NO 87
<211> LENGTH: 39
<212> TYPE: DNA
<213> ORGANISM: Artificial Sequence
<220> FEATURE:
<223> OTHER INFORMATION: 33E10 VH 5' primer

<400> SEQUENCE: 87
gggactagta ccaccatgaa gttgtggctg aactggatt                        39

<210> SEQ ID NO 88
<211> LENGTH: 49
<212> TYPE: DNA
<213> ORGANISM: Artificial Sequence
<220> FEATURE:
<223> OTHER INFORMATION: 33E10 VH 3' primer

<400> SEQUENCE: 88
gggaagcttg aagttaggac tcacctgcag agacagtgac cagagtccc             49

<210> SEQ ID NO 89
<211> LENGTH: 39
<212> TYPE: DNA
<213> ORGANISM: Artificial Sequence
<220> FEATURE:
<223> OTHER INFORMATION: 33E10 VL 5' primer

<400> SEQUENCE: 89
ggggctagca ccaccatgaa gttgcctgtt aggctgttg                        39

<210> SEQ ID NO 90
<211> LENGTH: 50
<212> TYPE: DNA
<213> ORGANISM: Artificial Sequence
<220> FEATURE:
<223> OTHER INFORMATION: 33E10 VL 3' primer -continued

<400> SEQUENCE: 90
ggggaattct ttggattcta cttacgtttg atttccagct tggtgcctcc                50

<210> SEQ ID NO 91
<211> LENGTH: 342
<212> TYPE: DNA
<213> ORGANISM: Homo sapiens

<400> SEQUENCE: 91
gaagtgcagc tggtggagtc tggaggaggc ttggtacagc ctggggttc tctgagactc      60 tcctgtgcag cttctggatt caccttcact gattactaca tgatctgggt ccgccaggct   120
ccagggaagg gacttgagtg gttgggtttt attagaaaca aagctaatgg ttacacaaca   180
gagtacagtg catctgtgaa gggtcggttc accatctcca gagataatgc caagaacatc   240
ctctatcttc aaatgaattc cctgagagct gaggacacgg ccgtgtatta ctgtgcaagg   300
ggcgcttact ggggccaagg gactatggtc actgtctctt ca                      342

<210> SEQ ID NO 92
<211> LENGTH: 114
<212> TYPE: PRT
<213> ORGANISM: Homo sapiens

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ile Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ala Lys Asn Ile
65                  70                  75                  80

Leu Tyr Leu Gln Met Asn Ser Leu Arg Ala Glu Asp Thr Ala Val Tyr
                85                  90                  95

Tyr Cys Ala Arg Gly Ala Tyr Trp Gly Gln Gly Thr Met Val Thr Val
            100                 105                 110

Ser Ser

<210> SEQ ID NO 93
<211> LENGTH: 342
<212> TYPE: DNA
<213> ORGANISM: Homo sapiens

<400> SEQUENCE: 93
gaagtgcagc tggtggagtc tggaggaggc ttggtacagc ctggggttc tctgagactc      60 tcctgtgcag cttctggatt caccttcact gattactaca tgatctgggt ccgccaggct   120
ccagggaagg gacttgagtg gttgggtttt attagaaaca aagctaatgg ttacacaaca   180
gagtacagtg catctgtgaa gggtcggttc accatctcca gagataatgc caagagcatc   240
ctctatcttc aaatgaattc cctgagagct gaggacacgg ccgtgtatta ctgtgcaagg   300
ggcgcttact ggggccaagg gactatggtc actgtctctt ca                      342

<210> SEQ ID NO 94
<211> LENGTH: 114
<212> TYPE: PRT
<213> ORGANISM: Homo sapiens

<400> SEQUENCE: 94

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

Ser Leu Arg Leu Ser Cys Ala Ala Ser Gly Phe Thr Phe Thr Asp Tyr
           20                    25                    30

Tyr Met Ile Trp Val Arg Gln Ala Pro Gly Lys Gly Leu Glu Trp Leu
           35                    40                    45

Gly Phe Ile Arg Asn Lys Ala Asn Gly Tyr Thr Thr Glu Tyr Ser Ala
      50                    55                    60

Ser Val Lys Gly Arg Phe Thr Ile Ser Arg Asp Asn Ala Lys Ser Ile
65                    70                    75                    80

Leu Tyr Leu Gln Met Asn Ser Leu Arg Ala Glu Asp Thr Ala Val Tyr
                  85                    90                    95

Tyr Cys Ala Arg Gly Ala Tyr Trp Gly Gln Gly Thr Met Val Thr Val
           100                  105                110

Ser Ser

<210> SEQ ID NO 95
<211> LENGTH: 342
<212> TYPE: DNA
<213> ORGANISM: Homo sapiens

<400> SEQUENCE: 95

```
gaagtgcagc tggtggagtc tggaggaggc ttggtacagc ctggggggtt ctctgagactc    60
tcctgtgcag cttctggatt caccttcact gattactaca tgatctgggt ccgccaggct   120
ccagggaagg gacttgagtg gttgggtttt attagaaaca agctaatgg ttacacaaca    180
gagtacagtg catctgtgaa gggtcggttc accatctcca gagataattc caagagcatc   240
ctctatcttc aaatgaattc cctgagagct gaggacacgg ccgtgtatta ctgtgcaagg   300
ggcgcttact ggggccaagg gactatggtc actgtctctt ca                      342
```

<210> SEQ ID NO 96
<211> LENGTH: 114
<212> TYPE: PRT
<213> ORGANISM: Homo sapiens

<400> SEQUENCE: 96

Glu Val Gln Leu Val Glu Ser Gly Gly Gly Leu Val Gln Pro Gly Gly
1                   5                    10                15

Ser Leu Arg Leu Ser Cys Ala Ala Ser Gly Phe Thr Phe Thr Asp Tyr
           20                    25                    30

Tyr Met Ile Trp Val Arg Gln Ala Pro Gly Lys Gly Leu Glu Trp Leu
           35                    40                    45

Gly Phe Ile Arg Asn Lys Ala Asn Gly Tyr Thr Thr Glu Tyr Ser Ala
      50                    55                    60

Ser Val Lys Gly Arg Phe Thr Ile Ser Arg Asp Asn Lys Ser Ile
65                    70                    75                    80

Leu Tyr Leu Gln Met Asn Ser Leu Arg Ala Glu Asp Thr Ala Val Tyr
                  85                    90                    95

Tyr Cys Ala Arg Gly Ala Tyr Trp Gly Gln Gly Thr Met Val Thr Val
           100                  105                110

Ser Ser

<210> SEQ ID NO 97
<211> LENGTH: 336

-continued

```
<212> TYPE: DNA
<213> ORGANISM: Homo sapiens

<400> SEQUENCE: 97
gatattgtga tgacccaatc tccactctcc ctgcctgtca ctcctggaga gccagcctcc    60
atctcttgca gatctagtca gagcattgta catagtaatg gaaacaccta tttagaatgg   120
tacctgcaga aaccaggcca gtctccacag ctcctgatct acagagtttc aaccgattt    180 tctggggtcc cagacaggtt cagtggcagt ggatcaggga cagatttcac actcaagatc   240
agcagagtgg aggctgagga tgtcggagtt tattactgct ttcaaggttc atttgttccg   300
tggacgttcg gtcaaggcac caaagtggaa atcaaa                             336

<210> SEQ ID NO 98
<211> LENGTH: 112
<212> TYPE: PRT
<213> ORGANISM: Homo sapiens

<400> SEQUENCE: 98

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Phe Val Pro Trp Thr Phe Gly Gln Gly Thr Lys Val Glu Ile Lys
            100                 105                 110

<210> SEQ ID NO 99
<211> LENGTH: 336
<212> TYPE: DNA
<213> ORGANISM: Homo sapiens

<400> SEQUENCE: 99
gatatcgtga tgacccaatc tccagactcc ctggctgtca gtcttggaga gagggccacc    60
atctcttgca gatctagtca gagcattgta catagtaatg gaaacaccta tttagaatgg   120
tacctgcaga aaccaggcca gcctccaaag ctcctgatct acagagtttc aaccgatttt   180
tctggggtcc cagacaggtt cagtggcagt ggatcaggga cagatttcac actcaccatc   240
agcagcctgc aggctgagga tgtggcagtt tattactgct ttcaaggttc atttgttccg   300
tggacgttcg gtcaaggcac caaggtggaa atcaaa                             336

<210> SEQ ID NO 100
<211> LENGTH: 112
<212> TYPE: PRT
<213> ORGANISM: Homo sapiens

<400> SEQUENCE: 100

Asp Ile Val Met Thr Gln Ser Pro Asp Ser Leu Ala Val Ser Leu Gly
1               5                   10                  15

Glu Arg Ala Thr Ile Ser Cys Arg Ser Ser Gln Ser Ile Val His Ser
            20                  25                  30
```

-continued

```
Asn Gly Asn Thr Tyr Leu Glu Trp Tyr Leu Gln Lys Pro Gly Gln Pro
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Phe Gln Gly
            85                  90                  95

Ser Phe Val Pro Trp Thr Phe Gly Gln Gly Thr Lys Val Glu Ile Lys
            100                 105                 110
```

What is claimed is:

1. A humanized antibody or an antigen-binding fragment thereof that immunospecifically recognizes the RGD sequence, comprising:
   (i) a H-chain comprising a VH, said VH comprising the amino acid sequence of SEQ ID NO: 92, 94 or 96; or
   (ii) a L-chain comprising a VL, said VL comprising the amino acid sequence of SEQ ID NO: 98 or 100; or
   (iii) both (i) and (ii) above.

2. The humanized antibody or an antigen-binding fragment thereof according to claim 1, wherein said VH comprises the amino acid sequence encoded by the nucleotide sequence of SEQ ID NO: 91, 93 or 95, and said VL comprises the amino acid sequence encoded by the nucleotide sequence of SEQ ID NO: 97 or 99.

3. The humanized antibody or an antigen-binding fragment thereof of claim 1, wherein said VH comprises the amino acid sequence of SEQ ID NO: 94, and said VL comprises the amino acid sequence of SEQ ID NO: 100.

4. The humanized antibody or an antigen-binding fragment thereof of claim 1, wherein said H-chain comprises the amino acid sequence of SEQ ID NO: 25 or 27, and said L-chain comprises the amino acid sequence of SEQ ID NO: 29 or 31.

5. The humanized antibody or an antigen-binding fragment thereof of claim 1, wherein said H-chain comprises the amino acid sequence of SEQ ID NO: 25, and said L-chain comprises the amino acid sequence of SEQ ID NO: 31.

6. A composition for inhibiting cell adhesion, comprising the humanized antibody or an antigen-binding fragment according to claim 1.

7. A composition for inhibiting binding of an osteopontin to a cell, comprising the humanized antibody or an antigen-binding fragment thereof according claim 1.

* * * * *